United States Patent [19]

Jalkanen et al.

[11] Patent Number: 5,851,993
[45] Date of Patent: Dec. 22, 1998

[54] SUPPRESSION OF TUMOR CELL GROWTH BY SYNDECAN-1 ECTODOMAIN

[75] Inventors: Markku Jalkanen, Piispanristi; Marku Mali, Salo, both of Finland

[73] Assignee: BioTie Therapies Ltd., Turku, Finland

[21] Appl. No.: 488,199

[22] Filed: Jun. 7, 1995

Related U.S. Application Data

[63] Continuation-in-part of Ser. No. 258,862, Jun. 13, 1994, abandoned.

[51] Int. Cl.$^6$ .......................... A61K 38/17; A61K 38/16; C07K 14/47; C07K 14/705
[52] U.S. Cl. .................................. 514/12; 514/8; 514/21; 530/395
[58] Field of Search .................................. 514/8, 12, 21; 436/64; 530/380, 395, 808, 827

[56] References Cited

FOREIGN PATENT DOCUMENTS

| | | |
|---|---|---|
| WO 90/09441 | 8/1990 | WIPO . |
| WO 90/12033 | 10/1990 | WIPO . |
| WO 92/00109 | 1/1992 | WIPO . |
| WO 92/13274 | 8/1992 | WIPO . |
| WO 93/03743 | 3/1993 | WIPO . |
| WO 93/05167 | 3/1993 | WIPO . |
| WO 94/12162 | 6/1994 | WIPO . |
| WO 95/00633 | 1/1995 | WIPO . |

OTHER PUBLICATIONS

Mali, M. et al., "Suppression of Tumor Cell Growth of Syndecan–1 Ectodomain," *The Journal of Biological Chemistry* 269:27795–27798, Nov. 1994.

Bernfield, M. et al., "Biology of the Syndecans: A Family of Transmembrane Heparan Sulfate Proteoglycans," *Ann. Rev. Cell Biol.* 8:365–393 (1992).

Breakefield, X.A., and DeLuca, N.A., "Herpes Simplex Virus for Gene Delivery to Neurons," *New Biol.* 3(3):203–218 (1991).

Elenius, K. et al., "Binding of Human Syndecan to Extracellular Matrix Proteins," *J. Biol. Chem.* 265(29):17837–17843 (1990).

Elenius, K., et al., "Growth Factors Induce 3T3 Cells to Express bFGF–Binding Syndecan," *J. Biol. Chem.* 267:6435–6441 (1992).

Elenius, K., et al., "Induced Expression of Syndecan in Healing Wounds," *J. Cell Biol.* 114(3):585–595 (1991).

Huang, Q., et al., "Introduction of a Foreign Gene (*Escherichia coli lacZ*) into Rat Neostriatal Neurons Using Herpes Simplex Virus Mutants: A Light and Electron Microscopic Study," *Exp. Neurol.* 115:303–316 (1992).

Inki, P., et al., "Immunohistochemical Localization of Syndecan in Mouse Skin Tumors Induced by UV Irradiation," *Am. J. Pathol.* 139(6):1333–1340 (1991).

Inki, P., et al., "Syndecan in Carcinomas Produced from Transformed Epithelial Cells in Nude Mice," *Lab. Investig.* 66(3):314–323 (1992).

Jalkanen, M., et al., "Heparan Sulfate Proteoglycans from Mouse Mammary Epithelial Cells: Localization on the Cell Surface with a Monoclonal Antibody," *J. Cell Biol.* 101:976–984 (1985).

Jalkanen, M., "Biology of Cell Surface Heparan Sulfate Proteoglycans," *Med. Biol.* 65:41–47 (1987).

Jalkanen, M., et al., "Cell Surface Proteoglycan of Mouse Mammary Epithelial Cells Is Shed by Cleavage of Its Matrix–Binding Ectodomain from Its Membrane–Associated Domain," *J. Cell Biol.* 105:3087–3096 (1987).

Jalkanen, M., et al., "Loss of Syndecan (cell surface proteoglycan) Expression in Mouse Mammary Epithelial Cells After Transformation with a Point–Mutated cHa–ras Proto–Oncogene," *J. Cell. Biochem. Suppl.* 0 (13 Part B):52, Abstract No. D 317 (1989).

Jalkanen, M., et al., "Simultaneous Loss of Syndecan Expression and Epithelial Phenotype in S115 Carcinoma Cells Exposed to Steroids," *J. Cell. Biochem. Suppl.* 0 (14 Part A):153, Abstract No. A 113 (1990).

Jalkanen, M., et al., "Binding of Extracellular Effector Molecules by Cell Surface Proteoglycans," in: *Receptors for Extracellular Matrix*, J.A. MacDonald and R.P. Mecham (Eds.), San Diego: Academic Press, pp. 1–37 (1991).

Jalkanen, M., et al., "Stimulation of Syndecan Gene Expression in Mesenchymal Cells by bFGF and TGFβ," *J. Biochem. Suppl.* (15F):223, Abstract No. CF 115 (1991).

Jalkanen, M., et al., "Syndecan, a Regulator of Cell Behaviour, is Lost in Malignant Transformation," *Biochem. Soc. Trans.* 19(4):1069–1072 (1991).

Kiefer, M.C., et al., "Ligand–Affinity Cloning and Structure of a Cell Surface Heparan Sulfate Proteoglycan that Binds Basic Fibroblast Growth Factor," *Proc. Natl. Acad. Sci. USA* 87:6985–6989 (1990).

King, R.J.B., et al., "The Role of Receptors in the Steroidal Regulation of Tumour Cell Proliferation," *J. Steroid Biochem.* 7:869–873 (1976).

Koda, J.E., et al., "Heparan Sulfate Proteoglycans from Mouse Mammary Epithelial Cells," *J. Biol. Chem.* 260(13):8157–8162 (1985).

Leppä, S., et al., "Syndecan Expression Regulates Cell Morphology and Growth of Mouse Mammary Epithelial Tumor Cells," *Proc. Natl. Acad. Sci. USA* 89:932–936 (1992).

Leppä, S., et al., "Steroid–Induced Epithelial–Fibroblastic Conversion Associated with Syndecan Suppression in S115 Mouse Mammary Tumor Cells," *Cell Reg.* 2:1–11 (1991).

Mali, M. et al., "Sequence of Human Syndecan Indicates a Novel Gene Family of Integral Membrane Proteoglycans," *J. Biol. Chem.* 265(12):6884–6889 (1990).

(List continued on next page.)

*Primary Examiner*—Nancy Degen
*Attorney, Agent, or Firm*—Sterne, Kessler, Goldstein & Fox P.L.L.C.

[57] ABSTRACT

Methods of reducing tumor growth, including the suppression of tumor growth in a patient, are provided by the administration of efficacious levels of syndecan ectodomain to the extracellular environment of the tumor cell. Pharmaceutically acceptable compositions of syndecan are also provided.

24 Claims, 22 Drawing Sheets

OTHER PUBLICATIONS

Mali, M., et al., "Inhibition of Basic Fibroblast Growth Factor–Induced Growth Promotion by Overexpression of Syndecan–1," *J. Biol. Chem.* 268(32):24215–24222 (Nov. 15, 1993).

Miettinen, H.M., and Jalkanen, M., "The Cytoplasmic Domain of Syndecan–1 is Not Required for Association with Triton X–100–Insoluble Material," *J. Cell Sci.* 107(6):1571–1581 (Jun., 1994).

Phillips, R.M., et al., "A Critical Appraisal of the Predictive Value of In Vitro Chemosensitivity Assays," *J. Nat. Canc. Inst.* 82(18):1457–1468 (1990).

Quintanilla, M., et al., "Carcinogen–Specific Mutation and Amplification of Ha–ras During Mouse Skin Carcinogenesis," *Nature* 322:78–80 (1986).

Rapraeger, A., and Bernfield, M., "Cell Surface Proteoglycan of Mammary Epithelial Cells," *J. Biol. Chem.* 260(7):4103–4109 (1985).

Rapraeger, A., et al., "The Cell Surface Proteoglycan from Mouse Mammary Epithelial Cells Bears Chondroitin Sulfate and Heparan Sulfate Glycosaminoglycans," *J. Biol. Chem.* 260(20):11046–11052 (1985).

Rapraeger, A., et al., "Cell Surface Proteoglycan Associates with the Cytoskeleton at the Basolateral Cell Surface of Mouse Mammary Epithelial Cells," *J. Cell Biol.* 103:2683–2696 (1986).

Salmivirta, M., et al., "Syndecan from Embryonic Tooth Mesenchyme Binds Tenascin," *J. Biol. Chem.* 266(12):7733–7739 (1991).

Salmivirta, M., et al., "Neurite Growth–Promoting Protein (Amphoterin, p30) Binds Syndecan," *Exp. Cell Res.* 200:444–451 (1992).

Sanderson, R.D., and Bernfield, M., "Molecular Polymorphism of a Cell Surface Proteoglycan: Distinct Structures on Simple and Stratified Epithelia," *Proc. Natl. Acad. Sci. USA* 85:9562–9566 (1988).

Sanderson, R.D., et al., "B Lymphocytes Express and Lose Syndecan at Specific Stages of Differentiation," *Cell Reg.* 1:27–35 (1989).

Saunders, S., and Bernfield, M., "Cell Surface Proteoglycan Binds mouse Mammary Epithelial Cells to Fibronectin and Behaves as a Receptor for Interstitial Matrix," *J. Cell Biol.* 106:423–430 (1988).

Saunders, S., et al., "Mammary Epithelial Cells Transfected with Antisense cDNA Reduce Cell Surface Syndecan and Become Fibroblastic in Morphology," *J. Cell Biol.* 109:5a, Abstract No. 7 (1989).

Saunders, S., et al., "Molecular Cloning of Syndecan, an Integral Membrane Proteoglycan," *J. Cell Biol.* 108:1547–1556 (1989).

Thesleff, I., et al., "Cell Surface Proteoglycan Expression Correlates with Epithelial–Mesenchymal Interaction During Tooth Morphogenesis," *Devel. Biol.* 129:565–572 (1988).

Vaahtokari, A., et al., "Associations Between Transforming Growth Factor β1 RNA Expression and Epithelial–Mesenchymal Interactions During Tooth Morphogenesis," *Develoopment* 113:985–994 (1991).

Vainio, S., et al., "Epithelial–Mesenchymal Interactions Regulate the Stage–Specific Expression of a Cell Surface Proteoglycan, Syndecan, in the Developing Kidney," *Devel. Biol.* 134:382–391 (1989).

Vainio, S., et al., "Syndecan and Tenascin Expression Is Induced by Epithelial–Mesenchymal Interactions in Embryonic Tooth Mesenchyme," *J. Cell Biol.* 108:1945–1954 (1989).

Vainio, S., et al., "Expression of Syndecan Gene Is Induced Early, Is Transient, and Correlates with Changes in Mesenchymal Cell Proliferation During Tooth Organogenesis," *Devel. Biol.* 147:322–333 (1991).

Wilkinson, D.G., et al., "Expression Pattern of the FGF–Related Proto–Oncogene int–2 Suggests Multiple Roles in Fetal Development," *Development* 105:131–136 (1989).

Yayon, A., et al., "Cell Surface, Heparin–Like Molecules are Required for Binding of Basic Fibroblast Growth Factor to its High Affinity Receptor,"*Cell* 64:841–848 (1991).

Phillips et al. "A Critical Appraisal of The Predictive Value of In Vitro Chemosensitivity Assays" J. Natl. Cancer Inst. 82(18)1457–1468 1990.

```
  1 ggagaggtgcgggccgaatccgagccgagcgagaggaatccggcagtagagagcggactc
    cagccggcggaccctgcagccctcgcctgggacagcggcgcgctgggcaggcgcccaaga
    gagcatcgagcagcggaacccgcgaagccggcccgcagccgcgacccgcgcagcctgccg
    ctctcccgccgccggtccgggcagcatgagcgcgcggcgctctggctctggctgtgcgc
                              M  R  R  A  A  L  W  L  W  L  C  A     12
    gctggcgctgagcctgcagctggccctgccgcaaattgtggctactaatttgcccccctga
    L  A  L  S  L  Q  L  A  L  P  Q  I  V  A  T  N  L  P  P  E      32
301 agatcaagatggctctggggatgactctgacaacttctccggctcaggtgcaggtgcttt
    D  Q  D  G ⓢ G  D  D  S  D  N  F ⓢ G ⓢ G  A  G  A  L            52
    gcaagatatcaccttgtcacagcagaccccctccacttggaaggacacgcagctcctgac
    Q  D  I  T  L  S  Q  Q  T  P  S  T  W  K  D  T  Q  L  L  T      72
    ggctattcccacgtctccagaacccaccggcctggaggctacagctgcctccacctccac
    A  I  P  T  S  P  E  P  T  G  L  E  A  T  A  A  S  T  S  T      92
    cctgccggctggagaggggcccaaggagggagaggctgtagtcctgccagaagtggagcc
    L  P  A  G  E  G  P  K  E  G  E  A  V  V  L  P  E  V  E  P     112
    tggcctcaccgcccgggagcaggaggccaccccccgacccagggagaccacacagctccc
    G  L  T  A  R  E  Q  E  A  T  P  R  P  R  E  T  T  Q  L  P     132
601 gaccactcatcaggcctcaacgaccacagccaccacggcccaggagcccgccacctccca
    T  T  H  Q  A  S  T  T  T  A  T  T  A  Q  E  P  A  T  S  H     152
    cccccacagggacatgcagcctggccaccatgagacctcaacccctgcaggacccagcca
    P  H  R  D  M  Q  P  G  H  H  E  T  S  T  P  A  G  P  S  Q     172
    agctgaccttcacactccccacacagaggatggaggtccttctgccaccgagagggctgc
    A  D  L  H  T  P  H  T  E  D  G  G  P  S  A  T  E  R  A  A     192
    tgaggatggagcctccagtcagctcccagcagcagagggctctggggagcaggacttcac
    E  D  G  A  S  S  Q  L  P  A  A  E  G ⓢ G  E  Q  D  F  T       212
    ctttgaaacctcgggggagaatacggctgtagtggccgtggagcctgaccgccggaacca
    F  E  T ⓢ G  E  N  T  A  V  V  A  V  E  P  D  R  R  N  Q       232
901 gtccccagtggatcaggggccacggggccctcacagggcctcctggacaggaaagaggt
    S  P  V  D  Q  G  A  T  G  A  S  Q  G  L  L  D  R  K  E  V     252
    gctggagggggtcattgccggaggcctcgtggggctcatctttgctgtgtgcctggtggg
    L  G  G  V  I  A  G  G  L  V  G  L  I  F  A  V  C  L  V  G     272
    tttcatgctgtaccgcatgaagaagaaggacgaaggcagctactccttggaggagccgaa
    F  M  L  Y  R  M  K  K  K  D  E  G  S  Y  S  L  E  E  P  K     292
    acaagccaacggcggggcctaccagaagcccaccaaacaggaggaattctatgcctgacg
    Q  A  N  G  G  A  Y  Q  K  P  T  K  Q  E  E  F  Y  A  *        310
    cgggagccatgcgcccctccgccctgccactcactaggcccccacttgcctcttccttg
1201 aagaactgcaggccctggcctcccctgccaccaggccacctccccagcattccagcccct
    ctggtcgctcctgcccacggagtcgtgggtgtgctgggagctccactctgcttctctgac
    ttctgcctggagacttagggcaccaggggtttctcgcataggacctttccaccacagcca
    gcacctggcatcgcaccattctgactcggtttctccaaactgaagcagcctctccccagg
    tccagctctggaggggaggggatccgactgctttggacctaaatggcctcatgtggctg
1501 gaagatctgcgggtggggcttggggctcacacacctgtagcacttactggtaggaccaag
```

FIG.1A

```
     catcttggggggggtggccgctgagtggcagggacaggagtcactttgtttcgtggggagg
     tctaatctagatatcgacttgttttttgcacatgtttcctctagttctttgttcatagccc
     agtagaccttgttacttctgaggtaagttaagtaagttgattcggtatcccccatcttg
     cttccctaatctatggtcgggagacagcatcagggttaagaagactttttttttttttttt
1801 ttaaactaggagaaccaaatctggaagccaaaatgtaggcttagtttgtgtgttgtctct
     tgagtttgtcgctcatgtgtgcaacagggtatggactatctgtctggtggccccgtttct
     ggtggtctgttggcaggctggccagtccaggctgccgtggggccgccgcctctttcaagc
     agtcgtgcctgtgtccatgcgctcagggccatgctgaggcctgggccgctgccacgttgg
     agaagcccgtgtgagaagtgaatgctgggactcagccttcagacagagaggactgtaggg
2101 agggcggcaggggcctggagatcctcctgcagaccacncccgtcctgcctgtgcgccgtc
     tccaggggctgcttcctcctggaaattgacgaggggtgtcttgggcagagctggctctga
     gcgcctccatccaaggccaggttctccgttagctcctgtggccccaccctgggccctggg
     ctggaatcaggaatattttccaaagagtgatagtctttttgcttttggcaaaactctactt
     aatccaatgggttttttccctgtacagtagatttccaaatgtaataaactttaatataaa
2401 gtaaaaaaaaaaaaaaaaaaaaaaaaaaaa
```

FIG.1B

```
      tctagatattcaaactcac cagatggagtgatgtccacc cctattggtgggagtgacta
-4138 gtctttcctctgtcttctga ctcagatgcttagctagctc tttaggaccaccctcacac ctgcaaataatactttattt
-4078 gctctcttagtaccctttaac ccagtggagttgacatgaga aattaactaccataatttat aatatttcattcataaatg
-3998 aaagtaaaataaattaaaa gtcttcagcttgagggaa atggcccagtggtaaggcc agtgctccaacgcaagtcc
-3918 tgacaaatggtaacgggcct atgtgctctccacactgca gttattgattgaggctaaa agcaacccaaggctccact
-3838 tgcctagtgtgaagccctgg gctacatagtataggctagc tgtccacctgtggtgtcagc acctggaagctgaggatga
-3758 tggggagtccaagtcatta cagaccatgggggggat tgggtacatgggtcacaaa aagaaaaaaaataagcac
-3678 attgtaatcccagcacttga tgaaccagtaatataaata tgctgtgagtttaagacagc ctgcctacaagaaaaacc
-3598 ctacccaaaccaagaaaaa ttcctattccctcctctcc gctattttcatttttaaatgc tctaaagacacagcgttaac
-3518 acaaagctctcgtctgtgg tttaaagacagggtctcact atgtagctccaactatttgg gaactcactgtagaccag
-3438 gcttgtttttgcttgct gatctaccactgcctc ccaagtgctgagactaagg catgtgacactttgcttggt
-3358 gctagcagggactataga aacattttgaacattaatag atgtatgtatatatatcact ctatgtagtatatgttag
-3278 tattacaaacatttaaaag atatttcactctcaaaataag ttttttgttttttttcttc ttttaaattatttatttt
-3198 acatttttcacttgagatac ttatatgtaagtacactgta gctgtcttcagacanaccag agaggggtcagatcttgt
-3118 ttttttttatttatta atgtggttgctgggattcga actctggaccttcgtttttt cagtcgggtgctcttaccca
-3038 tacggatggtgtgagcacc cttaaattatttttatctt atgtccattggtgtttgcc tgcatgtatgtgtaaagtg
-2958 ctgagccatctcaccagcc ctgttgtgagctaccattgt tgtgggtgctggacttgaa cctggtcctctggaagagc
-2878 tcagaaactgaagttacaga gagccatctctctagccctc agctgtcttcagacactcca gaagagggcgccagatctcg
-2798 agtcattattcttaaccact atattataatgtaagtacactgt aactccagacctttggaaga gcagtcagtgctcttaactg
-2718 ttttaagattttctattt atgtggttgctgggaattg acagggtttctgcctgtagct ctagctgtccaggaactagc
-2638 ttatggatggttgtgagcac cgttttttaggtttttgaag tctctgcctctcgagagc tgggattaaaagtgtgcagc
-2558 ctgagccatctctccagccc caaatttagagatttgcctg tattagagttaactagctt catttcagaaatactgcatg
-2478 tctgtagaccaggttggcct ggttttgaaaaagctttcca cttcagtgacaggcattcgg catgcctattagggaagtca
-2398 ccaacaatctactcaaagta tcatagctacttggtttt attttcagcttgacagacac tgtcaacctatgcagacagt
-2318 gaattcaaatgtggaccat ctgggtgagagggctaatgc cagacgctaagctccctacc tactctccatcagcttagat
-2238 aatggctgagaagtcatc attgcatgcagacctgcagt ccgtgtgaggatgttgtatc ttcttagattagtattcta
-2158 ctgctccagtcagatgtca ggctctctctctctctctc cctgtgaggatgttgtatc ctctggtactggagttatag
-2078 gtaagggtgctggaacaaa tacttcacttacatgtatgt tgatcctctggaagaatagt cagtgctcttaaccctgag
-1998 gtaagggtgctggaacaaa
-1918 ttttatttatgtaaattgg
-1838 acagctgtaagtcgccatac aggtgctgggaattgaaccc
```

FIG.2A

```
-1758  ccatctctccaacctcttgc  atattgaggacaggaggaa  tcacaagccatgtaggtgc  ctgggctctgaggtcaacag
-1678  gaccatagcctcctttcttt  atgtgcctttcttgggtct  ccctataggagtcgtcttcg  ttgcctcttactgtctcat
-1598  tgatctggctaaacttatg   cagttggaaagatcaa    gctggtcatgttaaaacat  gaaacagcctcatcagttcc
-1518  cttcctgttccgtctcccc   ccccctcccgccccattt   tgagaggacagaaggtaaa  ataccaaagtgtcctatttt
-1438  cctccaaatatcaggctcaa  aggactgaaagagctgacttc  agatcccaaagccactgtgt  taggaggcacctgctttta
-1358  gtcctaagccttcctgagc   cttgctattgggtattcttt  accaagaccctcaaggatct  agcaagaactgggcaggat
-1278  ctgtatgtagccatagtta   gacctaggcagctgagacg   ccaaaaggagagtttcctg  aggacaaaagtgttcaaaca
-1198  caactgggtgctggttgttg  ggctactcgtgagggtgtgg  tgtgtgtaaaggaggctgtt  gaattcccagaaggctgtt
-1118  ccacagtgtagagtctacac  tgggggacttcccagacgct  gagcctcagatctagcttct  cagtccagccagctgatgt
-1038  gggggctgaggaacaaggatg  gatgccatctatgccctgc   cttgcagtgtgcaaagggcct  ttggcaccatctacagattg
-958   agggcaagacagggctggtt  cttcctccttgctctcgctg  ctatctgcctcgcctgtagg  ctctctggctccttttttgg
-878   actgacacgtctgaaggagc  ttgaaactgtgaggtccag   gcccatagagaatcatgaa  ggaacaggaattcaactgga
-798   gctccgcagctgttaggcc   tgcggtcacctgaaacaa    gaggccatttattttttcct  ttggtcttggacaaggaaga
-718   gaagggctttctataaata   gaaagacagcaaaaagaa    ataataataataataataat  aataataataataataaaa
-638   caataacaagccagctctt   ccagacagtgctcatgtctt  taaaggtctttaaaggtctg  gagttccagcaattaagta
-558   aaggacaagacctcagggg   tccctatcctcagcccgtg   ggaggtgggaaccatacat  cgatcctcggttatatat
-478   agcctcatcgctgtgggct   ccgagttgccccccaaatc   ttgctcacctggagaccc   tgggtgtcctcgccagagg
-398   gcgctgcagcctcgcacgta  gagaactaacatcgcccttc  tccagggcagtgcctccga  ctccgaccaggacatagta
-318   gcgagtgcacctggtctcc   gtcagctacgcaagagct    ggtgcgacgcggaattaca  gattgccggcactaccagt
-238   gctcaggggaaagtggg     actcagacctgcaagagctg  aagagtgggtgggcttcga  tcctagaggcgtggaaggg
-158   ggtgtggctggatccctggg  gggtggggtgggcgctgt    cgggcaacccaggggggcgg  ggcccgagggtggagattg
-78    ggactaccaggcccgcgga   gctggggtgggcggctagt   tttgcaactgcagagccttt  gggtttattataaggcgAG
3      CTCCGGGAGAGGTGCGGG    CCAGAGGAGAACAGAGCCTAA  CGCAGCAGGAAGGGACCTGGC  AGTCGGGAGCTGACTCCAGC
83     CGGCGAAACCTACAGCCCTC  GCTCGAGAGAGCAGCGAGCT  GGGCAGCAGGCCTGGGACAGC  AAAGCGCAGAGCAATCAGCA
163    GAGCCGGCCCGGAGCTCCGT  GCAACCGGCAACTCGGATCC  ACGAAGCCCACCGAGCTCCC  GCCGCCGGTCTGGGCAGCAT
                                                                                    Me
```

FIG. 2B

```
 243  GAGACGCGGCGGCGCTCTGGC TCTGGCTCTGCGCGCTGGCG CTGGCCTGCAGCCTGCCCT CCCGgtgagtgtggcccggg
      tArgArgAlaAlaLeuTrpL euTrpLeuCysAlaLeuAla LeuArgLeuGlnProAlaLe uPro 323  gcagggctgggaggcggcgg gaagccggactcgccactc   gccgatgccatgcaggcggc agcacgtggaggggagggg
 403  agcgggacttcttcccgcg  ctgcctggcggatcctggga tgttgagccctttaatgagg actcctgtcccaattcctct
 483  acgtccgtggatgccagga  ggctatcccagctcgtggtc cgggcgtcctgcagagtgga acctccattgttcccgct
 563  cccaattaagtaaaacgact ccacagggtctgagtcgcc  ggccttaggcgtccgccgg  ccttaggcgccgcttggagt
 643  tgctctccgttgctgtc    ttgctggccatctcagcggc ctggcctccgccagtgtccc ggaggatgcagtggcatgg
 723  ccaaacgcctttccataga  cctaattcaaaccagactg  caggctgcaccccagcgcc  gcggagtccgggcgctcggc
 803  cctttgcaccgggcaagtt  tgggcacagcagagccggcg cgggaacagggaagctga   cgttcgggtggcgggaggg
 883  acgggattaaggctgtttgt gggacacaagagggtggctc agggacttcgttttttctct ggctgcccagtgagccgg
 963  gccgagctggcagcgggagg ttccggaagttggcttcag  aacgctgaagacccctaagaa cccaacttgggtcgctga
1043  agttgtgctgcccccgagg  gcctcctccgcatggcccgc ggggggacccctccccgca  gtgaccccggtacggctct
1123  tcccctccccgactcggct  ttgtgctgaagccgcgcgta gggaaggcggtcccttgc   cgccagtagggcgcggg
1203  gaaagaggacgaacgtgga  gctggcgactgtgggggaa  gcttcgggtaggatgcagc  catccaccttggtgggtc
1283  gtctctctaatcagcggct  tggcacaaagagcttggtc  gagggtacccagaaagtgc  tctccgcccaagccgccg
1363  tcgctagcccgccttccaa  cgggcgctttgttctcggcc cctgtaaccctttccctgga accgcccagcgctggtc
1443  cttgacgtgggcgggtcct  gggtcgcgccagtgtcagc  gctgccctccggtgtccacg ccctagccccgcaccgc
1523  tgtgaagtcccgggtgtcct ttccactgcgctttgccca  accctgaaggcagaggcg   agtgcggagcctcaggctt
1603  tatcctcccggaagtggcag tctccaccgccacatctg   tctgcttaactgcgatagtc ctgcaaggcagacagtg
1683  cacagggaagagagttgag  cgctggtagataccaagtc  gtgtacaaataaagtggcac agacacgtccccagtcact
1763  gttaatgcattgccttcgct ccttcccagtggctggtgc  tctccatcactctggagccc aagagagggcctccataatt
1843  gtattgccatgagttgggg  ttgtgtggggcgccaaatc  agggttctgggaggggcta  tgaattccgaactgagtctc
1923  ctgtgcactcctggcttgaa ggttcaagaaattgtttgag ggttgtggttttgtgggac  tcagattatgctggaatca
2003  tagttaccactgtggagaag aaagtggagctacttagcat gcctcccgccgccgctgc   attacctccggctctgttct
2083  ctaggcccaacgtgaggcct cactgggcagtacagatgc  agtactgaattcttttccag ccagatctggagaggtggt
2163  gttctctctcggtgtctt   tagagaggcagatattcctg tgacctaagccctcaagca  ccattaataatgctgagta
2243  gacaactagaggtggcgttt tccggaacttcctgtgct   ggcctggaggttgaacct   ctaggaaacaggtctaggaa
2323  gtagaattatctcaatgaa  ggcttcctgaggaagaaga  tgagctgagcccccaggtca ctgtctgagctttaggatca
2403  gactccacttgaggcaag   agtgttcgttttacttttt  ttttaagtttagtttattt  tctctctaacagaaaacaaa
2483  caaacaacaaaaaaaaacc  ccacattgtttaaaagtggg tgcataagagtgaggacata ttcagacttcccctttcc
2563  tgaaaatgaaggcagctgg  gatttacttaaaatgagagc acatatccacaattgccagag agctggtccctttctcaggg
```

FIG.2C

```
2643  ctccctaagctcctgtggga  agcaggtcagacagccctg  ggaccagagataggggagt  gcttttggtgcctgccttt
2723  gaatgggaaggggggggga   gctgctgggatcagaggctg ctagcaactactcccagag  actgaagcaggtttgtccct
2803  cagtgtcctggtcttctg    tttctcctatatagaatagg agaaatggttatttgctctg gaatagtgacttgctatttg
2883  ttcccttctcttcctctcc   ttactgtaatcatttggact agtagagacacttttcccag gtctggcagaatgggaggga
2963  gtggggaggcctgtgcttg   catgatgtcactgctgctt  cagctctccaggaggggtgg agttggttgtaacctacctg
3043  tggctcttgatgggccacaa  taaaacctcattaacacaca ttggtagggagaagggactg gaaagaatgatgggaaagat
3123  tgatgtttttccttttttt   tttttttttttttggcagta ctttctagatctcccctccc cctgtctgcagcaaaattt
3203  ggattcctgaagtcctttga  gaatgtataatggtagccag actttttttttttcagtcag ctcaaaattgcctcttata
3283  aagtatcctggttgttgtttt tgttgttgttgttgttgttg tttgttttgttttaagaca  agtttcctgtatagtcct
3363  ggctgccctgaactcaata   tgtagaccagctgbcctca  aactcaaagaaatccaccta cttctaactttcagtgctg
3443  gcctaaagtgtaggccacc   aaaagtgctcaacttttaca agcagtcttactttgaca   ggattctgaaaccctattt
3523  ccttctgttatcttcaaca   atacactgctagtgtattt  agtcccatgatgctggc    ctcctcaagtggcgccagt
3603  caagcagtctccggttttt   ggtggctctgaagaagactg tgtccagtgactggcagtt  tgaattcggagcttctctt
3683  tccttctcagtcttttggcag gcagagtgacactggtgtgc ccaagctggagcttctctg  tttaattctagtttatttc
3763  tttatcagactgaaaaacaa  atcaggttggttataattct tataaacacgaaggtctcac ctttgcgtacgtctccgct
3843  gtgtgggtctgatgtccctc  gggaatctctgttgaggctg ctgcagtgtgtgtgcgtgta gaaaggcaaggtagaatgg
3923  acagaagcgtgctgcccacc  ccactgtcctgttcctaaat gatgaagcactggcccgtg  aagagcctagagaactccct
4003  cgtgggagatgcacacaat   gccagaagcacacaaggctagct ttgagttccagcttggcagt  gtctctcttttggtgacttt
4083  atcagctccagtgccctgg   actaacaaacaaggctagct cactctcagtattgataatc gaagtcctgttctgttt
4163  gagactgatcctcactcggt  agcctgaactcttagcaat  tctcctgtctcaactttcaa agagctgaaattacagactc
4243  gagcaccatatgcgactga   aacctgttcctaatcctttg actgtgaacgactcttggt  ttggttcttttccattcct
4323  ttagtgtatgtttagttcg   cgtcctacataatcttattgc ccatacttagaaacaacagg  ttagagacagcattggtcc
4403  agcagagcctcacactgaag  ctcagtcctgccactgattt accgtgtcagctcaagtgac tcacttccaactcctctgct
4483  cccatctgtagagtagaca   tcaccataacctgctcttct gccacattctgtcattaac  atgttcatttcataacgatg
4563  gtgcaaaagtgcttttgtaag taaagtgctggggaaatgtt agctgtcgataatggttagg gttaacttttttattgagtgc
4643  ctgttgtgtggggttggg    tggggttttttagaggctt  ggtagttttcttacttcttt cctactagcttttcttcct
4723  aagcttttatggtatgtatc  attgcctgattgtttgagtg tgtgcactgaggcacgcctg tgcatgtttgagagtatgct
4803  tgtgcgtgctcgtgctca    catatgtatgtgaatac    actgtagagtgcaggccggc acactgggctggctgaatc
4883  ctgtgagccctgcctggagt  ttgcagatcttccttggaca ctcctgcttgtgagcatttt gtgtggagtgactgtttagc
4963  tggctgtagcctacattgtg  cctttggtaaaccctgagt  attgggaaacaccctgggct gtggctgtgtgccgacg
5043  gttgcttgggtacagctaag  aactcttcatagaaagttga gctcacatgctattagtatt aactgagtgctaaggaacct
5123  gtcttgggtggtacctgctt  gccctctcatgcagtttatc ttgagcttggcgaacacact tacagatttagtagagcttt
```

FIG. 2D

| | | | | | |
|---|---|---|---|---|---|
| 5203 | tgtcagccctggaggtggg | tttcgtggccacaagtgggt | agcttggaatccaagactcc | tggcttctaggttgcattct |
| 5283 | cctgtgttctttccaaggg | aatgctagggaacattttg | gacattagattatttctagt | cccaaagcacacagaacata |
| 5363 | ctgtttcctaattgccttt | tttgtttcctctcaatct | ggttttgaagtgttgggttt | gaaaattgcccctgagagc |
| 5443 | ctgcctagtgtgtgcagag | ggaagatagtggaacaggaa | gtctgtagaaagtatcttcc | tttccagacctgtgcccc |
| 5523 | ggagcagagtcagcatggtg | tcatatgcttttggctatt | ccagaagagatgaggtttta | ggtgagaatgaacctttag |
| 5603 | aacctttctagaaccttctgt | tgagtatgacaggaatgccc | tgaataggtccgaagtgca | tgccacttgttgtctttt |
| 5683 | ccataagcagcagcttcag | gtacagacaataagactagg | ttcttggagtgagaccctgc | acttgtgccatttcagctc |
| 5763 | cagatggacactggagtcc | ctacacagcaggctctggga | tggctgctttgctatgtac | tgttgcctgctctacaagag |
| 5843 | cttccagttactagcctt | tgtcgacgctggctgctg | gccaggcttgggcattggag | aaggacaacttgccacctg |
| 5923 | gcataggctgtgtgtttgga | gagtcaggaggtctgtgaa | gcccgcaagtggaggcaagt | ttagtggactgaggagag |
| 6003 | ctcagtaggaaatctctggg | ctagtagcaggcaggtgtgg | tgtggtggcgaggtgcgg | gtctagatctcctttttagag |
| 6083 | atttgctagggatcgtccc | tgctgactctggaactcaga | ggcctccagaggtgtctcct | ctggagcctctcaaggtc |
| 6163 | tccatctcctactgtttat | ggcttttgtgggctacctaat | tacatagagaagatatgttc | ctctgcctccagccctggaa |
| 6243 | agttctgccagtgactcac | ctgagcctgcagccatgtgt | gtacacaggcgctctcagg | gcttctgtcctgctggcttc |
| 6323 | agcctttctagccccctggtg | ttctcggcagtggtagcatc | tgggaaaccggtcacctct | tatttgcagctccctccctt |
| 6403 | tcttggtgtcttccccctttt | ttaactactggtctgatggc | cttagactcatgctgaaatt | ctcctttctttttgtcctagc |
| 6483 | ctgtctctgacttcttgtg | atcctctgggctgtgaaat | ccgctcagggcctccattt | ctaacagtcacacactggtg |
| 6563 | gagagaccgagtcctgggat | ggtgaagctaaccctgctgg | gcttctcaagcttcatttgg | tttctcttattcctttctgg |
| 6643 | agtactgcctgcccaggg | gagtctcagactagaccact | ctggagttggagtgggca | gttttcagatcagtgccct |
| 6723 | tgcattcgttgtgggaatg | ggttggatgggcctctggg | caaggtcaggctggggtgg | agccaggtgcctgcaggttggg |
| 6803 | cacccacaccaggcagcct | ggcaccctcccaagtccg | ctcatcagcaggaatgaaag | cagtgccggcaggttggg |
| 6883 | cagtggcaggtggcgtgt | ttatcgtgctcatcagc | tgagtcacgatgccaggccc | cacaagtcctccctggaggc |
| 6963 | tcacccaccaccacctgacc | caccagcaccactagcagg | agtaggcaggcagtgag | acaagaccagcctggggtc |
| 7043 | tgagaggcaaaggggagttg | ttcatgactgctgctgcat | gggacttgtggtgtctca | gatatctctgtcgtccagga |
| 7123 | ggaagctgtcttaagtgcca | acctgcctagagcccctgct | ggtgcaggaaatgcacaag | ggagagtgccatccatgga |
| 7203 | ataggccatggagctagac | cagtgacagtgaag | tcagccccaccctgtctt | ccgagccagctggaggttt |
| 7283 | ttatctcagattctgcgaaa | ccatagaatctagtcaggag | cctagactgcaaagcaggct | tcgttgatgctttaacttgc |
| 7363 | aggcttcctgggtatgagg | atacttagaaaggtcccgca | ggtagggagggcatcaggaa | gtagaagagggccaggcact |
| 7443 | tctatctcctgcattgcccc | cttctccatctccaaggat | ggtaaaaagaaccccttccag | tacactgacagagaggaaaa |
| 7523 | cccttcatctcaccccattt | ggatctgtcgtatcagcatg | tgctgccctgcttccatac | cagaggtggctagagatgtt |
| 7603 | cctgggaattcactggttg | gggacttgagtgtatcagag | gggcacaaagtaacattaac | tctggtatcctctgcagcaa |
| 7683 | atcggagatcccctctccta | ggcgagttctcagtggatat | ggaggtcaggtttgggcttg | tagggcccagcaagagtcg |

FIG.2E

```
7763  ttgatgtcactccagcttct cccgaggaagatgagggtgc tgtgtttgggatcacatctct ccctgaatggcatgttgggg
7843  agggatggagccctttgcttc tgaccctaagcttgtcttt tagttggccacagtctctgg gttctgtcctacctcctgc
7923  ccttgtgtgcttcaaaggca tgctaaagggactcctggcc attccgaatggcacagtgtt ccttctgttcctccaccccc
8003  agaaggaggcaggcctggat tgtagattcctagaagtaag tggccctgagcatgctgttg atgaacctggaaccaggcag
8083  gctgggcatcctagaacctg tcttccatagaagtctgaa tcagtctaccttttgggactg agtaagggctcctcacata
8163  tcagctggctagtccatctt ggctgatctaaaccacatta ggctgaagagaagcatggtg tacagtctggtccaccgaa
8243  ccacatactggctttatcag ttctcgtataatttgcagg taacttttagctctaagcc tgtctcctcatctgtgaaat
8323  cgggtcctcatatcctgcc tagaagggctttgaaaaga ttaatgaagtagtatgccga gtggttgggtttctctctt
8403  gactggagcaagtctctagg agtactaaggatagcctgct gtgtgcagcagcaccccaggga ctgtgcctgagtaggaggt
8483  acagagtcttcatgtgaatg gcccttctgtcttgccccg aagttagtgttgatgtcata gagtctacaaacatgccttt
8563  tgtccttcctcagaagtcca agcctttcctgcagaccag acattcatctccactgagcc tctatgtgagactggctcct
8643  ggcctgagctgtgtgggctg agctggcgaatgggaaaact agacacctgggcacctgggt ggggctcggacagcagtg
8723  tttcagttgtaggcactgtg ccctgcctggagcttctga ctgaaggttaccctgagagg aagcaggttcctatagaca
8803  ctaacatagctgggtcagag tgcaagtgggtgtgccct gccctgaccattcagtgca aagctgctcttctgggagt
8883  gagagctctgacaggactgt gatggccgagggtctcaga gcaaacctgcctgcctctc cccactctgatgatatgtg
8963  ctcttaaacaagtgactgtc cactttgcctcaatttcaac atctgtaagatagatagggc gttatgtctgaaaatggtt
9043  ttaaagattagttagctaat acaggaaagtgctctgaca ggtacctggcaccttactca acaagtggctggatgcctg
9123  atttcctaaggtctcgacct gtccctatgtcttcaagtgc cctacagcctttgtcaggcc cttaggttctccaccacc
9203  gctggcccaggacctagac tgctggacccctgaccccatt tttcctttaagccaccctg cgtcaactctaaaaggcggt
9283  ggagttgtttatctaggctg tgagtgtcagagaaaggac ctgggccgcttttgttcctgt gtgggctgggccactccag
9363  gaactgagaaaccaccac cttttcaaaaacagcctctt ctcagagtctggcacctcag ctagccaccatgctgtggga
9443  ccactccagcatgctcctgc cttggtttgttccaggg gcctcagtgcctttaaaga tgcacaggcatctttagttc
9523  aagggaaagaggaaatgaa gtgtatttgctggtggtggt attcctgtcacttgcattct cacagaggctaaagaatttt
9603  gctctttgtatcttctagtc tcttcttttatgatcttttcc catctgttgtatcccaactg cagggcccccagttctagaat
9683  tagccctccccataggaa gccgacttatgctataatgt gaatgacaagtatcctttag cccttccacacggcattta
9763  atttttcaaaagggcattgca caaccgcagagacactaaga agagaggtttggtgatcaga gttacagccccagcctcca
9843  gctggtggccggctggtgc agtgtgtcgaaagcagtag tttctgcttcagtgaaactt gaggatccttttattagcca
9923  gttcagggggcggaatggcca tgcgaagtctatgtgtcaca ggtgtcaggccccccatatcc tgctgagtctagaatcagct
```

```
10003  acgtagcagttttggggta ttgccagactgggagtttac atcccagaagcgagaatggt gggttcctatactgctcca
10083  gacaggatctttccccaag tttgtcagccacctctcttc aagtccctggctctgacca gcaagacgtatccaaaagaa
10163  actgagaggcccttcactt cttttaggatagtgtgggg ccagcatggtggggttggg aatggctttctgtctcttcc
10243  atcatcacaggctacttcc agagacactttgattctgg catctccagcagtcacctgg cccacaatgctttgctgccc
10323  tttgcttcagccactgtatc tggttgtccctgaagtga gccagagctcctaggcagag agcatgtgctatacaaagcc
10403  gtaggctgggcctgggaac cttcttgctgtcatcctcct gtcaaaccctatggtatgg tagcccataaggcttgtg
10483  caaaaacaggccaaaacat aagttatctttcactctat cggtctttctcattttcca tggtacgttcggctgccag
10563  gcccaaaagatttgaagag ggtggctggcaagtctaggg gaataggtctatctggttcc ctccaggagcagtgcctagt
10643  gagaggctgggctggcagg gcagggcccctgctccaca ttgcctgaagtcccgccctg cccgtcctgctggatctg
10723  gcagtctttccagtccaca cccggtctctcagctgagcct gctcagagactagtcctgc atgtgggttgcagggctggt
10803  tccagctccaccaggagta tgggcgtctggtactcatg ggacattgacctgtagtgg tatggagagtgggaatgg
10883  tacaggcagtgtgctggtg ctgacggactgactccggc attgaccttggcttgcagtc tggtgttaaactaacagga
10963  atgctgacaaaaagacagt tattaaaaccaagacagat actgcttccactcagccc attccaagaatcccaaga
11042  cgtacaggaaatgtgcaaca gcagtgggaattgctgagtt ggggatgtgggtgagctgt gtgctcccaggaattttgg
11123  gaaattccctccgttgaaa tgctgtcaggtctgagcct tgagtgttttttggggtgc tgtgctcccagctaagcag
11203  ctaacagtcctctttactg ccttgtcctcacctgcccc acctggttggctcctcg ttcactcctgctggtcac
11283  cagtacttcagtgcaggtct cagcttgattcttggtggag agagaaagttgataaatc agggtgctgtcagccggaa
11363  atttgggtgtgtcctgaagg caccaatgggggccctcct tctgaggtggcttaagaa gggtttctgggtcttgagg
11443  cctcctacagttttcttagc tccatgggagaagtgagg agttgggtatcgtcaccca gcatgaatctctggtcacct
11523  ctcagcatgcactgtccagc ctgatctttgagtgccataa aagaacagaattatcctctc agagcacttcattcccgcc
11603  agcacagtgggtacagagac aagctgccagactcccagc gagggactagttgagccca gcatgggactagttgagcta
11683  gacctgatacagtcccagag agcctcgttgaggaagcttt gggaaaattcaccagcatt tcagccaggactggagaaa
11763  agtgattatgggaaagaga gcagtcaagacccaggctg taggacacaggatacaaact gagagctaccggataggagt
11843  agtttagtcacaatctct cctgtccgccctaccctcca ggagacattgcaccttgtag aacagctgcccggagtcca
11923  ccttgggccccctgggta gctcagtagtgtcagcatcc tctcattgacatcagtcagg ttacacagtggggcagctaa
12003  tgtgaaggcgctaggctggg aagcagctacttgggaaaa ctagttgttcctgtagcc cctagcaggaaggcagttcc
12083  tccttttcttggtggcttta ggggtctttgaagcttgat atgttccctcagctcgttgg tgaagcaggccctcctggta
12163  ctgtggtgttgtcttcgaa gagtgaaggcattgaagta aagactgatggggcgcttc ccaggatgctttgctcttg
12243  cgctggcttacagagctct ttgctacctagtcgtccttgac tttgaacaccagattcagtc agggaacaggagtagaggtc
12323  ttgccttgctgagccctgc gcactgcaggaaaagactcc tctgagtggagcctttcctc ctcaggtgactgctttcaaa
```

```
12403  gtacagcagcctctgagggg  gaagtgtcatttgacattgt  ggtagttcttggggtccctg  gatacagatgtcatgccag
12483  atcatagtctgtttgtaca   gagggaggcgagttctgtag  ctcagagtcctcagtaccc   agagttgtggctctagggt
12563  gagagagaagactacagcc   cttcaatcacaggtctgacc  tgtgggtaggggtagatctc  ttgcatactatgaacctgtt
12643  tgaaaccctgggtatttgc   tgtggaatagagtcttggtt  gggtaagaatgtggatgtt   tatcttgtgtgactctcgg
12723  gtggggtggggatatgtc    cctgtctttccaatgtagt   atgctgagtggacagagacc  gtgtgactgaagcctggct
12803  cctggaacaggtgtgtgttg  gtgggggtggggcgcaact   atctggatccagactgctt   gggaatggctgtgaccagc
12883  tcctttgataacagcagctc  tttgtcactgatgttgtga   ctaatgggacttgttgattc  agttactcggctccaccca
12963  cagacgccgggcttctgtt   gtggcaccagcagctgcag   acgggcccacagtttgcctc  gctttcccactccacgaagg
13043  taagttcccagcactgccca  aattagagacttgtgagtgg  tccctcatacccactccc    tgaggctttctcctggaagc
13123  ctggaatgggcactggtg    tgtacgtgctgtgttctg    ttagggtcaagaccaggctg  tttcttacctggctcgtacc
13203  tccaagtttccaggtgatga  gtcctgattttttgaagtgaa ggaatccatttaatatcaaa  atctgtgaccttaaatttt
13283  tttcttttattatgtgtcat  ttcatatgtacgcatattt   tttgtctgtgtgtgacatg   ctgtggcgatcagagacca
13363  cttcagaaagtcagttctct  cctgccgtgtggtcctggg   gaatcaaatccaagttgtca  ggctttatcctgaaaataaa
13443  aagtagacagccctggat    ccaaagcttctaggctgt    gtgtcttagacaccaccagt  gttgcacagctggtaacatg
13523  acagtcctggagtgctga    ttggaagccacagcctctg   tgcagggcgtagacttcca   gggtacggggcaggtgggcg
13603  ttctctacaaaaccttgta   atcgcgacgtcttggagat   gcccctagtatcatgatt    ttggtgtgtgacacagctga
13683  actgtcttcatactcaggat  atcatgaagtgctgggtgc   agaccactctcagcctcagg  cagccaggaccggggctcc
13763  atcagattgcggtgactacc  acagagggtggccttcctc   cggtcagtgtggtgtggga   gctgcaggaagtggctcca
13843  ggcttccttaagcatcctc   tgcccacagcccaaacatg   ttctttggcaatggcttgca  actagaggtgaactctctcc
13923  tgtactatgtcctgacccac  gctgctgcatcttattatacc tttcacacgcgtgatggta   ccagcggggctgctaggca
14003  gggttaagcactcatcttgt  ttcctggtgctgaagctgtg  gtaaagaaactgaggccatt  ttcccttgagagagatggtc
14083  tcagccagttctttctcgc   ctggggagcccgaagaaag   gatgtactacagtgatgga   cactgttgctgatggcct
14163  tggtaggtccttcacctgg   gaagtgctgttttcttatctg ttagagatgctgacctcagc  aggactggaggaactgcatg
14243  ggaggtgtaggaatgaaagt  gagtgggaaattatctcc    agccctaggaagtctgagg   cctgtcccctttgtcctg
14323  gactgggccctgccttggg   tgtctgtccaggtctttgc   tctacagcccagcggatgc   ccaaagtagaacgagtcaact
14403  ggtccttttcttcacctgt   gtccacttctcatgtatcta  ccttcataatccttctagt   aaacaagcctctaactttg
14483  ggtttcaaatcagcagct    tccaggctcgatagtacgaa  ccatgaaaatctttcttacc  atgaggttgttttctagtgt
14563  gtgtgtgtgtgtgtgtgt    gtgtgtgtgtgtgtgtgt    gtacgtacacatgtacct    ctatcagtgtgctgcgtg
14643  taccacagactcgtgag     gaggtcaggcaaactttata  aaaatctttttttttgctt   cacttgagtcccaggtcac
14723  acagtggcaagtgctgagct  ctgttctctgttcttgattt  gttttgtgagcagctgatgt  tcttaaggcttgcggaggg
```

FIG.2H

```
14803  aaggtaggctggcttgct  tcttcccgagtggcgtca  atccctagacatctctaagc  cgtggccacacgtcctggaa
14883  ggaccaggtcagaagtgat  actgagatggccctgagc  cctctgaacacacaggtt  gtaaatagtacctgattgtt
14963  acattggagactcgtcagct  gggtggagtcctgttcaga  gggagttattcctccccca  catttcttcttctgggc
15043  tgaagtctcttccttcctta  cctgtgatgctgtcatgata  ggtcccagctgagagtggag  gcggggcagtcagggagctg
15123  cttctctttgctttagcaggg  gttggagacttgggtgtag  gggttggctccccctttccc  tgccctgaacctggtttctg
15203  gtttcagcagagattcgttc  tagaaacttgttgctaaac  aagatcacaaagcgataagc  ttgagcaaaaccagggaa
15283  caaattgctccctgtgaag  acccaatcttagctcttaga  gaagccctccctttgaaa  ttgctgactttcaggcttc
15363  tctgtggagaaagaggcta  gccgcgtatgtttgcctgg  attccaataatcttttgcgg  ccttgctacccttgttga
15443  acaagtctgcactcctaat  gcgtgcctcaggtggtctga  gacctctacccatctccag  cttttcctccatggagg
15523  agtcagtgggttaggagaga  atggagttgagtcctggaat  gaggaggaagctatgaactc  gggcctgttcctgtctgt
15603  gggtgctcttccgccgct  gaaggagcagccgcaggga  agactaccacaggaatccga  gtaccacctggacagtgta
15683  tacaggatgtgggctgatgt  gtggtaaggcatgatgggc  tgatgtgtggtaaggcatg  ggatctgattgctctgtgga
15763  tgggccacagggaaattttt  gagtgtctactgcagtagtt  ctcaacctgtgggttgtgcg  cccttgtgggagttacat
15843  attagatattacattatga  ttcataactgtagcaaaatt  acaattgtgaaagaaccaag  aaatcaccgcagcatgagaa
15923  cctgtattaaagggtcacgg  tgttaggagggtttgagagcc  actcatcctctggtctagg  ccatgcgggctgtaactgc
16003  tctctggagttaagccacag  tgaaccagctgtccttgcag  atgacttgtggaggctcca  aacctttgtccagggggaga
16083  agagcttgcttttgctttgt  actttaaaggaagttcagt  ggtcttcggccttgtggct  gctgtgtggaagtgcccc
16163  tgtacaataagctgtataga  tcgtgtacaactgcagtttt  cctccgtgggtccaccaacc  actcctgactccacggatga
16243  gtgaggccagtagggctgtg  tgtgggtccctaggccaagc  atcctgaccacgatgagcc  tcagctagaccactctgat
16323  cttagcagaggctcctaga  gagctggctggcttcctcct  gccttcttttctcttaaaac  ttcgtctcaatcggaagctc
16403  ctctgtgcacgtgacctcca  ggcctggggtcgccacaa  tcccctcatcacaagacgag  cagctcgcatgaggacacg
16483  acacttgttacctaccaggc  tgtgggttttttgttggttg  gttgttttgttttgttttgt  tttttactgtacagaagt
16563  gttgtgacatcagatgtcag  ctgttagtgctggcaccatt  ttacagtagggaactgagg  ctgtaagatgtgtagtgaca
16643  tcgctaaggccactcagttg  gtgaggccttaccaaggtca  ggtctttgagccttttgct  gaaccatgtacttctatctc
16723  tgttttgttgaaacaaagtc  tatatggctctggctagcct  ataacccatatgtagacga  ggctgacctcgaatacactg
16803  cagtcttttatgtctgcctt  ctgggtggcaggattgaagg  catgtgattcctcctaactg  tacactttaaaaaaaaatc
16883  attcttttgttctgtctgtg  ccagggcctttgtaagatgtt  ctgtgctgagctgggctatt  tgggttagtctcattgctga
16963  gcagggccctgtatcttcc  ttcctctgtcacttgcttacc  tgggtcttcctcctgcacta  gctatcctagaaccagtact
17043  gagagcaactatgggcccaa  ctctgcccttgcccagcct  gcttagctgggggcggtgtt  ccacttccctgcccaagtcc
17123  tgtgggactgtgttgtact  ccaccacttcagttcctg  gagctgagcaggccaggcg  gctgcattcctgcagctgct
```

FIG.21

```
17203   gttgcagggagagccatc  ccattcacttcagtctcctt  aatgtagaagccttgtcgaa  ttagcttccactgtcccaa
17283   cccagagtaccctgtcctt  tcttcactaagaaggccagg  atacagtccttcctgtggct  gataagacaggccttggac
17363   aaggcctgggaccacactgt  gtgggcaaagctgcttcagc  accgatggctcctccatgcc  aagcttggctctgcttctca
17443   cagttgagacttctgtgcgc  acacccactgtctagctcag  ctgacactgatttttcttta  aatgtatagatttgggtg
17523   gggtgtgcctgaaagctccca  ctgatgcccaagcctgagt  ctcagagtatgatcaattga  tggctttcatggtatcaca
17603   gcttctgttcccaggtcaga  ctccctgaccagtcagagca  tcctggggttagacaatgtc  cccgtcacttgtgcctccac
17683   ctggcaccaggctatgatgt  tatggcattgagggtatgag  aaggaccaggggttttcccag  agttacgcccaggcgcacag
17763   gcaattgtttcctacatgtg  tggctggaatggttggtga  gccttttcagctgctgcctacaa  taggaaccaggatactgg
17843   gcattgaccaaggcatatct  cataccctttcttatcttt  ctgcagCAAATTGTGGCTGT AAATGTTCCTCCTGAAGATC
                                                                     GlnIleValAlaVa   lAsnValProProGluAspG 18923   AGGATGGCTCTGGGGATGAC  TCTGACAACTTCTCTGGCTC  TGGCACAGgtaagactgacc  cagaacactgagatggcata
        lnAspGlySerGlyAspAsp   SerAspAsnPheSerGlySe  rGlyThrG 18003   gatcatggctggagtggtga  gcaggcagtcaccagcttt  tagtgaacccccttcttctc  ccatcccatccttagccatt
18083   ggagtcagagacagtgccaaa  aggaagaatggtatccagct  gcaagccactcagctaagag  aaactctcagagaatgaag
18163   gggttccaccaggccatggg  cagccactagagccaacct  tggaggagtttgactccact  gagccttggtgtgtgtttc
18243   catctgtgagatgggaatac  tttgcccaagagcctgttag  aagctgtaggaagcacagag  tcggctaggtatagatttgc
18323   tctcacctccatctcctgat  accagttctctgcagagctt  gggtttgtgtggagggtggg  ggggtgagggaggaaggctg
18403   tgagctgcagctagccagag  gggtctcccagaagaatggg  gagagctaagaaggaaagtt  gaggtcacagtgggaaggag
18483   accagacaaagggttggaa  ggtaggtaaaatgcagctcgt  gtattcttgggagccttagg  ccttgggcaagagggtagaa
18563   gaggtgtttgtcctggctg  cagtcctgtatcagctctgg  tgtcttggccacgctcaca  gcaggatccccttccagatt
18643   cccgagaatttctcacagtt  cagagagcacgctacttgta  ggcaggtgaggcttgcaaagg  acagcttttctgcctaatt
18723   ttcaaagtgagttcagcctt  tgctaggtcacctttgggt  ctcagaaggcttcagctcct  ggtagagcatgaatcacgtc
18803   aggcgtgatgctgagacct   ctcctacccctgacaccccaa  acccccacctctgaccctgc  agTGCTTTGCCAGATACTT
                                                                                        lyAlaLeuProAspThrL
```

FIG. 2J

18883  TGTCAGGGCAGAGACACCTTCC ACTTGGAAGGAGACGTGTGGCT GTTGACAGCCAGCCCACAG CTCCAGAGCCCACCAGCAGC
       euSerArgGlnThrProSer ThrTrpLysAspValTrpLe uLeuThrAlaThrProThrA laProGluProThrSerSer

19963  AACACCGAGACTGCTTTTAC CTCTGTCCTGCCAGCCGGAG AGAAGCCCGAGGAGGAGAG CCTGTGCTCCATGTAGAAGC
       AsnThrGluThrAlaPheTh rSerValLeuProAlaGlyG luLysProGluGluGluGlu ProValLeuHisValGluAl

19043  AGAGCCTGGCTTCACTGCTC GGGACAAGGAAAAGGAGGTC ACCACCAGGCCCAGGGAGAC CGTGCAGCTCCCCATCACCC
       aGluProGlyPheThrAlaA rgAspLysGluLysGluVal ThrThrArgProArgGluTh rValGlnLeuProIleThrG

19123  AACGGGCCTCAACAGTCAGA GTCACCACACAGCCAGGCAGC TGTCACATCTCATCCGCACG GGGGCATGCAACCTGGCCTC
       lnArgAlaSerThrValArg ValThrThrAlaGlnAlaAl aValThrSerHisProHisG lyGlyMetGlnProGlyLeu

19203  CATGAGACCTCGGCTCCCAC AGCACCTGGTCAACCTGACC ATCAGCCTCCACGTGTGGAG GGTGGCGGGCACTTCTGTCAT
       HisGluThrSerAlaProTh rAlaProGlyGlnProAspH isGlnProProArgValGlu GlyGlyGlyThrSerValIl

19283  CAAAGAGGTTGTCGAGGATG GAACTGCCAATCAGCTTCCC GCAGGAGAGAGGGCTCGAGA ACAAgtgagtggctttgcat
       eLysGluValValGluAspG lyThrAlaAsnGlnLeuPro AlaGlyGluGlySerGlyGl uGln 19363  ttcctgggtggccactagtg cctgcacctggccgcctaat gtcctcattacagtgacagg tgacagggtccacttcct
19443  cctgccgaaacagactgat tgcaagatcaggaggtgggc gactccttagatgtcattca ggagcttacagcagggtgaa
19523  ttttccgtcttagaccttca tgggaattttcacacaacaa tgtgtacgttgtgtcactgg aggcggtatctgtgtcttgg
19603  cctgccaggtcccagtgt gactgactgcattccttgac agatgctggtataggttggc tacgtctgatggggtggca
19683  ggggatcccatcaggtatgg cactgctcaggttgctgttg tgtcagtggctccagctgac ctgatcccaacctaccctc
19763  tgtagGACTTCACCTTTGAA ACATCTGGGGAGAACACAGC TGTGGCTGCCGTAGAGCCCG GCCTGCGGAATCAGCCCCG
       AspPheThrPheGlu ThrSerGlyGluAsnThrAl aValAlaAlaValGluPro GlyLeuArgAsnGlnProPro 19843  GTGGACGAAGGAGGCCACAGG TGCTTCTCAGAGCCTTTGG ACAGGAAGGAAGTGCTGGA Ggtgagtcttctttcaggtg
       ValAspGluGlyAlaThrGl yAlaSerGlnSerLeuLeuA spArgLysGluValLeuGly G

FIG.2K

```
20923         gagagaggaggcaggtggt ggctctgaggtagcctggt tgctggggtgaagcatcttt agcagcaggtggggaagga
20003         ggagggtcaattctactcca ggccacctcctaggctgtcc gtctagtctgggagagacta ccactgacccgtggagcta
20083         ctgatctgagcctgcctctg ttcactccctagGTGTCATT GCCGGAGGCTAGTGGGCCT CATCTTTGCTGTGTGCCTGG
                                                     lyValIle AlaGlyGlyLeuValGlyLe uIlePheAlaValCysLeuV 20163         TGGCTTTCATGCTGTACCGG ATGAAGAAGAAGGACGAAGG CAGCTACTCCTTGGAGGAGC CCAAACAAGCCAATGCGGT
              alAlaPheMetLeuTyrArg MetLysLysLysAspGluGl ySerTyrSerLeuGluGluP roLysGlnAlaAsnGlyGly 20243         GCCTACCAGAAACCCACCAA GCAGGAGGAGTTCTACGCCT gatgggaaatagttcttc tccccccacagccctgcca
              AlaTyrGlnLysProThrLy sGlnGluGluPheTyrAla 20323         CTCACTAGGCTCCCACTTGC CTCTTCTGTGAAAAACTTCA AGCCCTGGCCTCCCCACCAC TGGGTCATGTCTCTCTGCACC
20403         CAGGCCCTTCCAGCTGTTCC TGCCCGAGCGGTCCCAGGGT GTGCTGGGAACTGATTCCCC TCCTTTGACTTCTGCCTAGA
20483         AGCTTGGGTGCAAAGGGTTT CTTGCATCTGATCTTTCTAC CACAACCACACCTGTTGTCC ACTCTTCTGACTTGGTTCT
20563         CCAAATGGGAGCAGGAGACCCAG CTCTGGACAGAAAAGGGACC CGACTCTTTGGACCTAGATG GCCTATTGCGGCTGGAGGAT
20643         CCTGAGGACAGGAGAGAGGGC TTCGGCTGACCAGCCATAGC ACTTACCCATAGAGACGCT AGGTTGGCCGTGCTGTGGTG
20723         GGGGATGGAGGCCTGAGCTC CTTGGAATCCACTTTCATT GTGGGAGGTCTACTTTAGA CAACTTGGTTTGCACATAT
20803         TTTCTCTAATTCTCTGTTC AGAGCCCCAGCAGACCTTAT TACTGGGTAAGGCAAGTCT GTTGACTGGTGTCCCTCACC
20883         TGGCTTCCCTAATCTACATT CAGGAGACGAATCGGGGGT TAATAAGACTTTTTTGTTT TTTGTTTTTGTTTTTAACCT
21963         AGAAGAACCAAATCTGGACG GCAAAACGTAGGCTTAGTT GTGTGTTGTCTCTGAGTTTG TCGCTCATGCGGTACAACAGG
21043         GTATGGACTATCTGTATGGT GCCCCATTTTTGGCGGCCCG TAAGTAGGCTGGCTAGTCCA GGATACTGTGGAATAGCCAC
21123         CTCTTGACCAGTCATGCCTG TGTGCATGGACTCAGGGCCA CGGCCTTGCCCTGGGCCACC GTGACATTGGAAGAGAGCCTGT
21203         GTGAGAACTTACTGCAAGTT CACAGTCTAGGAGTGGAGGG GAGAGACTGTAGAGTTTTG GGGGAGGGTGGCAAGGGTG
21283         CCCAAGCGTCTCCCACCTTT GGTACCATCTCTAGTCATCC TTCCTCCCGGAAGTTGACAA GACACATCTTGAGTATGGCT
21363         GGCACTGGTTCCTCCATCAA GAACCAAGTTCACCTTCAGC TCCTGTGGCCCCGCCCCAG GCTGGAGTCAGAAATGTTTC
21443         CCAAAGAGTGAGTCTTTTGC TTTTGGCAAAACGCTACTTA ATCCAATGGGTTCTGTACAG TAGATTTGCAGATGTAATA
21523         AACTTTAATATATAAAGGAGTC CTATGAACTCTACTGCTTCT GCTTCTTCTTCTCTGGACTG GTGGTATAGATATAGCCACC
21603         CTTTGCCCAAACCCTGGTAG CTCGGGAAGCTTGGCTTAA GGCTGCACGCCTCCAATCCC CCAAAGGTAGGATCCTGCT
21683         GGGTCCAGGGTTCCTCTGAT TTATTTGGTTTTGTTGTGT GTGTTGGTTTTCTTTTGG CTAAACTTCTTTTGGAAGTT
21763         GGTAAGTTCAGCCAAGGTTT TACAGGCCCTGATGTCTGTT CTTCTAAATGGTTTAAGTAA TTGGGACTCTAGCACATCTT
21843         GACCTAGGGTCACTAGAGCT AAGCTTGCTTGCAGGGCAG ACACCTGGGACAGCCTTCCT CCCTCATGTTGCTGGGACA
```

FIG.2L

```
22923  CTGCTGAGCACCCCTTGCTT  ACTTAGCTCAGTGATGTTCC  AGCTCCTGGCTAGGCTGCTC  AGCCACTCAGCTAGACAAAA
22003  GATCTGTGCCCTGTGTTTCA  TCCCAGAGCTTGTTGCCAGA  TCACATGGCTGGATGTGATG  TGGGGTGGGGGTGGGGTCAT
22083  ATCTGAGACAGCCCTCAGCT  GAGGGCTTGTGGGACAGTGT  CAAGCCTCAGGCTGGCGCTC  ATTCATATAATTGCAATAAA
22163  tgtacgtgtccatttggac   agcagacactttggtgtact  tgtgcagtctcttttggtc   tggaccatgtccaactctat
22243  ctggtttttggaatgggagc  ctaactgcctgtgttctgg   cttggtaccaaatagcaaca  gtcagtggcatccttgccca
22323  ggcccagggcaggactatg   ctcttgccatatccaggact  cccgactttgcacctgtttt  ccctctgtgtagcatcat
22403  gaactccagctaggttgttc  ctttccctggggtcaggagg  attctgctgactctgaatgt  caggatttgcttttgttctg
22483  tttgcttattgggcaattct  caaccttcactagcaacagt  ctcatgtgtcaggattacaa  gtattgcttgcacattgagg
```

FIG.2M

☐ ECTODOMAIN  ▨ TRANSMEMBRANE DOMAIN
▦ CYTOPLASMIC DOMAIN

ECTO 15   ECTO 34   ECTO 2   ECTO 23

SUPPRESSION OF TUMOR CELL GROWTH BY SYNDECAN-1 ECTODOMAIN

CROSS REFERENCE TO RELATED APPLICATIONS

This application is a continuation-in-part of U.S. application Ser. No. 08/258,862, filed Jun. 13, 1994, now abandoned, the contents of which is incorporated herein by reference.

FIELD OF THE INVENTION

This invention is in the field of cancer biology and therapy. Specifically, the invention is to a method for slowing or normalizing the growth rate of a cell, especially a malignant cell, by providing efficacious amounts of the ectodomain part of syndecan-1 to such cell. The method of the invention facilitates and results in the normalization of the growth rate and differentiation state of malignant cells.

BACKGROUND OF THE INVENTION

Cellular differentiation is based on selective use of genetic information programmed by extracellular stimuli, which for example could include cellular interactions and binding of extracellular effector molecules by cell surface receptors. It is becoming more evident that cell surface proteoglycans play an important role in the regulation of cell behavior. Syndecans are cell surface proteoglycans, which have been shown to participate in both matrix recognition and growth factor binding and thus believed to participate in cell regulation. The sequences of human, mouse, rat and hamster syndecans are known. Syndecans have recently been reviewed (Jalkanen, et al., in *Receptors for Extracellular Matrix*, J. MacDonald & R. Mecham, Editors, Academic Press, San Diego, pp. 1–37 (1991) and Bernfield, O., et al., *Annu. Rev. Cell Biol.* 8:365–393 (1992)).

Syndecan-1 is the best characterized cell surface proteoglycan (Saunders et al, *J. Cell Biol.* 108:1547–1556 (1989); Mali et al., *J. Biol. Chem.* 265:6884–6889 (1990)). International patent application WO 90/12033 discloses the amino acid sequence and corresponding cDNA sequence of mouse syndecan-1 molecule. A diagnostic method for detecting transformed cells by detecting changes is the syndecan expression in transformed cells is described in International Patent Application WO 92/13274 and WO 93/05167.

The enhancer element of the syndecan gene as well as a method of decreasing the growth of malignant cells by inducing the expression of syndecan within malignant cells is described in International Patent Application (PCT/FI93/00514)

BRIEF DESCRIPTION OF THE DRAWINGS

FIGS. 1A and 1B [SEQ ID NO:3:] is the sequence of human syndecan-1. Circles: possible GAG attachment sites; bold underline: transmembrane domain; light underlining: aataa polyadenylation signal.

FIGS. 2A–2M [SEQ ID NO:5:] is the sequence of mouse syndecan-1.

SUMMARY OF THE INVENTION

Figure 3:
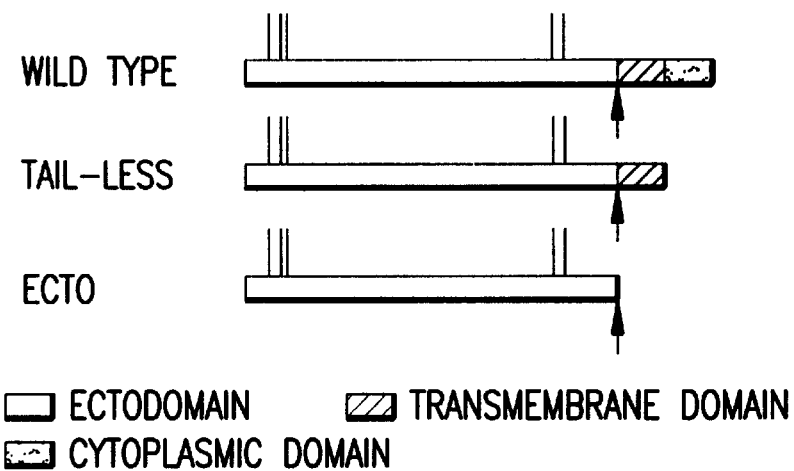
FIG. 3 Schematized structure of the core proteins of wild type, tail-less and ecto transfection constructs. The wild type construct contains the full length mouse syndecan-1 ectodomain (Mali, M. et al., *J. Biol. Chem.* 268:24215 (1993)). The tail-less construct was generated using oligonucleotide-directed mutagenesis resulting a deletion mutant with single arginine residue in the cytoplasmic domain as described in the examples (Miettinen, H. M. et al., *J. Cell Sci.* in press (1994)). The ecto construct was also derived by oligonucleotide-directed mutagenesis as described in the examples, and has a stop codon in the protease sensitive site just adjacent to the cell surface. Vertical lines indicate putative GAG attachment sites and arrows the dibasic protease sensitive site.

The present invention is first directed to a pharmaceutically acceptable composition containing syndecan ectodomain.

The invention is further directed to a method for decreasing or normalizing tumor cell growth by providing such syndecan ectodomain protein to a tumor cell, in the cell's extracellular environment.

The methods of the inventions are useful with both malignant and non-malignant tumor cells, and are especially useful with tumors characterized by loss of syndecan-1, such as gliomas, myelomas, carcinomas, sarcomas, lymphomas or adenomas.

Definitions

In order to provide a clearer and more consistent understanding of the specification and claims, including the scope to be given such terms, the following definitions are provided.

Cell growth. By "cell growth" is meant cell replication, or the rate of cell division, both controlled and uncontrolled. Therefore, cell growth is the rate of division and replication.

Malignant. By "malignant" is meant uncontrolled cell growth.

More Differentiated Phenotype. In stating that a cell has a "more differentiated phenotype" is meant that the cell possesses a phenotype usually possessed by a certain cell type more differentiated than the cell. A phenotype can be defined by one or more phenotypic characteristics. For example, an epithelial cell shape is a more differentiated phenotype of a mesenchymal-like shape; therefore, in this example, the "more differentiated phenotype" is the epithelial cell morphology, rather than a mesenchymal-like shape. A terminally differentiated mesenchymal cell is a "more differentiated phenotype" than a condensing mesenchymal cell. The state of the actin-containing cytoskeleton can also be used; disorganized actin filaments are indicators of a less differentiated phenotype than organized filaments.

Efficacious Amount. An "efficacious amount" of an agent is an amount of such agent that is sufficient to bring about a desired result, especially upon administration of such agent to an animal or human. An efficacious amount of syndecan-1 ectodomain in the compositions and methods of the invention is the amount sufficient to reduce tumor cell growth, preferably to normal growth rates for the specific cell types.

Administration. The term "administration" is meant to include introduction of the syndecan ectodomain according to the invention into an animal or human by any appropriate means known to the medical art, including, but not limited to, injection, oral, enteral, transdermal and parenteral (e.g., intravenous) administration.

Exposure to syndecan ectodomain. By "exposing" a cell to syndecan ectodomain in the compositions of the invention is meant that the external milieu of the cell is provided with amounts of syndecan ectodomain that are efficacious in promoting the desired effect, generally a lowered growth rate of a tumor cell.

Pharmaceutically Acceptable Salt. The term "pharmaceutically acceptable salt" is intended to include salts of the syndecan ectodomain of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

Pharmaceutically Acceptable Composition. The term "pharmaceutically acceptable composition" is intended to include solvents, carriers, diluents, and the like, which are utilized as additives or vehicles to preparations of the syndecan ectodomain of the invention so as to provide a carrier or adjuvant for the administration of such compounds to patients (human or animal) in need of the same. Such additives can perform certain functions, such as, for example, provide the proper ionic conditions for administration, stabilize the syndecan ectodomain against inactivation or degradation, and/or increase the half-life of the syndecan ectodomain. A pharmaceutically acceptable composition is medically compatible with the host to which it is being administered.

Treatment. The term "treatment" or "treating" is intended to include the administration of the pharmaceutically acceptable compositions of the invention comprising efficacious amounts of syndecan ectodomain of the invention to a patient for purposes which may include prophylaxis, amelioration, prevention or cure of a medical disorder, including the suppression of tumor growth.

Substantially Free of Natural Contaminants. A material is said to be "substantially free of natural contaminants" if it has been substantially purified from materials with which it is normally and naturally found before such purification and those contaminants normally and naturally found with the substance in vivo or in vitro are substantially absent from the final preparation of the material. When administered to a subject in need of treatment, the syndecan ectodomain of the invention is substantially free of natural contaminants which associate with the syndecan ectodomain either in vivo (in the host from which the ectodomain was isolated), or in vitro (as a result of a chemical synthesis). By "substantially absent" is meant that such contaminants are either completely absent or are present at such low concentrations that their presence (1) does not interfere with the desired therapeutic effect of the active agent (herein the ability of the syndecan ectodomain to inhibit tumor growth) in the therapeutically acceptable composition when such composition is administered to a patient in need of same and (2) does not harm the patient as the result of the administration of such composition.

DETAILED DESCRIPTION OF THE PREFERRED EMBODIMENTS

The invention is the discovery that the ectodomains of the syndecans possess certain biological functions and are capable of providing such functions to cells when presented to the external surface of a cell other than the cell that synthesized such syndecan ectodomain. Syndecans are membrane bound proteins. It was surprisingly found that extracellularly-provided syndecan ectodomain, by itself, is sufficient to restore a more differentiated morphology to tumor cells and to suppress the growth of malignant cells. The invention herein is exemplified with syndecan-1.

All syndecans contain a cytoplasmic domain, a transmembrane domain and an extracellular domain. The extracellular domain is the ectodomain. As discussed by Jalkanen, et al., in *Receptors for Extracellular Matrix*, J. MacDonald & R. Mecham, Editors, Academic Press, San Diego, pp. 1–37 (1991)), the syndecans show highly conserved homologous sequences at three separate regions of their ectodomains. A dibasic sequence is immediately adjacent to the N-terminal end of the hydrophobic transmembrane domain, suggesting that it is located next to the outer leaflet of the plasma membrane, and may serve as a protease-susceptible site, which enables the ectodomain to be cleaved intact from the cell surface.

The core protein of human syndecan-1 contains 310 amino acid residues. There is a high degree of structural and functional homology between mouse and human syndecan-1. Human syndecan-1 has an identical size, charge, buoyant density and GAG composition to that of mouse syndecan-1. Human syndecan-1 ectodomain, like that of the mouse, binds to type I collagen fibrils and fibronectin but not to laminin or virtronectin.

The sequence of human syndecan-1 is known and it has been cloned (Mali et al., J. Biol. Chem. 265:6884–6889 (1990)). When numbered according to FIG. 2 in Mali et al., J. Biol. Chem. 265:6884–6889 (1990), amino acids 1 to 251 are the ectodomain of human syndecan-1 (with the secretion-signal attached), the hydrophobic membrane-spanning domain contains the next 25 amino acid residues (amino acids 252–276), and the cytoplasmic domain contains the last 34 amino acid residues (amino acids 277–310).

The signal peptide sequence is the first 17 amino acids of the ectodomain. Although useful to promote secretion of syndecan-1 from a cell synthesizing the same, the secretion signal is not necessary for the tumor growth suppression or differentiation functions of the ectodomain of the invention.

Therefore, the sequence of the ectodomain of the invention included those fragments of syndecan amino acid residues 1–251 that retain the GAG attachments sites and desired function of the ectodomain, such as, for example, ectodomains having amino acids 1–251 (with secretion signal and cleaved at the RK site), 18–231 (minus secretion signal but cleaved at the RK site), 1–231 (with secretion signal but cleaved at the RR site) and 18–251 (minus secretion signal but cleaved at the RR site). An ectodomain having a carboxy terminal at a site anywhere between amino acid residues 231–251, or a secretion signal fragment of less than amino acids 1–17 is also useful since those embodiments would be expected to retain the biological properties of the ectodomain.

Although the human and mouse ectodomains are only 70% identical at the amino acid level, all putative glycosaminoglycan (GAG) attachments sites are identical between the mouse and human sequences. The five possible glycosaminoglycan attachment sites of human syndecan ectodomain are at positions 37, 45, 47, 206 and 216. Two of these sites belong to the consensus sequence SGXG [SEQ ID NO:7:] and three others to (E/D)GSG(E/D) [SEQ ID NO:8:]. Also identical between mouse and human syndecan are the single site for N-glycosylation and the proteinase-sensitive dibasic RK site adjacent to the extracellular face of the transmembrane domain. Human syndecan also contains a second dibasic RR sequence just 18 residues apart from the RK sequence. Proteolytic cleavage at this site would also release an ectodomain of the invention that contained all GAG sites intact.

The transmembrane domains of human and mouse syndecan-1 are 96% identical (the only change in human syndecan is an alteration of an alanine to a glycine) and the cytoplasmic domains are 100% identical in mouse and human syndecan.

Syndecan ectodomain, such as human syndecan ectodomain, can be produced by recombinant techniques in any desired host. However, it is preferable, but not necessary, to utilize a host that is of a similar cell type to that of the tumor, so as to provide as similar GAG composition as possible, to that of the cell in its non-tumor state. Many deposited cell lines that are human tissue specific or characteristic of different cell types are available.

For example, the mouse syndecan-1 clones of the invention were constructed using liposome transfection and geneticin to subsequent select stably transfected cells clones. S115 cell line clones (see FIG. 3) expressing either the wild type mouse syndecan-1 (wild type), a deletion mutant with a single arginine residue in the cytoplasmic domain only (tail-less) or the plain ectodomain of syndecan-1 (ecto). Wild type syndecan-1 and cytoplasmic deletion mutant (tail-less) were cloned into EcoRI site of the pBGS eucaryotic expression vector. The ectodomain construct was cloned into pMAMneo vector, in order to obtain efficient expression levels also in the presence of hormone since the MMT LTR promoter is induced by the same steroid hormone as the cells. It is not necessary to use this vector as many such expression vectors are known in the art. Syndecan-1 expression at the cell surfaces was detected using a monoclonal antibody, exemplified using previously described mAb 281-2, that recognizes the ectodomain of mouse syndecan-1 core protein, and actin filaments were visualized using rhodamine-conjugated phalloidin, as an indication of the differentiation state and growth state of the cell.

Without testosterone, S115 cells exhibit organized actin filaments typical to these cells when epithelioidal. In the presence of testosterone, actin was disorganized and globular, and the cell surface expression of syndecan-1 was also suppressed. Wild type and Tail-less clones expressing syndecan-1 at the cell surfaces restored actin filament organization in spite of the testosterone treatment. Because transfection of Tail-less mutant also induced similar changes as the Wild type syndecan-1, S115 cells were transfected with the plain ectodomain and more than 50 independent clones secreting different levels of the ectodomain into the culture medium were produced. The cell surfaces of these cells stained only faintly for syndecan-1 but still these cells revealed well organized actin filaments and an epithelioid morphology. These results indicate that ectodomain of syndecan-1 is sufficient enough to restore epithelioid morphology of testosterone treated S115 cells to that of the more differentiated phenotype and is a useful anti-cancer drug.

In non-tumor cells, syndecan is expressed in epithelial cells, mesenchymal cells, pre-B cells and plasma cells, but not by B cells. Syndecan is also expressed in tissues that contains cells of this type, including human brain tissue. Therefore the methods of the invention are especially useful against tumors of the epithelial, mesenchymal, pre-B and plasma cells. Most especially, the methods of the invention are useful in slowing the growth of steroid responsive tumors, especially estrogen or androgen responsive tumors (tumors that grow better in the presence of steroids, estrogen, or androgens as indicated) including breast cell tumors, endometrium cell tumors, and tumors of the prostate cells.

For treatment of humans and animals, syndecan-1 ectodomain is administered in a pharmaceutically acceptable solution at levels sufficient to restore the normal growth state of tumor, or malignant cells, as evidenced by a slower growth rate. The syndecan-containing pharmaceutically acceptable solution can be administered in any form that effects prophylactic, palliative, preventative or regressive tumor growth.

The amount of the syndecan ectodomain-1 compositions of the invention that is administered to the patient, and the duration of such administration, can be determined by monitoring tumor growth in the patient during the course of the administration, and adjusted according to the response of the patient. The syndecan ectodomain of the invention is preferably provided to the target tumor cell at extracellular concentrations about 0.7 nM–1 nM (see FIG. 11), but any concentration sufficient to decrease growth of the tumor may be used. The ectodomain can be provided either locally (as with a concentrated delivery right to the targeted organ) or systemically (such as delivery through the blood stream). The dose of syndecan given to the patient (either human or animal) will therefore take into account the volume (such as blood volume) into which the ectodomain is being administered, and the type of tumor that is being targeted. For example, if a continuous exposure to the syndecan ectodomain is necessary, then more frequent dosages will be required than if only a transient exposure of the tumor to the syndecan ectodomain is necessary. For example, a 1 nM amount of syndecan ectodomain having amino acids 1–251 corresponds to 0.2 mg/lL (200 $\mu$g/L), either in the blood or locally concentrated at the site of action. Typical systemic doses of syndecan ectodomain useful in the methods of the invention for treatment of humans or animals include amounts that provide a final blood concentration of most preferably 0.2 mg syndecan ectodomain per liter blood. Blood volume in humans is 6% of the body weight, hence a 70 Kg person has about 4.2 liters of blood. However, because the effects of the syndecan ectodomain are presumably local (e.g. acting at a specific cell membrane), sequestered or kinetically determined, the theoretically minimum dose can be adjusted upward in order to achieve favorable therapeutic effects.

Syndecan ectodomain may be administered by any route that delivers efficacious levels of the drug to the desired active site, for example, by injection. For parenteral administration, preparations containing the syndecan ectodomain may be provided to a patient in need of such treatment in combination with pharmaceutically acceptable sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The syndecan ectodomain containing medicament (the pharmaceutically acceptable solution containing the therapeutically active syndecan-1 ectodomain) can be administered by means of catheters or pumps, especially when it is desired to deliver the ectodomain at localized high concentrations. The syndecan-1 ectodomain-containing medicament can be administered subcutaneously or directly into soft tissue by means of implantation devices inert to body fluids. Such devices and implantation systems are known in the art. A ceramic system for delivery proteins is described, for example, in WO 92/00109.

The syndecan-1 ectodomain containing medicament can be administered by providing such molecule as a part of a chimeric molecule (or complex) which is designed to target specific organs, for example, as part of an antibody that recognizes determinants on the target tissue or organ or cell, in its tumor or non-tumor state.

The pharmaceutically acceptable solution containing the syndecan-1 ectodomain can be administered topically. Although syndecan-1 ectodomain can be administered to a patient in a regime that includes other cancer fighting drugs, optimal administration of the syndecan-containing compositions of the invention are especially useful in this regard.

Topical administration is preferably accomplished in one of two ways. First, the therapeutically active syndecan ectodomain can be mixed with suitable pharmaceutically acceptable carriers and (optionally), penetration enhancers to assist in the delivery of the active agent across the skin, to form ointments, emulsions, lotions, solutions, creams, gels or the like, and the preparation itself is then applied to a certain area of skin. Alternatively, the therapeutically active syndecan ectodomain can be incorporated into a patch or transdermal delivery system according to known technology for the preparation of such patches and delivery systems.

Administration in a sustained-release form is more convenient for the patient when repeated injections for prolonged periods of time are needed, or when continuous exposure of the tumor cell to the ectodomain is desired. In intravenous dosage forms the compositions of the present invention have a sufficiently rapid onset of action to be useful in the acute management of tumor growth.

Administration may be localized directly to the cell if the cell is associated with a tissue or bodily organ, or administration can be systemic, in a medium in which the cell is found, such as the blood or cerebrospinal fluid. Systemic administration throughout the patient's body, for example, by administration to the bloodstream, facilitates treating patients for whom tumor cells may be at more than one site in the body.

Providing syndecan ectodomain as the product of a syndecan ectodomain expression construct that secretes ectodomain in efficacious amounts is also considered "administration." For example, administration across the blood brain barrier can be achieved by utilizing known viral vector systems to deliver syndecan ectodomain DNA in a manner that expresses ectodomain and secretes it to the extracellular environment, such as, for example, in the retroviral systems described in WO 93/03743, WO90/09441, Breakefield, X.A. et al., *The New Biologist* 3:203–218 (1991) and Huang, Q. et al., *Exp. Neurol.* 115:303–316 (1992).

The pharmaceutically acceptable composition of the invention, containing the syndecan-1 ectodomain can be manufactured in a manner which is in itself known, for example, by means of conventional mixing, dissolving, lyophilizing or similar processes. The compositions of the present invention that provide the syndecan-1 ectodomain find utility in their ability to slow or prevent tumor growth or tumor reappearance, and in their ability to alter the phenotype of the cell to that a more differentiated state, in both human and animal patients. The syndecan-1 ectodomain compositions of the invention utilize the body's own mechanisms for promoting differentiation of specific cell types to its maximum potential.

The compositions and methods of the invention are not meant to be limited to syndecan-1. Syndecan-1, syndecan-2, syndecan-3 and syndecan-4 are known to contain similar domain structures. It is known that differentiation of certain cell types is associated with the loss of syndecan-1 but with the appearance of another member of the syndecan family (Bernfield, O., et al., *Annu. Rev. Cell Biol.* 8:365–393 (1992)). For example, when bronchial epithelia form buds, lung mesenchyme loses syndecan-1 but acquires syndecan-2. In tumors from cell types that lose syndecan-1 upon differentiation but express a different syndecan, utilization of the ectodomain from the syndecan that is expressed in the differentiated state would be indicated.

The examples below are for illustrative purposes only and are not deemed to limit the scope of the invention.

EXAMPLES

The following examples are intended to illustrate, but not to limit the invention.

Example 1
Deletion mutant syndecan constructs

Using liposome transfection and subsequent selection of stably transfected cells clones by geneticin as described by Leppä et al., Proc. Natl. Acad. Sci. U.S.A. 89: 932 (1992), S115 cell line clones (see FIG. 3) were produced that expressed either the wild type mouse syndecan-1 (Wild type), a deletion mutant with a single arginine residue in the cytoplasmic domain only (Tail-less) or only the ectodomain of syndecan-1 (Ecto 2; see FIG. 3). These three forms and the hosts were constructed as follows.

The full-length mouse syndecan-1 cDNA, as described in Mali et al., J. Biol. Chem. 268:24215–24222 (1993) was cloned into the EcoRI site of Bluescript SK$^+$ (Promega).

1) The EcoRI insert of the Bluescript construct was cloned into the EcoRI site of the pBGS vector (Mali et al., J. Biol. Chem. 268:24215–24222 (1993)) and the orientation was confirmed. This construct was designated "Wild-type."

2) A mutagenic 25-base oligonucleotide having the sequence: 5'G CTG TAC CGC TAG CAG AAG AAG GAC-3' [SEQ ID No:1:], containing a stop codon and a NheI restriction site (underlined) was used to convert the codon for the second amino acid (methionine) of the cytoplasmic domain following the transmembrane domain to a stop codon. The mutation was confirmed by restriction digestion and dideoxy sequencing. The EcoRI insert of the Bluescript construct was cloned into the EcoRI site of an amplifiable pBGS vector (Mali et al., J. Biol. Chem. 268:24215–24222 (1993)). This mutant syndecan-1 containing one amino acid (arginine) in its putative cytoplasmic domain was designated "Tail-less."

A mutagenic 33-base oligonucleotide 5'-GACACCTCCCAGTACTCACTTCCTGTCCAAAAG-3' [SEQ ID NO:2:] containing a stop codon (bolded) and a ScaI site (underlined) was used to convert the first codon (E) after the dibasic protease sensitive site of the ectodomain to a stop codon. The mutation was confirmed by restriction digestion and dideoxy sequencing. This was the Bluescript-ecto construct. The EcoRI insert of the Bluescript-ecto construct was cloned into the EcoRI site of pJC119R vector (Miettinen et al., J. Cell Sci. 107: in press, (1994)). XhoI digested ecto insert from pJC119R-ecto construct was ligated into XhoI site of pMAMneo eucaryotic transfection vector, available from Clontech, Palo Alto (Leppä et al., Proc. Natl. Acad. Sci. U.S.A. 89, 932 (1992)), and the orientation was confirmed by restriction digestions.

Example 2
Expression of mutant syndecan-1 normalizes malignant growth in S115 cells Wild type syndecan-1 and cytoplasmic deletion mutant (Tail-less) were cloned into the EcoRI site of the pBGS eucaryotic expression vector (Mali et al., J. Biol. Chem. 268: 24215 (1993), but the ectodomain construct was cloned into pMAMneo vector, in order to obtain efficient expression levels also in the presence of hormone (personal communication, S. Ala-Uoti, Turku Centre for Biotechnology). The pBGS system is not repressed by testosterone. Syndecan-1 expression at the cell surfaces was detected using mAb 281-2 (Jalanen et al., J. Cell Biol. 101: 976 (1985)) that recognizes the ectodomain of mouse syndecan-1 core protein, and actin filaments were visualized using rhodamine-conjugated phalloidin.

Cells (S115+, wild type, tail-less and Ecto 2) were cultured four days on coverslips in DMEM-5% FCS-1 mM Na-pyruvate with 10 nM testosterone, except S115– cells which were cultured without testosterone in DMEM-4% DCC-FCS (Dextran-Coated-Charcoal treatment eliminates endogenous steroids from serum) with 1 mM Na-pyruvate. Cells were fixed with 0.1% Triton-X-100, 2% paraformaldehyde and incubated with rhodamine-conjugated phalloidin (Sigma). Cell surface syndecan-1 expression was visualized by incubating living cells for 1 hour on ice with rat mAb 281-2 (recognizes mouse syndecan-1 ectodomain); they were then fixed with 2% paraformaldehyde and bound mAb 281-2 was visualized using FITC-conjugated rabbit anti-rat IgG.

Without testosterone S115 cells exhibited organized actin filaments typical to these cells when epithelioidal. In the presence of hormone actin was disorganized and globular, and the cell surface expression of syndecan-1 was also suppressed as shown earlier by Leppä et al., Cell Reg. 2,1 (1991), FIG. 4.

Figure 4:
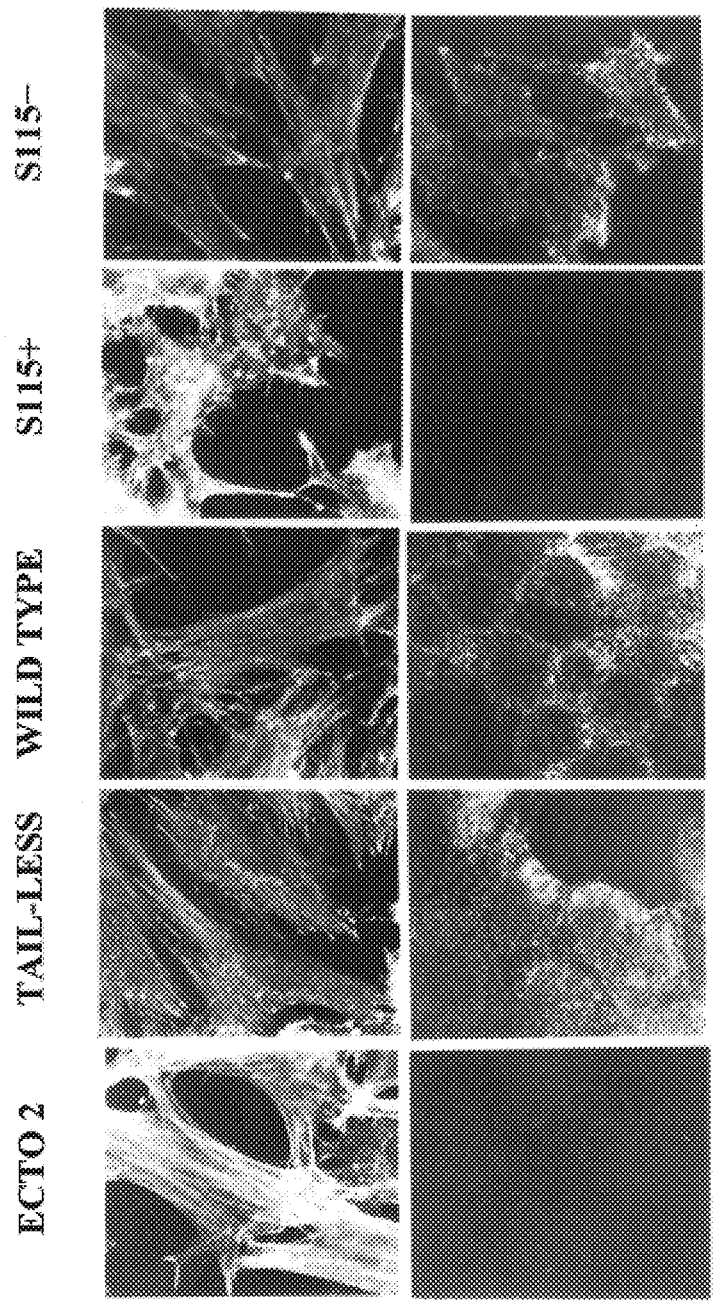
FIG. 4 Actin filament organization and immunofluorescence localization of syndecan-1 on the cell surface.

Wild type and Tail-less clones expressing syndecan-1 at the cell surfaces restored actin filament organization in spite of the testosterone treatment, FIG. 4.

Example 3
Effect of secreted syndecan-1 ectodomain on cultured S115 cells

Because transfection of the Tail-less mutant induced changes similar to those of the wild type syndecan-1, S115 cells were transfected with the ectodomain. More than 50 independent clones secreting different levels of the ectodomain into the culture medium (see FIGS. 5, 6 and 7) were produced. The cell surfaces of these cells stained only faintly for syndecan-1 but still these cells revealed well organized actin filaments and an epithelioid morphology (FIG. 4). These results suggested that ectodomain of syndecan-1 is sufficient enough to restore epithelioid morphology of testosterone treated S115 cells.

Figure 5:
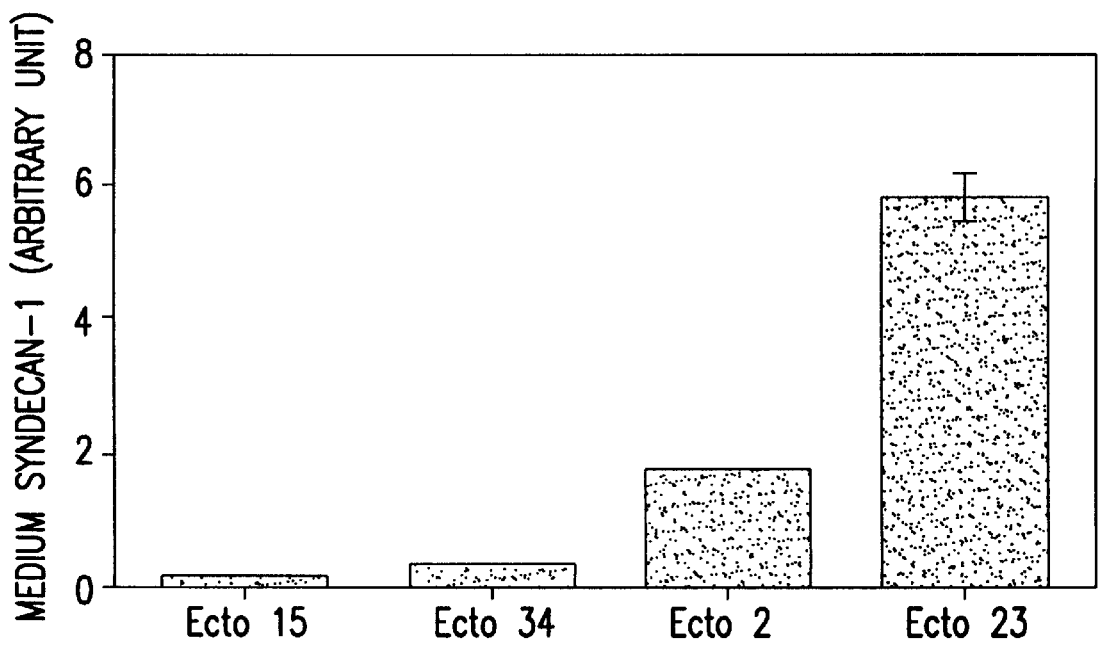
FIG. 5 Amount of secreted ectodomain of syndecan-1 from the conditioned medium of Ecto cell clones (Ecto 15, 34, 2 and 23). Cells were cultured for two days in the presence of 10 nM testosterone and the ectodomain of syndecan-1 that accumulated in the medium was used. The culture medium was used directly. Samples were normalized for cell number and equivalent amounts slot-blotted on Hybond-N+ membrane. The ectodomain of syndecan-1 was detected by enhanced chemiluminescence method using 281-2 as described in the examples (Miettinen, H. M. et al., *J. Cell Sci.* in press (1994)). Quantitations were done using computer image analysis system (Imaging Research Inc.). Means and SEMs of two parallel samples are presented.

To analyze in detail Ecto clones, amounts of secreted syndecan-1 ectodomain from the culture media were measured by enhanced chemiluminescence method using mAb 281-2 against ectodomain of syndecan-1 core protein. Two separate stably transfected cell clones secreting high amounts of syndecan-1 into the culture medium (Ecto 2 and Ecto 23) and two cell clones with low expression (Ecto 15 and Ecto 34) were selected for further analysis (FIG. 5).

Figure 6:
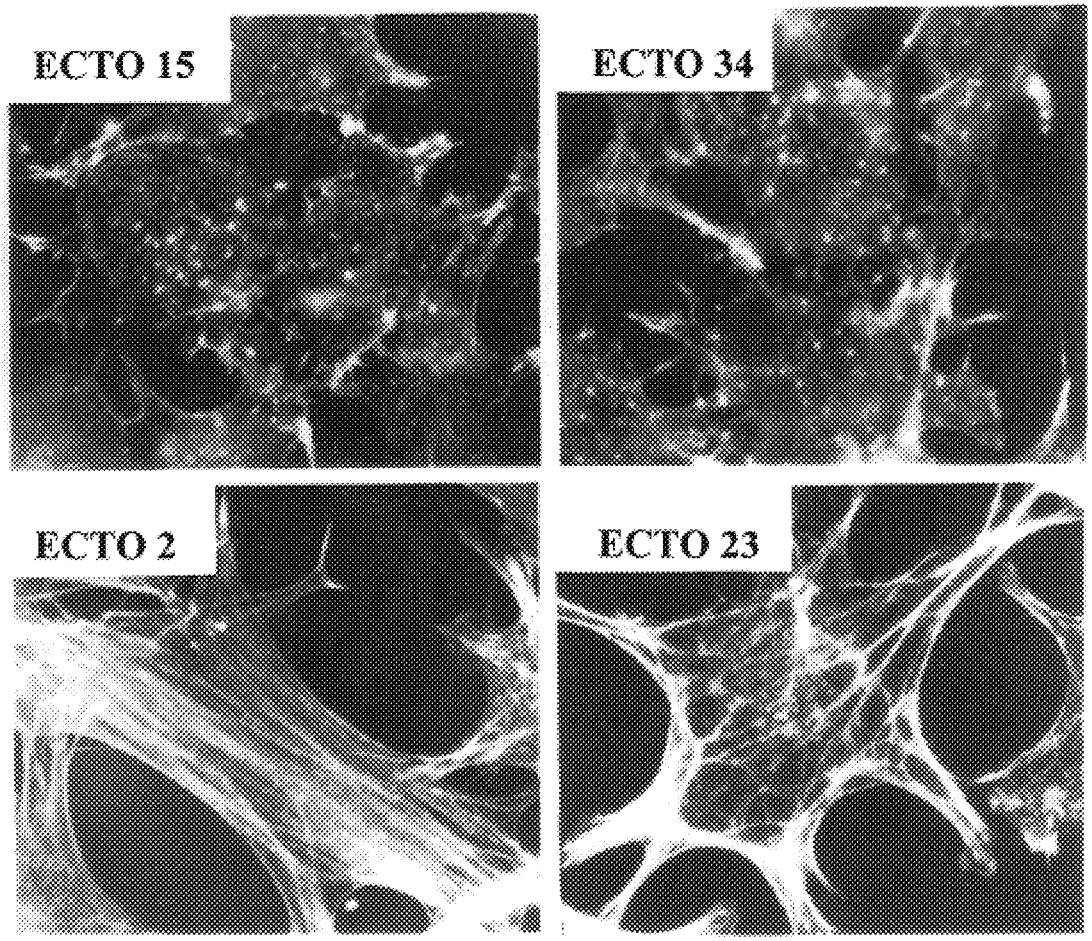
FIG. 6 Actin filament organization of Ecto cell clones. Ecto cells were cultured in the presence of 10 nM testosterone and actin filaments were visualized by rhodamine-conjugated phalloidin.
Figure 7:
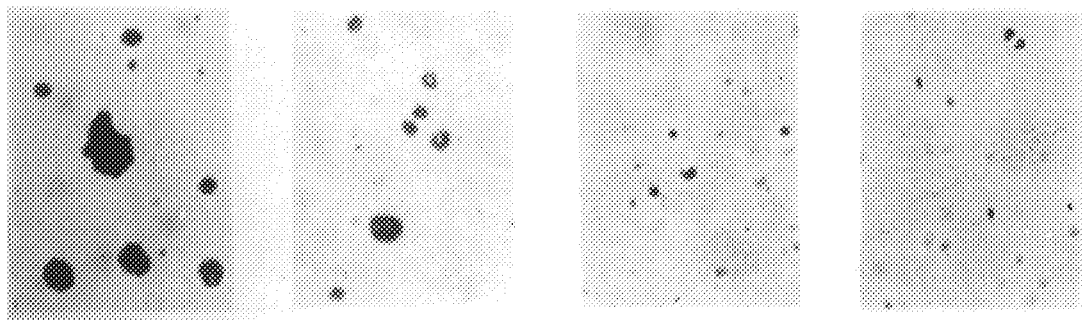
FIG. 7 Soft-agar colony formation of Ecto cell clones. Cells were cultured 12 days in 0.33% soft-agar, DMEM+5% FCS with 10 nM testosterone as described earlier (Leppä, S. et al., *Proc. Natl. Acad. Sci. USA* 89:932 (1992)).

A clear correlation between syndecan-1 ectodomain expression and reorganization of actin filaments was detected in the presence of 10 nM testosterone: Ecto 15 and Ecto 34 with low syndecan-1 expression had disorganized, mainly globular actin, but Ecto 2 and Ecto 23 clones expressing syndecan-1 ectodomain exhibited epithelioid morphology with organized actin filament bundles (FIG. 6). Enhanced expression of intact syndecan-1 has been shown previously to suppress tumor growth of testosterone-treated S115 cells (Leppä et al, supra), and now also Ecto 2 and Ecto 23 clones with high syndecan-1 ectodomain expression restricted their growth in soft-agar. The low syndecan-1 ectodomain expressing clones Ecto 15 and Ecto 34 clones, however, demonstrated soft-agar growth typical to parental S115 cells (FIG. 7). Soft agar experiment indicated that in addition to morphology, syndecan-1 ectodomain expression is sufficient to restrict also the tumorigenic growth of S115 cells.

Example 4

Isolation and purification of syndecan ectodomain from Ecto cell cultures

Because syndecan-1 ectodomain seemed to be responsible for the suppression of the malignant growth behavior of androgen treated S115 cells, we collected conditioned medium from Ecto cell cultures for ectodomain isolation. Conditioned cell culture medium was denatured with 2M urea and boiling, before loading to DEAE-sephacel column, 50 mM Na-acetate (pH=4.5) was added and medium was chilled to +4° C. The column was washed with 0.2M NaCl, 2M urea, 50 mM Na-acetate (pH=4.5), and the bound material was eluted using 1M NaCl, 2M urea, 50 mM Na-acetate (pH=4.5). Fractions containing syndecan-1 ectodomain was dialyzed against phosphate buffered saline (PBS) at 4° C. Amount of syndecan-1 ectodomain in fractions was estimated by slot-blotting and subsequent enhanced chemiluminescence method using mAb 281-2 (Example 2 and Miettinen, H. M. et al., *J. Cell Sci.* in press (1994)) and comparing the amount to the known syndecan-1 standard.

Figure 8:
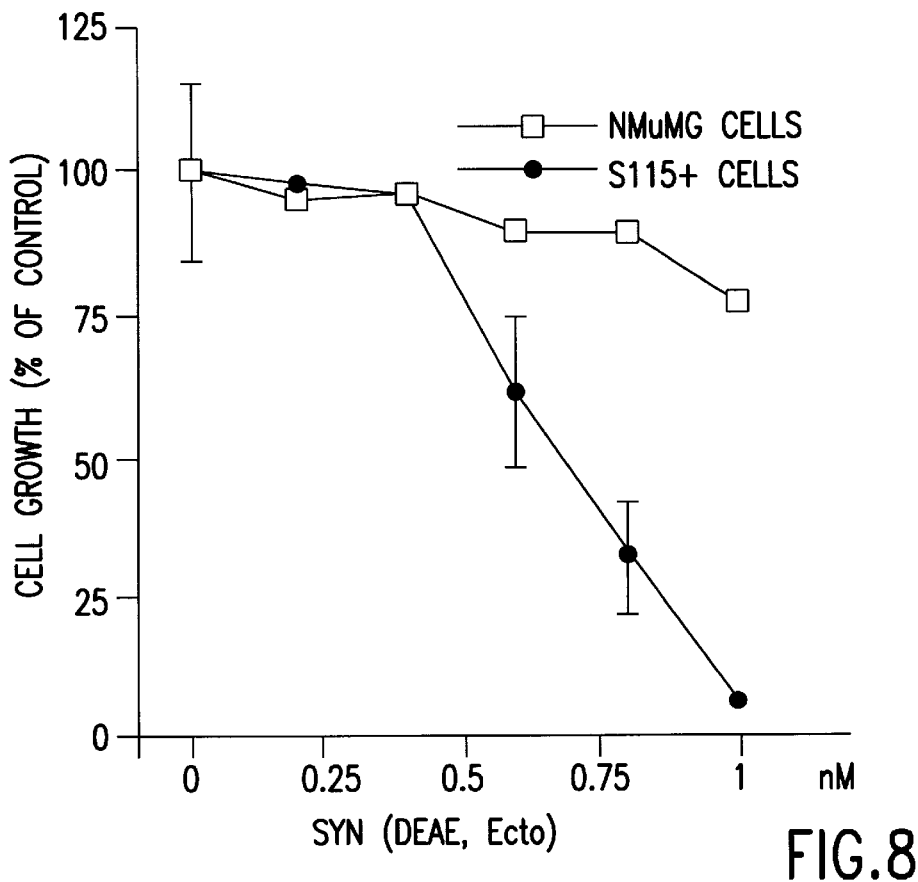
FIG. 8 The effect of DEAE-isolated syndecan-1 ectodomain (examples) from the conditioned medium of Ecto 2 cells on growth of NMuMG and testosterone treated (10 nM) S115 cells (S115+). 1500 cells were transferred into 96-well culture plates and cells were cultured with DEAE-isolated syndecan-1 ectodomain until control (without syndecan-1 ectodomain) cells reached about 75–85% confluence (NMuMG cells four days, S115+ three days). Then cells were fixed with 2% paraformaldehyde, stained with 0.5% crystal violet and washed with distilled water. Stained cells were suspended in 10% acetic acid and spectrophotometrically measured at 595 nm.
Figure 9:
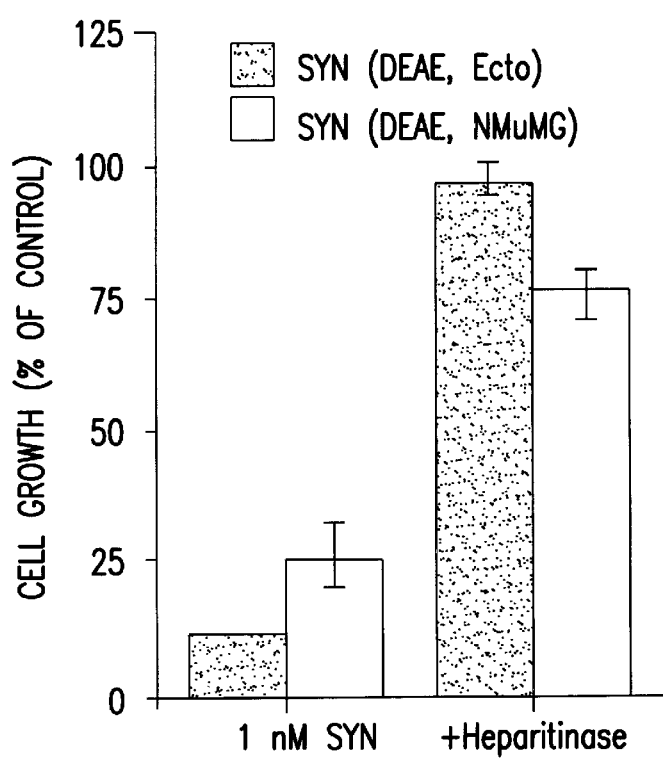
FIG. 9 The effect of heparitinase treatment of DEAE-isolated syndecan-1 ectodomain on growth inhibition of S115+ cells. S115+ cells were cultured with 1 nM DEAE-isolated syndecan-1 from cultured medium of Ecto 2 cells and from the medium of NMuMG cells, or with the same preparations pretreated with heparatinase (Seikagaku Kogyo Co.) 1 hour at 37° C.

Ectodomain of syndecan-1 from cultured medium of Ecto cells was biochemically similar to the syndecan-1 ectodomain isolated from normal murine mammary epithelial cells (NMuMG). After isolation, the syndecan-1 content of the preparate was measured and the preparate tested on hormone-treated S115 cells. As shown in FIG. 8, concentrations of the DEAE-isolated syndecan-1 ectodomain as low as 1 nM suppressed the growth of testosterone treated S115 cells (FIG. 8). The same concentration only slightly inhibited the growth of NMuMG cells, which served as normal epithelial cells (FIG. 8). Syndecan-1 ectodomain was also isolated from the culture medium of NMuMG cells, and also with this preparate, a 1 nM concentration inhibited growth of hormone-treated S115 cells (FIG. 9). Treatment of the DEAE-isolated ectodomain with heparitinase totally abolished the growth inhibitory activity of these preparates (FIG. 9), suggesting that the core protein of syndecan-1 as such was not involved.

Figure 10:
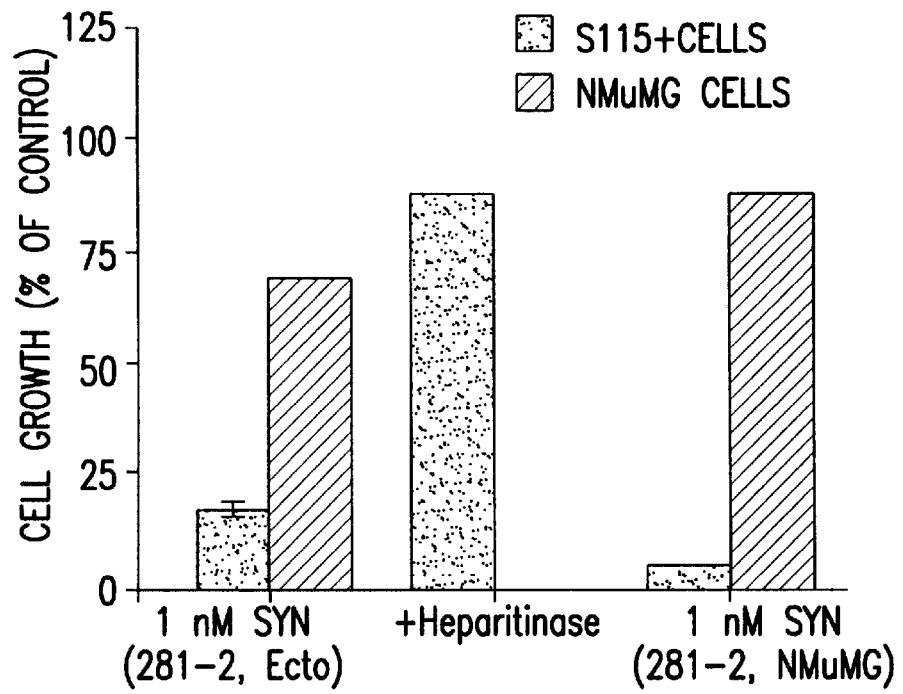
FIG. 10 The effect of immunopurified syndecan-1 ectodomain on growth of S115+ and NMuMG cells. DEAE-isolated syndecan-1 ectodomain was further purified with 281-2 immunoaffinity column (examples). S115+ and NMuMG cells were cultured with 1 nM immunoaffinity purified syndecan-1 ectodomain.
Figure 11:
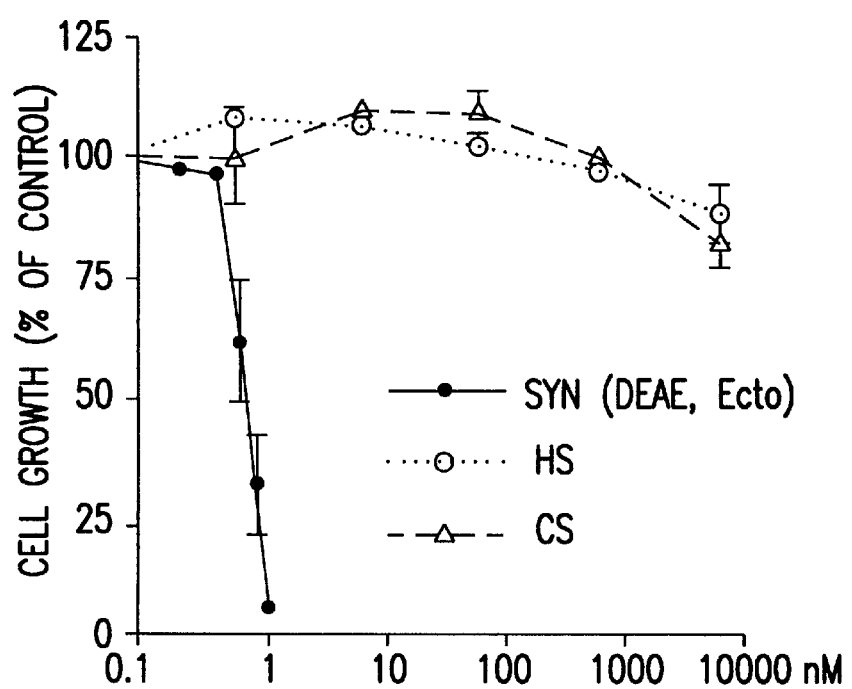
FIG. 11 DEAE-isolated syndecan-1 ectodomain but not HS or CS GAGs inhibit growth of S115+ cells.

The DEAE-isolated syndecan-1 ectodomain was further purified using a mAb 281-2 immunoaffinity column: DEAE-isolated syndecan-1 ectodomain in PBS was loaded onto a mAb 281-2-Sepharose CL-4B immunoaffinity column as described in Jalkanen et al., *J. Cell Biol.* 105: 3087 (1987), and the bound material was eluted with 50 mM triethylamine (pH=11.5). Fractions containing syndecan-1 ectodomain were dialyzed against distilled water and subsequently lyophilized. After that syndecan-1 ectodomain suspended in DMEM (Gibco) and the amount was estimated, as described above. Again, at 1 nM concentrations of this immunoafinity purified syndecan-1 ectodomain, growth inhibition of testosterone-treated S115 cells was observed and only a mild effect was evident with NMuMG cells (FIG. 10). On the other hand, heparin sulfate (HS) or chondroitin sulfate (CS) glycosaminoglycan chains alone did not suppressed S115 cell growth, even if used at thousand-fold higher concentrations than syndecan-1 ectodomain (FIG. 11).

Example 5

Effect of isolated syndecan-1 ectodomain on cultured cell lines

Figure 12:
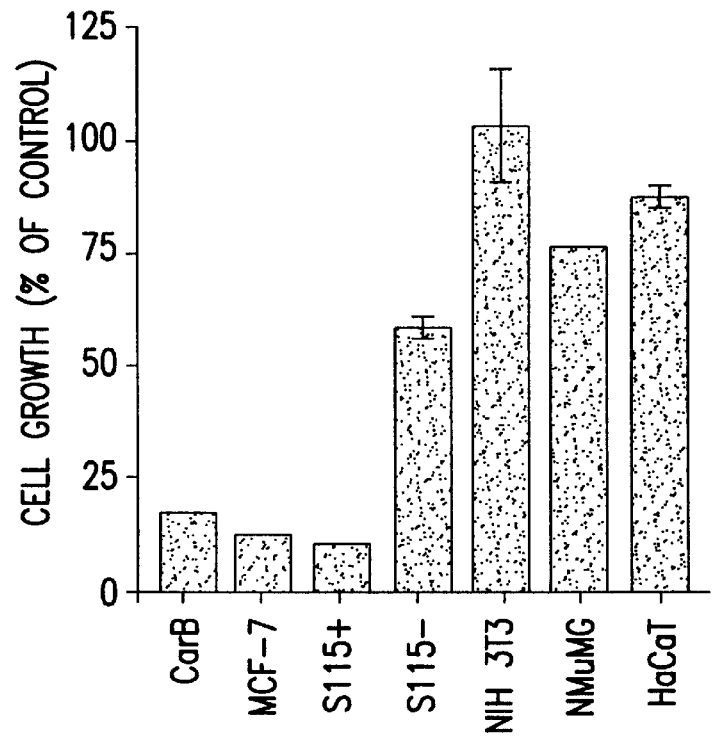
FIG. 12 Growth inhibition of different cell line cells (CarB, MCF-7, S115+ with 10 nM testosterone, S115− without testosterone, NIH 3T3, NMuMG and HaCaT) by 1 nM DEAE-isolated syndecan-1 ectodomain (examples). Cell growth were analyzed in all panels similarly as in panel (A) and it was compared to the cells without treatments (% of control, y-axis). Means and SEMs from two parallel samples are presented.

The inhibitory effect of the isolated syndecan-1 ectodomain was also tested on several other cell lines. These included poorly differentiated squamous cell carcinoma cells (CarB), human mammary tumor cells (MCF-7; ATCC HTB 22), S115 cells with (S115+) and without hormone (S115−), NIH 3T3 fibroblasts (ATCC CRL 1658), normal mammary epithelial cells (NMuMG; ATCC CRL 1636), and human keratinocyte cells (HaCaT; FIG. 12).

Cells were cultured and analyzed as described in FIG. 8 in the following mediums during the indicated periods of time: CarB cells (M. Quintanilla, K. Brown, M. Ramsden, A. Balmain, Nature 322, 78 (1986)) were cultured in HAM-F12-10% FCS for four days; MCF-7 cells in DMEM-5% FCS supplemented with 10 nM estradiol ($E_2$) and 10 µg/ml insulin for 4 days; S115+ and S115− cells were cultured as in FIG. 3 for three days; NIH 3T3 cells in DMEM-5% FCS for 4 days, NMuMG and HaCaT cells in 10% FCS-DMEM for 4 days. Because S115− cells have much slower growth rate than S115+ cells, 3000 S115− cells (other cell lines 1500 cells) were proportionally added to the well, so as to provide comparable results with the S115+ cells. Therefore, for S115− cells, 3000 cell were transferred to the plate as opposed to 1,500 cells for the other samples.

Those cell lines which form tumors (CarB, MCF-7, S115+), revealed strong growth suppression when exposed to syndecan-1 ectodomain at a 1 nM concentration (FIG. 12). In contrast, only moderate or no inhibition was observed with rest of the tested cell lines (S115−, NIH 3T3, NMuMG, HaCaT; FIG. 12), which all are all regarded as non-tumorigenic. Hormone exposure doubles the growth rate of S115 cells (Leppä et al., supra) but if syndecan-1 ectodomain is included in the cultures, the growth of S115 cells without androgen was 5.4 times higher than the growth of the same S115 cells with testosterone (FIG. 12). This was due to inhibition of the "malignant" behaving S115+ cells and undisturbed growth of epithelioid S115− cells.

Example 6

Suppression of tumor in vivo-growth by syndecan-1 ectodomain

The ecto construct was made as described in earlier examples using the full length mouse syndecan-1 cDNA cloned in the Bluescript SK+ vector and a mutagenic 33 base oligo (5'-GACACCTCCCAGTAC TCACTTCCTGTCCAAAAG-3') [SEQ ID NO:2:] containing a stop codon (underlined) and a ScaI site (CAGTAC) to convert the first amino acid (E) after the dibasic protease-sensitive site of the ectodomain to a stop codon. The mutation was selected by restriction digestion and confirmed by dideoxy sequencing. Wild type syndecan-1 and the cytoplasmic deletion mutant were cloned into the EcoRI site of the pBGS eukaryotic expression vector (Mali et al.: *J. Biol. Chem.* 268, 24215–24222 (1993)). The ecto mutant was ligated into the XhoI site of the pMAMneo eukaryotic expression transection vector (Leppä et al., *Proc. Natl. Acad. Sci. USA* 89: 932–936 (1992)) because pMAMneo transfected S115 cells work well in a bioreactory system (personal communication, Sari Ala-Uotila, Turku Center for Biotechnology). S115 cells were transfected using liposome tranfection and subsequent selection with Geneticin as described earlier (Leppä et al., *Proc. Natl. Acad. Sci. USA* 89: 932–936 (1992)).

S115 cells and tranfection cell clones were cultured in DMEM-5% FBS-1 mM Na-pyruvate with 10 nM testosterone, except for S115– cells which were cultured without testosterone in DMEM-4% DCC-FBS (Dextran-Coated-Charcoal treated-fetal bovine serum: eliminates endogenous steroids from serum) with 1 mM Na-pyruvate.

Figure 13:
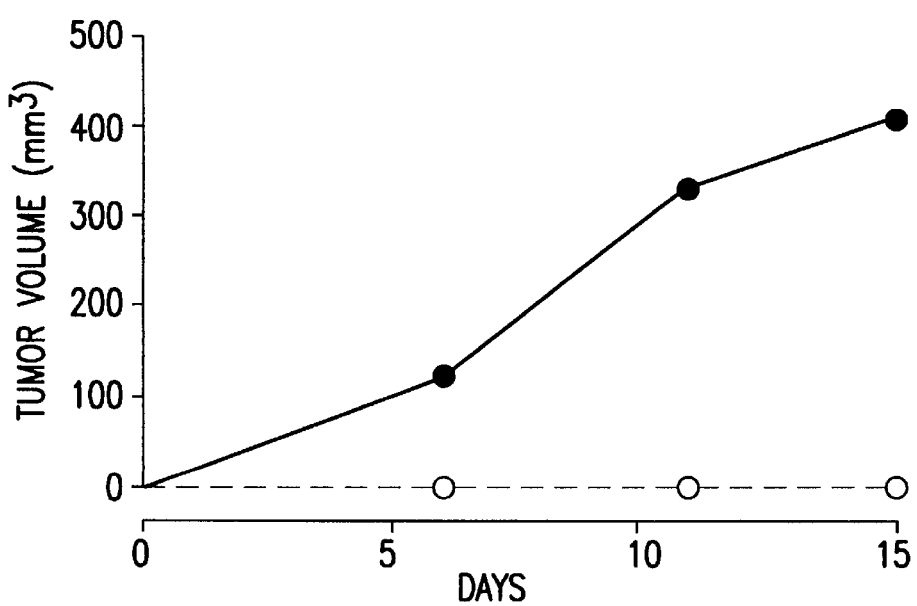
FIG. 13 Suppression of tumor growth in nude mice by syndecan-1 ectodomain. Solid circles (●) represent wild type cells (n=5), and open circles (○) represents ectodomain transfected cells (n=5).

For tumor growth subconfluent cultures were detached with trypsin, washed with DMEM and counted with Coulter Counter (Coulter Electronics). Cells were resuspended in DMEM at a density of $5 \times 10^7$/ml and kept on ice until injection. Athymic male nude mice (nu/nu-BALB/cABom) between 6–8 weeks old (Bomholtgard, Rye, Denmark) were injected subcutaneously with 0.2 ml of the cell suspension. A silastic testosterone capsule was simultaneously implanted. Nude mice were observed regularly for tumor development and the size of the tumors was measured at intervals in two perpendicular dimensions. When the animals were sacrificed, the lung and liver were evaluated for the possible appearance of metastases. The tumor sizes were measured on days 6, 11 and 15 after injection and are plotted as means of five individual tumors in FIG. 13. The ectodomain transfected cells formed only acute inflammation reaction and did not reveal tumor growth, opposite the result obtained with the wild type cells, which formed rapidly growing tumors. This experiment shows the efficacy of syndecan-1 ectodomain as a tumor suppressive agent in vivo.

All references cited herein are fully incorporated herein by reference. Having now fully described the invention, it will be understood by those with skill in the art that the scope may be performed within a wide and equivalent range of conditions, parameters and the like, without affecting the spirit or scope of the invention or any embodiment thereof.

What is claimed is:

1. A method of decreasing the growth of a tumor cell wherein said method comprises providing efficacious levels of syndecan ectodomain to the extracellular environment of said cell, wherein said syndecan ectodomain causes said cell to develop a more differentiated phenotype than is displayed by said cell in the absence of said efficacious levels of said syndecan ectodomain.

2. The method of claim 1, wherein said cell is selected from the group consisting of epithelial cells, mesenchymal cells, pre-B cells and plasma cells.

3. The method of claim 2, wherein said cell is selected from the group consisting of a breast cell, an endometrium cell and a prostate cell.

4. The method of claim 3, wherein said cell is steroid-responsive.

5. The method of claim 4, wherein said steroid is estrogen or androgen.

6. The method of claim 1, wherein said cell is a human cell.

7. The method of claim 6, wherein said syndecan ectodomain is that of the human syndecan-1 of FIGS. 1A and 1B [SEQ ID NO:3:].

8. The method of claim 7, wherein said ectodomain comprises amino acids 18–231 of FIG. 1 [SEQ ID NO:3:] but not the transmembrane or cytoplasmic domain as shown in amino acids 252–310 of FIGS. 1A and 1B.

9. The method of claim 8, wherein said ectodomain comprises amino acids 18–251 of FIGS. 1A and 1B [SEQ ID NO:3:].

10. The method of claim 1, wherein said more differentiated phenotype is indicated by organized actin filaments.

11. A method for treating a patient in need of treatment to reduce or suppress the growth of a tumor in said patient, wherein said method comprises administering to said patient a composition that comprises efficacious levels of syndecan ectodomain to the extracellular environment of said cell, wherein said syndecan ectodomain causes said cell to develop a more differentiated phenotype than is displayed by said cell in the absence of said efficacious levels of said syndecan ectodomain.

12. The method of claim 11, wherein said cell is selected from the group consisting of epithelial cells, mesenchymal cells, pre-B cells and plasma cells.

13. The method of claim 12, wherein said cell is selected from the group consisting of a breast cell, an endometrium cell and a prostate cell.

14. The method of claim 13, wherein said cell is steroid-responsive.

15. The method of claim 14, wherein said steroid is estrogen or androgen.

16. The method of claim 11, wherein said cell is a human cell.

17. The method of claim 16, wherein said syndecan ectodomain is that of the human syndecan of FIGS. 1A and 1B [SEQ ID NO:3:].

18. The method of claim 17, wherein said ectodomain comprises amino acids 18–231 of FIG. 1 [SEQ ID NO:3:] but not the transmembrane or cytoplasmic domain as shown in amino acids 252–310 of FIGS. 1A and 1B [SEQ ID NO:3:].

19. The method of claim 18, wherein said ectodomain comprises amino acids 18–251 of FIGS. 1A and 1B [SEQ ID NO:3:].

20. The method of claim 11, wherein said more differentiated phenotype is indicated by organized actin filaments.

21. A pharmaceutically acceptable composition for administration to a patient, said composition comprising a protein having a domain consisting of a human syndecan ectodomain.

22. The pharmaceutically acceptable composition of claim 21, wherein said human syndecan has the sequence shown in FIGS. 1A and 1B [SEQ ID NO:3:].

23. The pharmaceutically acceptable composition of claim 22, wherein said ectodomain comprises amino acids 18–231 of FIGS. 1A and 1B [SEQ ID NO:3:] but not the transmembrane or cytoplasmic domain as shown in amino acids 252–310 of FIGS. 1A and 1B [SEQ ID NO:3:].

24. The pharmaceutically acceptable composition of claim 22, wherein said ectodomain comprises amino acids 18–251 of FIGS. 1A and 1B [SEQ ID NO:3:].

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: both ( x i ) SEQUENCE DESCRIPTION: SEQ ID NO:1:

GCTGTACCGC TAGCAGAAGA AGGAC        2 5

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: both ( x i ) SEQUENCE DESCRIPTION: SEQ ID NO:2:

GACACCTCCC AGTACTCACT TCCTGTCCAA AAG        3 3

( 2 ) INFORMATION FOR SEQ ID NO:3:

( i ) SEQUENCE CHARACTERISTICS:
        ( A ) LENGTH: 2430 base pairs
        ( B ) TYPE: nucleic acid
        ( C ) STRANDEDNESS: both
        ( D ) TOPOLOGY: both ( i x ) FEATURE:
        ( A ) NAME/KEY: CDS
        ( B ) LOCATION: 206..1138

( x i ) SEQUENCE DESCRIPTION: SEQ ID NO:3:

```
GGAGAGGTGC  GGGCCGAATC  CGAGCCGAGC  GAGAGGAATC  CGGCAGTAGA  GAGCGGACTC              6 0

CAGCCGGCGG  ACCCTGCAGC  CCTCGCCTGG  GACAGCGGCG  CGCTGGGCAG  GCGCCCAAGA              1 2 0

GAGCATCGAG  CAGCGGAACC  CGCGAAGCCG  GCCCGCAGCC  GCGACCCGCG  CAGCCTGCCG              1 8 0

CTCTCCCGCC  GCCGGTCCGG  GCAGC ATG  AGG  CGC  GCG  GCG  CTC  TGG  CTC  TGG          2 3 2
                             Met  Arg  Arg  Ala  Ala  Leu  Trp  Leu  Trp
                              1                 5

CTG  TGC  GCG  CTG  GCG  CTG  AGC  CTG  CAG  CTG  GCC  CTG  CCG  CAA  ATT  GTG    2 8 0
```

-continued

| | | | | Leu | Cys | Ala | Leu | Ala | Leu | Ser | Leu | Gln | Leu | Ala | Leu | Pro | Gln | Ile | Val | |
| --- | --- | --- | --- | --- | --- | --- | --- | --- | --- | --- | --- | --- | --- | --- | --- | --- | --- | --- | --- | --- |
| | | | | 10 | | | | 15 | | | | | 20 | | | | | 25 | | |

| GCT | ACT | AAT | TTG | CCC | CCT | GAA | GAT | CAA | GAT | GGC | TCT | GGG | GAT | GAC | TCT | 328 |
| --- | --- | --- | --- | --- | --- | --- | --- | --- | --- | --- | --- | --- | --- | --- | --- | --- |
| Ala | Thr | Asn | Leu | Pro | Pro | Glu | Asp | Gln | Asp | Gly | Ser | Gly | Asp | Asp | Ser | |
| | | | | 30 | | | | | 35 | | | | | 40 | | |

| GAC | AAC | TTC | TCC | GGC | TCA | GGT | GCA | GGT | GCT | TTG | CAA | GAT | ATC | ACC | TTG | 376 |
| --- | --- | --- | --- | --- | --- | --- | --- | --- | --- | --- | --- | --- | --- | --- | --- | --- |
| Asp | Asn | Phe | Ser | Gly | Ser | Gly | Ala | Gly | Ala | Leu | Gln | Asp | Ile | Thr | Leu | |
| | | | 45 | | | | | 50 | | | | | 55 | | | |

| TCA | CAG | CAG | ACC | CCC | TCC | ACT | TGG | AAG | GAC | ACG | CAG | CTC | CTG | ACG | GCT | 424 |
| --- | --- | --- | --- | --- | --- | --- | --- | --- | --- | --- | --- | --- | --- | --- | --- | --- |
| Ser | Gln | Gln | Thr | Pro | Ser | Thr | Trp | Lys | Asp | Thr | Gln | Leu | Leu | Thr | Ala | |
| | | 60 | | | | | 65 | | | | | 70 | | | | |

| ATT | CCC | ACG | TCT | CCA | GAA | CCC | ACC | GGC | CTG | GAG | GCT | ACA | GCT | GCC | TCC | 472 |
| --- | --- | --- | --- | --- | --- | --- | --- | --- | --- | --- | --- | --- | --- | --- | --- | --- |
| Ile | Pro | Thr | Ser | Pro | Glu | Pro | Thr | Gly | Leu | Glu | Ala | Thr | Ala | Ala | Ser | |
| | 75 | | | | | 80 | | | | | 85 | | | | | |

| ACC | TCC | ACC | CTG | CCG | GCT | GGA | GAG | GGG | CCC | AAG | GAG | GGA | GAG | GCT | GTA | 520 |
| --- | --- | --- | --- | --- | --- | --- | --- | --- | --- | --- | --- | --- | --- | --- | --- | --- |
| Thr | Ser | Thr | Leu | Pro | Ala | Gly | Glu | Gly | Pro | Lys | Glu | Gly | Glu | Ala | Val | |
| 90 | | | | | 95 | | | | | 100 | | | | | 105 | |

| GTC | CTG | CCA | GAA | GTG | GAG | CCT | GGC | CTC | ACC | GCC | CGG | GAG | CAG | GAG | GCC | 568 |
| --- | --- | --- | --- | --- | --- | --- | --- | --- | --- | --- | --- | --- | --- | --- | --- | --- |
| Val | Leu | Pro | Glu | Val | Glu | Pro | Gly | Leu | Thr | Ala | Arg | Glu | Gln | Glu | Ala | |
| | | | | 110 | | | | | 115 | | | | | 120 | | |

| ACC | CCC | CGA | CCC | AGG | GAG | ACC | ACA | CAG | CTC | CCG | ACC | ACT | CAT | CAG | GCC | 616 |
| --- | --- | --- | --- | --- | --- | --- | --- | --- | --- | --- | --- | --- | --- | --- | --- | --- |
| Thr | Pro | Arg | Pro | Arg | Glu | Thr | Thr | Gln | Leu | Pro | Thr | Thr | His | Gln | Ala | |
| | | | 125 | | | | | 130 | | | | | 135 | | | |

| TCA | ACG | ACC | ACA | GCC | ACC | ACG | GCC | CAG | GAG | CCC | GCC | ACC | TCC | CAC | CCC | 664 |
| --- | --- | --- | --- | --- | --- | --- | --- | --- | --- | --- | --- | --- | --- | --- | --- | --- |
| Ser | Thr | Thr | Thr | Ala | Thr | Thr | Ala | Gln | Glu | Pro | Ala | Thr | Ser | His | Pro | |
| | | 140 | | | | | 145 | | | | | 150 | | | | |

| CAC | AGG | GAC | ATG | CAG | CCT | GGC | CAC | CAT | GAG | ACC | TCA | ACC | CCT | GCA | GGA | 712 |
| --- | --- | --- | --- | --- | --- | --- | --- | --- | --- | --- | --- | --- | --- | --- | --- | --- |
| His | Arg | Asp | Met | Gln | Pro | Gly | His | His | Glu | Thr | Ser | Thr | Pro | Ala | Gly | |
| | 155 | | | | | 160 | | | | | 165 | | | | | |

| CCC | AGC | CAA | GCT | GAC | CTT | CAC | ACT | CCC | CAC | ACA | GAG | GAT | GGA | GGT | CCT | 760 |
| --- | --- | --- | --- | --- | --- | --- | --- | --- | --- | --- | --- | --- | --- | --- | --- | --- |
| Pro | Ser | Gln | Ala | Asp | Leu | His | Thr | Pro | His | Thr | Glu | Asp | Gly | Gly | Pro | |
| 170 | | | | | 175 | | | | | 180 | | | | | 185 | |

| TCT | GCC | ACC | GAG | AGG | GCT | GCT | GAG | GAT | GGA | GCC | TCC | AGT | CAG | CTC | CCA | 808 |
| --- | --- | --- | --- | --- | --- | --- | --- | --- | --- | --- | --- | --- | --- | --- | --- | --- |
| Ser | Ala | Thr | Glu | Arg | Ala | Ala | Glu | Asp | Gly | Ala | Ser | Ser | Gln | Leu | Pro | |
| | | | | 190 | | | | | 195 | | | | | 200 | | |

| GCA | GCA | GAG | GGC | TCT | GGG | GAG | CAG | GAC | TTC | ACC | TTT | GAA | ACC | TCG | GGG | 856 |
| --- | --- | --- | --- | --- | --- | --- | --- | --- | --- | --- | --- | --- | --- | --- | --- | --- |
| Ala | Ala | Glu | Gly | Ser | Gly | Glu | Gln | Asp | Phe | Thr | Phe | Glu | Thr | Ser | Gly | |
| | | | 205 | | | | | 210 | | | | | 215 | | | |

| GAG | AAT | ACG | GCT | GTA | GTG | GCC | GTG | GAG | CCT | GAC | CGC | CGG | AAC | CAG | TCC | 904 |
| --- | --- | --- | --- | --- | --- | --- | --- | --- | --- | --- | --- | --- | --- | --- | --- | --- |
| Glu | Asn | Thr | Ala | Val | Val | Ala | Val | Glu | Pro | Asp | Arg | Arg | Asn | Gln | Ser | |
| | | 220 | | | | | 225 | | | | | 230 | | | | |

| CCA | GTG | GAT | CAG | GGG | GCC | ACG | GGG | GCC | TCA | CAG | GGC | CTC | CTG | GAC | AGG | 952 |
| --- | --- | --- | --- | --- | --- | --- | --- | --- | --- | --- | --- | --- | --- | --- | --- | --- |
| Pro | Val | Asp | Gln | Gly | Ala | Thr | Gly | Ala | Ser | Gln | Gly | Leu | Leu | Asp | Arg | |
| | 235 | | | | | 240 | | | | | 245 | | | | | |

| AAA | GAG | GTG | CTG | GGA | GGG | GTC | ATT | GCC | GGA | GGC | CTC | GTG | GGG | CTC | ATC | 1000 |
| --- | --- | --- | --- | --- | --- | --- | --- | --- | --- | --- | --- | --- | --- | --- | --- | --- |
| Lys | Glu | Val | Leu | Gly | Gly | Val | Ile | Ala | Gly | Gly | Leu | Val | Gly | Leu | Ile | |
| 250 | | | | | 255 | | | | | 260 | | | | | 265 | |

| TTT | GCT | GTG | TGC | CTG | GTG | GGT | TTC | ATG | CTG | TAC | CGC | ATG | AAG | AAG | AAG | 1048 |
| --- | --- | --- | --- | --- | --- | --- | --- | --- | --- | --- | --- | --- | --- | --- | --- | --- |
| Phe | Ala | Val | Cys | Leu | Val | Gly | Phe | Met | Leu | Tyr | Arg | Met | Lys | Lys | Lys | |
| | | | | 270 | | | | | 275 | | | | | 280 | | |

| GAC | GAA | GGC | AGC | TAC | TCC | TTG | GAG | GAG | CCG | AAA | CAA | GCC | AAC | GGC | GGG | 1096 |
| --- | --- | --- | --- | --- | --- | --- | --- | --- | --- | --- | --- | --- | --- | --- | --- | --- |
| Asp | Glu | Gly | Ser | Tyr | Ser | Leu | Glu | Glu | Pro | Lys | Gln | Ala | Asn | Gly | Gly | |
| | | | 285 | | | | | 290 | | | | | 295 | | | |

| GCC | TAC | CAG | AAG | CCC | ACC | AAA | CAG | GAG | GAA | TTC | TAT | GCC | TGACGCGGGA | 1145 |
| --- | --- | --- | --- | --- | --- | --- | --- | --- | --- | --- | --- | --- | --- | --- |
| Ala | Tyr | Gln | Lys | Pro | Thr | Lys | Gln | Glu | Glu | Phe | Tyr | Ala | | |
| | | 300 | | | | | 305 | | | | | 310 | | |

| GCCATGCGCC | CCCTCCGCCC | TGCCACTCAC | TAGGCCCCCA | CTTGCCTCTT | CCTTGAAGAA | 1205 |
| --- | --- | --- | --- | --- | --- | --- |
| CTGCAGGCCC | TGGCCTCCCC | TGCCACCAGG | CCACCTCCCC | AGCATTCCAG | CCCCTCTGGT | 1265 |
| CGCTCCTGCC | CACGGAGTCG | TGGGTGTGCT | GGGAGCTCCA | CTCTGCTTCT | CTGACTTCTG | 1325 |

```
CCTGGAGACT  TAGGGCACCA  GGGGTTTCTC  GCATAGGACC  TTTCCACCAC  AGCCAGCACC  1385
TGGCATCGCA  CCATTCTGAC  TCGGTTTCTC  CAAACTGAAG  CAGCCTCTCC  CCAGGTCCAG  1445
CTCTGGAGGG  GAGGGGGATC  CGACTGCTTT  GGACCTAAAT  GGCCTCATGT  GGCTGGAAGA  1505
TCTGCGGGTG  GGGCTTGGGG  CTCACACACC  TGTAGCACTT  ACTGGTAGGA  CCAAGCATCT  1565
TGGGGGGGTG  GCCGCTGAGT  GGCAGGGACA  GGAGTCACTT  TGTTTCGTGG  GGAGGTCTAA  1625
TCTAGATATC  GACTTGTTTT  TGCACATGTT  TCCTCTAGTT  CTTTGTTCAT  AGCCCAGTAG  1685
ACCTTGTTAC  TTCTGAGGTA  AGTTAAGTAA  GTTGATTCGG  TATCCCCCCA  TCTTGCTTCC  1745
CTAATCTATG  GTCGGGAGAC  AGCATCAGGG  TTAAGAAGAC  TTTTTTTTTT  TTTTTTTAAA  1805
CTAGGAGAAC  CAAATCTGGA  AGCCAAAATG  TAGGCTTAGT  TTGTGTGTTG  TCTCTTGAGT  1865
TTGTCGCTCA  TGTGTGCAAC  AGGGTATGGA  CTATCTGTCT  GGTGGCCCCG  TTTCTGGTGG  1925
TCTGTTGGCA  GGCTGGCCAG  TCCAGGCTGC  CGTGGGGCCG  CCGCCTCTTT  CAAGCAGTCG  1985
TGCCTGTGTC  CATGCGCTCA  GGGCCATGCT  GAGGCCTGGG  CCGCTGCCAC  GTTGGAGAAG  2045
CCCGTGTGAG  AAGTGAATGC  TGGGACTCAG  CCTTCAGACA  GAGAGGACTG  TAGGGAGGGC  2105
GGCAGGGGCC  TGGAGATCCT  CCTGCAGACC  ACNCCCGTCC  TGCCTGTGCG  CCGTCTCCAG  2165
GGGCTGCTTC  CTCCTGGAAA  TTGACGAGGG  GTGTCTTGGG  CAGAGCTGGC  TCTGAGCGCC  2225
TCCATCCAAG  GCCAGGTTCT  CCGTTAGCTC  CTGTGGCCCC  ACCCTGGGCC  CTGGGCTGGA  2285
ATCAGGAATA  TTTTCCAAAG  AGTGATAGTC  TTTTGCTTTT  GGCAAAACTC  TACTTAATCC  2345
AATGGGTTTT  TCCCTGTACA  GTAGATTTTC  CAAATGTAAT  AAACTTTAAT  ATAAAGTAAA  2405
AAAAAAAAAA  AAAAAAAAAA  AAAAA                                          2430
```

( 2 ) INFORMATION FOR SEQ ID NO:4:

( i ) SEQUENCE CHARACTERISTICS:
        ( A ) LENGTH: 310 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Arg Arg Ala Ala Leu Trp Leu Trp Leu Cys Ala Leu Ala Leu Ser
 1               5                  10                  15

Leu Gln Leu Ala Leu Pro Gln Ile Val Ala Thr Asn Leu Pro Pro Glu
             20                  25                  30

Asp Gln Asp Gly Ser Gly Asp Asp Ser Asp Asn Phe Ser Gly Ser Gly
             35                  40                  45

Ala Gly Ala Leu Gln Asp Ile Thr Leu Ser Gln Gln Thr Pro Ser Thr
         50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                 85                  90                  95

Glu Gly Pro Lys Gly Glu Ala Val Val Leu Pro Glu Val Glu Pro
            100                 105                 110

Gly Leu Thr Ala Arg Glu Gln Glu Ala Thr Pro Arg Pro Arg Glu Thr
            115                 120                 125

Thr Gln Leu Pro Thr Thr His Gln Ala Ser Thr Thr Ala Thr Thr
            130                 135                 140

Ala Gln Glu Pro Ala Thr Ser His Pro His Arg Asp Met Gln Pro Gly
145                 150                 155                 160
```

```
His  His  Glu  Thr  Ser  Thr  Pro  Ala  Gly  Pro  Ser  Gln  Ala  Asp  Leu  His
               165                      170                      175

Thr  Pro  His  Thr  Glu  Asp  Gly  Gly  Pro  Ser  Ala  Thr  Glu  Arg  Ala  Ala
               180                      185                      190

Glu  Asp  Gly  Ala  Ser  Ser  Gln  Leu  Pro  Ala  Ala  Glu  Gly  Ser  Gly  Glu
               195                      200                      205

Gln  Asp  Phe  Thr  Phe  Glu  Thr  Ser  Gly  Glu  Asn  Thr  Ala  Val  Val  Ala
          210                      215                      220

Val  Glu  Pro  Asp  Arg  Arg  Asn  Gln  Ser  Pro  Val  Asp  Gln  Gly  Ala  Thr
225                      230                      235                      240

Gly  Ala  Ser  Gln  Gly  Leu  Leu  Asp  Arg  Lys  Glu  Val  Leu  Gly  Gly  Val
               245                      250                      255

Ile  Ala  Gly  Gly  Leu  Val  Gly  Leu  Ile  Phe  Ala  Val  Cys  Leu  Val  Gly
               260                      265                      270

Phe  Met  Leu  Tyr  Arg  Met  Lys  Lys  Lys  Asp  Glu  Gly  Ser  Tyr  Ser  Leu
               275                      280                      285

Glu  Glu  Pro  Lys  Gln  Ala  Asn  Gly  Gly  Ala  Tyr  Gln  Lys  Pro  Thr  Lys
               290                      295                      300

Gln  Glu  Glu  Phe  Tyr  Ala
305                      310
```

( 2 ) INFORMATION FOR SEQ ID NO:5:

( i ) SEQUENCE CHARACTERISTICS:
        ( A ) LENGTH: 26700 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 4378..4443

( i x ) FEATURE:
        ( A ) NAME/KEY: CDS
        ( B ) LOCATION: 22026..22107

( i x ) FEATURE:
        ( A ) NAME/KEY: CDS
        ( B ) LOCATION: 23002..23483

( i x ) FEATURE:
        ( A ) NAME/KEY: CDS
        ( B ) LOCATION: 23905..24040

( i x ) FEATURE:
        ( A ) NAME/KEY: CDS
        ( B ) LOCATION: 24252..24418

( x i ) SEQUENCE DESCRIPTION: SEQ ID NO:5:

```
TCTAGATATT  CAAACTCACC  AGATGGAGTG  ATGTCCACCC  CTATTGGTGG  GAGTGACTAG      60

TCTTTCCTCT  GTCTTCTGAC  TCAGATGCTT  AGCTAGCTCT  TTAGGACCCA  CCCTCACACC     120

TGCAAATAAT  ACTTTATTTG  CTCTCTTAGT  ACCTTTAACC  CAGTGGAGTT  GACATGAGAA     180

ATTAACTACC  ATAATTTATA  ATATTTCATT  TCATAAATGA  AAAGTAAAAT  AAATTAAAAA     240

ATAGAAAGGT  TTGAGCATGA  TGGCCCAGTG  GTAAAGGCCA  GTGGCTCCAA  CGCAAGTCCT     300

GACAAATGGT  AACGGGCCTG  TTCTTCAGGC  TTGAGGGAAG  TTTATTGATT  GAGGCTAAAA     360

GCAACCCAAA  GGCTCCACTT  GCCTAGTGTG  AAGCCCTGGA  TGTGCTCTCC  CACACTGCAT     420

GTCCACCTGT  GGTGTCAGCA  CCTGGGAAGC  TGAGGATGAT  GGGGAGTCCA  AGGTCATTAG     480

CTACATAGTA  TAGGCTAGCT  GGGGTACATG  GGTCACAAAA  AAGAAAAAAA  AATAAGCACA     540
```

```
TTGTAATCCC  AGCACTTGAC  AGACCAATGG  GGGGGGGATT  GCTGTGAGTT  TAAGACAGCC   600
TGGCCTACAA  AGAAAAACCC  TACCCAAACC  CAAGAAAAAT  GAAACCAGTA  ATATAAATAG   660
CTATTTTCAT  TTTAAATGCT  CTAAAGACAC  AGCGTTAACA  CAAAAGCTCT  CGTCTGTGGT   720
TCCTATTCCC  TCCTTCTCCC  CCAGGTCTTC  TTTAATGTAT  ACTTTTGTT   TGCTTATTTG   780
CTTGTTTTGG  ATTTGGCTT   TAAAGACAG   GGTCTCACTA  TGTAGCTCCA  ACTATTGGG    840
AACTCACTAT  GTAGACCAGG  CTAGCCAGGG  ACTTATAGAG  ATCTACCTAC  CACTGCCTCC   900
CAAGTGCTGA  GACTAAAGGC  ATGTGACACT  TTGCTTGGTT  ATTACAAACA  TTTTAAAGA    960
ACATTTTGAA  CATTAATAGA  TGTATGTATA  TATATCACTC  TATGTAGTAT  ATATGTTAGA  1020
CATTTTCAC   TTGAGATACA  TATTTACTCT  CAAAATAAGT  TTTTTGTTTT  TTTTTCTTCT  1080
TTTTAAATTT  ATTTTATTTT  TTTTTTATTT  ATTTTATTAT  TATATGTAAG  TACACTGTAG  1140
CTGTCTTCAG  ACANACCAGA  AGAGGGAGTC  AGATCTTGTT  ACGGATGGTT  GTGAGCACCA  1200
TGTGGTTGCT  GGGATTCGAA  CTCTGGACCT  TCCGAAGAGC  AGTCGGGTGC  TCTTACCCAC  1260
TGAGCCATCT  CACCAGCCCC  TTAAATTTAT  TTTTATCTTA  TGTCCATTGG  TGTTTTGCCT  1320
GCATGTATGT  GTAAAAGTGT  CAGAAACTGA  AGTTACAGAC  TGTTGTGAGC  TACCATTGTT  1380
GTGGGTGCTG  GGACTTGAAC  CTGGGTCCTC  TGGAAGAGCA  GTCATTATTC  TTAACCACTG  1440
AGCCATCTCT  CTAGCCCTCG  TTTTTTAGTT  TTTTTTTTTG  TTTTGTTTTG  TTTTTTGTTT  1500
TTTTAAGATT  TTCTTATTTA  TTATATGTAA  GTACACTGTA  GCTGTCTTCA  GACACTCCAG  1560
AAGAGGGCGC  CAGATCTCGT  TATGGATGGT  TGTGAGCACC  ATGTGGTTGC  TGGGAATTGA  1620
ACTCCAGACC  TTTGGAAGAG  CAGTCAGTGC  TCTTAACTGC  TGAGCCATCT  CTCCAGCCCC  1680
GTTTTTTAGG  TTTTTGAAGA  CAGGGTTTCC  TGTGTAGCTC  TAGCTGTCCA  GGAACTAGCT  1740
CTGTAGACCA  GGTTGGCCTC  AAATTTAGAG  ATTTGCCTGT  CTCTCTGCCT  CTCGAGAGCT  1800
GGGATTAAAA  GTGTGCAGCC  CAACAATCTA  CTCAAAGTAG  GTTTGAAAA   AGCTTTCCAT  1860
ATTAGGAGTT  AACTAGCTTC  ATTTCAGAAA  TACTGCATGG  AATTCAAATG  TGGGACCATT  1920
CATAGCTACT  TTGGTTTTCC  TTCAGTGACA  GGCATTCGGC  ATGCCTATTA  GGGAAGTCAA  1980
ATGGCCTGGA  GAAGTCATCC  TGGGTGAGAG  GGCTAATGCA  TTTTCAGCTT  GACAGACACT  2040
GTCAACCTAT  GCAGACAGTC  TGCTCCAGCT  CAGATGTCAA  TTGCATGCAG  ACCTGCAGTC  2100
AGACGCTAAG  CTCCCTACCT  ACTCTCCATC  AGCTTAGATG  TAAGGGGTGC  TGGAACAAAG  2160
GCTCTCTCTC  TCTCTCTCTC  TCTCTCTCTC  TCTCTCTCTT  TCTTAGAATT  AGTATTCTAT  2220
TTTATTTTAT  GTAAATTGGT  ACTTCACTTA  CATGTATGTC  CGTGTGAGGA  TGTTGTATCC  2280
TCTGGTACTG  GAGTTATAGA  CAGCTGTAAG  TCGCCATACA  GGTGCTGGGA  ATTGAACCCT  2340
GATCCTCTGG  AAGAATAGTC  AGTGCTCTTA  ACCCCTGAGC  CATCTCTCCA  ACCTCTTGCA  2400
TATTGAGGAC  AGGGAGGAAT  CACAAGCCAT  GTAGGGTGCC  TGGGCTCTGA  GGTCAACAGG  2460
ACCATAGCCT  CCTTTCTTTA  TGTGCCTTTC  TTGGGGTCTC  CCTATAGGAG  TCGTCTTCGT  2520
TGCCTCTTTA  CTGTCTCATT  GATCTGGGCT  AAACTTATGC  AGTTGGAAGG  AAAGATCAAG  2580
CTGGTCATGT  TTAAAACATG  AAACAGCCTC  ATCAGTTCCC  TTCCTGTTCC  CGTCTCCCCC  2640
CCCCCTCCCG  CCCCCATTTT  GAGAGGACAG  GAAGGTAAAA  TACCAAAGTG  TCCTATTTTC  2700
CTCCAAATAT  CAGGCTCAAA  GGACTGAAGA  GCTGACTTCA  GATCCCAAAG  CCACTGTGTT  2760
AGGAGGCACC  TGCTTTTTAG  GTCCTAAGCC  TTCCTGAGCC  TTGCTATTGG  GTATTCTTTA  2820
CCAAGACCCT  CAAGGATCTA  GGCAAGAACT  GGGCAGGATC  TGTATGTAGC  CCATAGTTAG  2880
ACCTAGGGCA  GCTGAGACGC  CAAAAGGGAG  AGTTTCCTGA  GGACAAAAGT  GTTCAAACAC  2940
```

| | | | | | |
|---|---|---|---|---|---|
| AACTGGGTGC | TGGTTGTTGG | GCTACTCGTG | GAGGTGTGGT | GTGTGTAAAG | GAGGCTGTTG | 3000
| AATTCCCAGA | AGGCTGGTTC | CACAGTGTAG | AGTCTACACT | GGGGACTTCC | CGAGACGCTG | 3060
| AGCCTCAGAT | CTAGCTTCTC | AGTCCAGGCC | AGCTGATGTG | GGGCTGAGGA | ACAAGGATGG | 3120
| ATGCCATCTA | TGGCCCTGCC | TTGCAGGTGC | AAAGGGCCTT | TGGCACCATC | TACAGATTGA | 3180
| GGGCAAGACA | GGGCTGGTTC | TTCCTCCTTG | CTCTCGCTGC | TATCTGCCTC | GCCTGTAGGC | 3240
| TCTCTGGGCT | CCTTTTTGGA | CTGACACGTC | TGAAGGAGCT | TGGAAACTGT | GAGGTCCAGG | 3300
| CCCCATAGAG | AATCATGAAG | GAACAGGAAT | TCAACTGGAG | CTCCGCAGCT | GGTTAGGCCT | 3360
| GCGGTCACCT | GGAAACAAAG | AGGCCATTTA | TTTTTTCCTT | TGGTCTTGGA | CAAGGAAGAG | 3420
| AAGGGGCTTT | CTATAAATAG | AAAGACAGCA | AAAAGAAAA | TAATAATAAT | AATAATAATA | 3480
| ATAATAATAA | TAATAAAAAC | AATAACAAAG | CCAGCTCTTC | CAGACAGTGC | TCATGTCTTT | 3540
| AAAGGTCTTT | AAAGGTCTGG | AGTTCCCAGC | AATTAAGTAA | AGGACCAAGA | CCTCAGGGGT | 3600
| CCCCTATCCT | CAGCCCGTGG | GGAGGTGGGA | ACCATACATC | GATCCCTCGG | TTTATATATA | 3660
| GCCTCATCGC | TGTGGGGCTC | CGAGGTTGCC | CCCAAAATCT | TGCTCACCTG | GAGGACCCCT | 3720
| GGGTGTCCTC | GCCCAGAGGG | CGCTGCAGCC | TCGCACGTAG | AGAACTAACA | TCGCCCTTCT | 3780
| CCAGGGCAGT | GCCTCCGGAC | TCCGGACCAG | GACATAGTAG | CGAGTGCACC | TGGGTCTCCG | 3840
| TCAGCTACGC | ATCAAGGAAG | GTGCGACGCG | GGAATTACAG | ATTGCCGGCA | CTCACCAGTG | 3900
| CTCAGGGGAG | GAAGGTGGGA | CTCAGACCTG | CAAGAGCTGA | AGAGTGGGGT | GGGCTTCGAT | 3960
| CCTAGGAGGC | GTGGAAGGGG | GTGTGGCTGG | ATCCCTGGGG | GGTGGGGCGC | TCCAAGGGGC | 4020
| GGGGCAACCC | AGGGGGCGGG | GCCCGAGGGG | TGGAGATTGG | GACTACCCAG | GCCCGCGGAG | 4080
| CTGGGGGTGG | GCGGCTAGTT | TTGCAACTGC | AGAGCCTTTG | GGTTTATTAT | AAGGCGGAGC | 4140
| TCCGCGGGAG | AGGTGCGGGC | CAGAGGAGAC | AGAGCCTAAC | GCAGAGGAAG | GGACCTGGCA | 4200
| GTCGGGAGCT | GACTCCAGCC | GGCGAAACCT | ACAGCCCTCG | CTCGAGAGAG | CAGCGAGCTG | 4260
| GGCAGGAGCC | TGGGACAGCA | AAGCGCAGAG | CAATCAGCAG | AGCCGGCCCG | GAGCTCCGTG | 4320
| CAACCGGCAA | CTCGGATCCA | CGAAGCCCAC | CGAGCTCCCG | CCGCCGGTCT | GGGCAGC | 4377

| | | | | | | | | | | | | | | | |
|---|---|---|---|---|---|---|---|---|---|---|---|---|---|---|---|
| ATG | AGA | CGC | GCG | GCG | CTC | TGG | CTC | TGG | CTC | TGC | GCG | CTG | GCG | CTG | CGC | 4425
| Met | Arg | Arg | Ala | Ala | Leu | Trp | Leu | Trp | Leu | Cys | Ala | Leu | Ala | Leu | Arg |
| 1 | | | | 5 | | | | | 10 | | | | | 15 | |

| | | | | | |
|---|---|---|---|---|---|
| CTG | CAG | CCT | GCC | CTC | CCG | GTGAGTGTGG | CCCGGGGCAG | GGCTGGGAGG | | 4473
| Leu | Gln | Pro | Ala | Leu | Pro | | | | |
| | | 20 | | | | | | | |

| | | | | | |
|---|---|---|---|---|---|
| CGGCGGGAAG | CCGGGACTCG | CCACTCGCCG | ATGCCATGCA | GGCGGCAGCA | CGTGGAGGGG | 4533
| GAGGGGAGCG | GGGACTTCTT | CCCGCGCTGC | CTGGCGGATC | CTGGGATGGT | GAGCCCTTTA | 4593
| ATGAGGACTC | CTGTCCCAAT | TCCTCTACGG | TCCGTGGATG | CCAGGAGGCT | ATCCCAGCTC | 4653
| GTGGTCCGGG | CGTCCTGCAG | AGTGGAACCT | CCATTGGTTC | CCCGCTCCCA | ATTAAGTAAA | 4713
| ACGACTCCAC | AGGGGTCTGA | GTCGCCGGCC | TTAGGCGCTC | CGCCGGCCTT | AGGCGCCGCT | 4773
| TGGAGTTGCT | CTCTCCCGTT | GCTGTCTTGC | TGGCCATCTC | AGCGGCCTGG | CCTCCGCCAG | 4833
| TGTCCCGGAG | GATGCAGTGG | CCATGGCCAA | ACGCCTTTTC | CATAGACCCT | AATTCAAACC | 4893
| AGACTGCAGG | CTGCACCCCC | AGCGCCGCGG | AGTCCGGGCG | CTCGGCCCTT | TGCACCGGGG | 4953
| CAAGTTTGGG | CACAGCAGAG | CCGGCGCGGG | AACAGGGGGA | AGCTGACGTT | CGGGGTGGCG | 5013
| GGAGGGACGG | GATTAAGGCT | GTTTGTGGGA | CACAAGAGGG | TGGCTCAGGG | ACTTCGGTTT | 5073
| TTCTCTGGCT | GCCCCAGGTG | AGCCGGGCCG | AGCTGGCAGC | GGGAGGTTCC | GGGAAGTTGG | 5133
| CTTCAGAACG | CTGAAGACCC | TAAGAACCCA | ACTTTGGGGT | CGCTGAAGTT | GTGCTGCCCC | 5193

```
CGGAGGGCCT CCTCCGCATG GCCCGCGCGG GGGACCCTCC CCGCGAGTGG ACCCCGGTAC    5253
GGCTCTTCCC CTCCCCCGAC TCGGCTTTGT GCTGAAGCCG CGCGTAGGGA AGGCGGGTCC    5313
CTTGGCCCGC CCAGTAGGGC CGCGGGGAAA GAGGGACGAA CGTGGAGCTG GCGACTGGTG    5373
GGGGAAGCTT CTGGGTAGGA TGCAGCCATC CACCTTTGGT GGGGTCGGTC TCTCTAATCA    5433
GCGGCTTGGC GACAAAGAGC TTGGTCGAGG GTACCCAGA AAGTGCTCTC CCGCCCCAAG     5493
CCGCCGTCGC TAGCCCGCCT TCCCAACGGG CGCTTTGTTC TCGGCCCCTG TAACCCTTCC    5553
CTGGGAACCG CCCCGCAGCG CTGGTCCTTG ACGTGGGCCG GGTCCTGGGT CGCCGCCAGT    5613
GTCAGCGCTG CCCTCCGGTG TCCACGCCCC TAGCCCCGC ACCCGCTGTG AAGTCCCGGG     5673
TGTCCTTTCC ACTGGCGCTT TGCCCAACCC CTGGAAGGCA GAGGCGAGGT GCGGAGCCTC    5733
AGGCTTTATC CTCCCGGAAG TGGCAGTCTC CCACCGCCAC ATCTGGTCTG CTTAACTTCG    5793
ATAGTCCTGG CAAAGGCAGA CACGTGCACA GGGAAGGAGA GTTGAGCGCT GGTAGATACC    5853
AAGGTCGTGT ACAAATAAAG TGGCACACGA CACGTCCCCA GTCACTGTTA ATGCATTGCC    5913
TTCGCTCCTT CCCAGGTGGC TGGTGCTCTC CATCACTCTG GAGCCCAAGA GAGGGCCTCC    5973
ATAATTGTAT TGCCCATGAG TTGGGGTTGT GTGGGGGCGC CAAATCAGGG TTCTCTGGGA    6033
GGGCTATGAA TTCCGAACTG AGTCTCCTGT GCACTCCTGG CTTTAAGGTT CAAGAAATTG    6093
TTTGAGGGTT GTGGTTTTTG TGGGACTCAG ATTATGCCTG GAATCATAGT TACCACTGTG    6153
GAGAAGAAAG TGGAGCTACT TAGCATGCCT CCCCGGCCCG CCTGGCATTA CCTCCGGCTC    6213
TGTTCTCTAG GCCCAACGTG AGGCCTCACT GGGGCAGTAC AGATGCAGTA CTGAATTTCT    6273
TTCCAGCCAG GATCTGGAGA GGTGGTGTTC TCTTCCCTGG TGTCTTTAGA GAGGCAGATA    6333
TTCCTGTGAC CTAAGCCCCT CAAGCACCCA TTAATAATGC TGAGTAGACA ACTAGAGGTG    6393
GCGTTTTCCG GAACTTCCTG TGTGCTGGCC TGGGAGGTTG AACCCTCTAG GAAACAGGTC    6453
TAGGAAGTAG AATTATCTCA ATGGAAGGCT TCCTGGAGGA AGAAGATGAG CTGAGCCCCC    6513
AGGTCACTGT CTGAGCTTTA GGATCAGACT CCCACTTGGA GGCAAGAGTG TTCGTTTTAC    6573
TTTTTTTTTT TAAGTTTAGT TTATTTTCTC TCTAACAGAA AACAAACAAA CAAACAAAAA    6633
AAAACCCCAC ATTGTTTAAA AGTGGGTGCA TAAGAGTGAG GACATATTCA GAGCTTCCCC    6693
TTTTCCTGAA AAATGAAGGC AGCTGGGATT TACTTAAAAT GAGAGCACAT ATCACAATTG    6753
CCAGAGAGCT GGTCCCTTTC TCAGGGCTCC CTAAGCTCCT GTGGGAAGCA GGTCAGACAG    6813
CCCTGGGGAC CAGAGAGATA GGGAGTGCTT TTGGGTGCCT GCCTTTGAAT GGGGAAGGGG    6873
GGGGGAGCTG CTGGGATCAG AGGCTGCTAG CAACTACTCC CCAGAGACTG AAGCAGGTTT    6933
GTCCCTCAGT GTCCTGTGGT CTTCTGTTTC TCCTATATAG AATAGGAGAA ATGGTTATTT    6993
GCTCTGGAAT AGTGACTTGC TATTGTTCC CTTTCTTTCC TCTCCCTTAC TGTAATCATT     7053
TGGACTAGTA GAGACACTTT CCCCAGGTCT GGCAGAATGG GAGGGAGTGG GGGAGGCCTG    7113
TGCTTGCATG ATGTCACTGC TGGCTTCAGC TCTCCAGGGA GGGTGGAGTT GGTTGTAACC    7173
TACCTGTGGC TCTTGATGGG CCACAATAAA ACCTCATTAA CACACATTGG TAGGGAGAAG    7233
GGACTGGAAA GAATGATGGG AAAGATTGAT GTTTTCCTT TTTTTTTTT TTTTTTTTG      7293
GCAGTACTTT CTAGATCTCC CCTCCCCCTT GCTGCAGCAA AATTTTGGAT TCCTGAAGTC    7353
CTTTGAGAAT GTATAATGGT AGCCAGACTT TTTTTTTTC AGTCAGCTCA AAATTGCCTC     7413
CTTATAAAGT ATCCTTGGTT GTTTTTTGTT GTTGTTGTTG TTGTTGTTTT GTTTTGTTTT    7473
AAGACAAGGT TTCTCTGTAT AGTCCTGGCT GCCCTGGAAC TCAATATGTA GACCAGGCTG    7533
GCCTCAAACT CAAAGAAATC CACCTACTTC TAACTTTCAG TGCTGGGCCT AAAGGTGTAG    7593
```

| | | | | | | |
|---|---|---|---|---|---|---|
| GCCACCAAAA | GTGCTCAACT | TTTACAAAGC | AGTCTTACTT | TGAGCAGGAT | TCTGAAACCC | 7653 |
| TTATTTCCTT | TCTGTTATCT | TCAACAATAC | ACTGCTAGGT | GTATTTAGTC | CCTCATGATG | 7713 |
| CTGGGCCTCC | TCAAGTGGCG | CCAGGTCAAG | CAGTCTCCTG | GTTTTGGTG | GCTCTGAAGA | 7773 |
| AGACTGTGTC | CCAGTGACTG | GCAGTTTGAA | TTCGGAGCTT | CTCTTTTCCT | TCTCAGTCTT | 7833 |
| TGGCAGGCAG | AGTGACACTG | GTGTGCCCAA | GCCTGGAGCT | TCTCTGTTTA | ATTCTAGTTT | 7893 |
| ATTTTCTTTA | TCAGACTGAA | AAACAAATCA | GGTTGGTTAT | AATTCTTATA | AACACGAAGG | 7953 |
| TCTCACCTTT | GCGTACGTCT | CCGGCTGTGT | GGGTCTGATG | TCCCTCGGGA | ATCTCTGTTG | 8013 |
| AGGCTGCTGC | AGTGTGTGTG | CGTGTAGAAA | GGGCAAGGTA | GAATGGACAG | AAGCGTGCTG | 8073 |
| CCCACCCCAC | TGTCCTGTTC | CTAAATGATG | AAGCACTGGC | CCGGTGAAGA | GCCTAGAGAA | 8133 |
| CTCCCTCGGT | GGGAGATGCA | CACAATGCCA | GGAAGCACAC | AGGAGCTTGA | GTTCCAGCTT | 8193 |
| GGCAGTGTCT | TCTCTTTGGT | GACTTATCA | GCTCCAGCTG | CCCTGGACTA | ACAAACAAGG | 8253 |
| CTAGCTCACT | CTCAGTATTG | ATAATCGAAG | GTCCTTGGTT | CTGTTTGAGA | CTGATCCTCA | 8313 |
| CTCGGTAGCC | TTGAACTCTT | AGCAATTCTC | CTGTCTCAAC | TTTCAAAGAG | CTGAAATTAC | 8373 |
| AGACTCGAGC | CACCATATGC | GACTGAAACC | TTGTTCCTAA | TCCTTGACTG | TGAACGACTC | 8433 |
| TTGGGTTTGG | TTCTTTCTCC | ATTTCTTTAG | TGTATGTTTT | AGTTCGCGTC | CTACATAATC | 8493 |
| TATTGCCCAT | ACTTAGAAAC | AACAGGTTAG | AGACAGCATT | GGGTCCAGCA | GAGCCTCACA | 8553 |
| CTGAAGCTCA | GTCCTGCCAC | TGATTTACCG | TGTCAGCTCA | AGTGACTCAC | TTCCAACTCC | 8613 |
| TCTGCTCCCC | ATCTGTAGAG | TAGACATCAC | CATACCTGCT | CTTTCTGCCC | ACATTCTGTC | 8673 |
| ATTAACATGT | TCATTTCATA | ACGATGGTGC | AAAAGTGCTT | TGTAAGTAAA | GTGCTGGGGA | 8733 |
| AATGTTAGCT | GTCGATAATG | GTTAGGGTTA | ACTTTTATT | GAGTGCCTGT | TGTGTGTGGG | 8793 |
| GTTGGGTGGG | GTTTTTTTAG | AGGCTTGGTA | GTTTTCTTAC | TTCTTTCCTA | CTTAGCTTTT | 8853 |
| CTTCCTAAGC | CTTTATGGTA | TGTATCATTG | CCTGATTGTT | TGAGTGTGTG | CACTGAGGCA | 8913 |
| CGCCTGTGCA | TGTTTGAGAG | TATGCTTGTG | CGTGCTCTCG | TGCTCACATA | TGTATGGTGT | 8973 |
| GAATACACTG | TAGAGTGCAG | GCCGGCACAC | TGGGGCTGGC | TGAATCCTGT | GAGCCCTGCC | 9033 |
| TGGAGTTTGC | AGATCTTCCT | TGGACACTCC | TGCTTGTGAG | CATTTTGTGT | GGAGTGACTG | 9093 |
| TTTAGCTGGC | TGTAGCCTAC | ATTGTGCCTT | TGGGTAAACC | CTGAGTATTG | GGAAACACCC | 9153 |
| TGGGCTGTGG | CTGTGTGTGC | CCGACGGTTG | CTTGGGTACA | GCTAAGAACT | CTTCATAGAA | 9213 |
| AGTTGAGCTC | ACATGCTATT | AGTATTAACT | GAGTGCTAAG | GAACCTGTCT | TGGGTGGTAC | 9273 |
| CTGCTTGCCC | TCTCATGCAG | TTTATCTTGA | GCTTGGCGAA | CACACTTACA | GATTTAGTAG | 9333 |
| AGCTTTTGTC | AGCCCTGGGA | GGTGGGTTTC | GTGGCCACAA | GTGGGTAGCT | TGGAATCCAA | 9393 |
| GACTCCTGGC | TTCTAGGTTG | CATTCTCCTG | TGGTTCTTTC | CAAGGGAATG | CTAGGGAAC | 9453 |
| ATTTGGACA | TTAGATTATT | TCTAGTCCCA | AAGCACACAG | AACATACTGT | TTCCTAATTG | 9513 |
| CCTTTTTTTT | GTTTTCCTCT | CAATCTGGTT | TTGAAGTGTT | GGGTTTGAAA | ATTGCCCCCT | 9573 |
| GAGAGCCTGC | CCTAGTGTGT | GCAGAGGGAA | GATAGTGGAA | CAGGAAGTCT | GTAGAAAGTA | 9633 |
| TCTTCCTTTC | CAGGACCTTG | TGCCCCGGAG | CAGAGTCAGC | ATGGTGTCAT | ATCGCTTTTG | 9693 |
| GCTATTCCAG | AAGAGATGAG | GTTTTAGGTG | AGAATGAACC | TTTTAGAACC | TTCTAGAACC | 9753 |
| TTCTGTTGAG | TATGACAGGA | ATGCCCTGAA | TAGGGTCCGA | AGTGCATGGC | CACTTGTTTG | 9813 |
| TCTTTTCCAT | AAGCAAGCAG | CTTCAGGTAC | AGACAATAAG | ACTAGGTTCT | TGGAGTGAGA | 9873 |
| CCCTGCACTT | GGTGCCATTT | CAGCTCCAGA | TGGACACTGG | AGGTCCCTAC | ACAGCAGGCT | 9933 |
| CTGGGATGGC | TGGCTTTGCT | ATGTACTGTT | GCCTGCTCTA | CAAGAGCTTC | CCAGGTTACT | 9993 |

-continued

| | | | | | | |
|---|---|---|---|---|---|---|
| AGCCTTTGTC | GACGCTGGGC | TCGCTGGCCA | GGCTTGGGCA | TTGGAGAAGG | GACAACTTGC | 10053 |
| CACCTGGCAT | AGGCTGTGTG | TTTGGAGAGT | CAGGAGGTCT | GGTGAAGCCC | GCAAGTGGAG | 10113 |
| GCAAGTTTAG | TGGGACTTGA | GGAGAGCTCA | GTAGGAAATC | TCTGGGCTAG | TGACAGGCAG | 10173 |
| GTGTGGTGGT | GGTGGCGAGG | TGGCGGGTCT | AGATCTCCTT | TTAGAGATTT | GCCTAGGGAT | 10233 |
| CGTCCCTGCT | GACTCTGGAA | CTCAGAGGCC | TCCAGAGGTG | TCTCCTCTGG | GAGCCTCTCA | 10293 |
| AGGGTCTCCC | ATCTCCTACT | GTTTATGGCT | TTGTGGGCTA | CCTAATTACA | TAGAGAAGAT | 10353 |
| ATGTTCCTCT | GCCTCCAGCC | CTGGAAAGTT | CTGCCCAGTG | ACTCACCTGA | GCCTGCAGCC | 10413 |
| ATGTGTGTAC | ACAGGCGCTC | TCAGGGGCTT | CTGTCCTGCT | GGCTTCAGCC | TTTCTAGCCC | 10473 |
| CTGGTGTTCT | CGGCAGTGGT | AGCATCTGGG | AAACCGGGTC | ACCTCTTATT | TGCAGCTCCC | 10533 |
| TCCCTTTCTT | GGTGTCTTCC | CCCTTTTTAA | CTACTGGTCT | GATGGCTTA | GACTCATGCT | 10593 |
| GAAATTCTCC | TTTCTTTTGT | CCTAGCCTTG | TCTCTGACTT | CTTGTGATCC | TCTGGGCCTG | 10653 |
| TGAAATCCGC | TCAGGGCCT | CCATTTCTAA | CAGTCACACA | CTGGTGGAGA | GACCGAGTCC | 10713 |
| TGGGATGGTG | AAGCTAACCC | TGCTGGGCTT | CTCAAGCTTC | ATTTGGTTTC | TCTTTATTCC | 10773 |
| TTCTGGAGGT | ACTGCCTGCC | CCAGGGGAGT | CTCAGACTAG | ACCACTCTGG | AGTTGGAGGT | 10833 |
| GGGGCAGGTT | TTCAGATCAG | TGCCCTTGGC | ATTCGTTGTG | GGAATGGGGT | GGATGGGGCC | 10893 |
| TCTGGGCAAG | GTCAGGCTGG | GGGTGGAGGC | CAGGTGATGT | TCTCCGCACC | CACACCCAGG | 10953 |
| CAGCCTGGCA | CCCTCCCCAA | GGTCCGCTCA | TCAGCAGGAA | TGAAAGCAGT | GCCGGGCAGG | 11013 |
| TTGGGGCAGT | GGGCAGGTGG | GCGTGTTTAT | CGCTGTGCTC | ATCAGCTGAG | TCACGATGCC | 11073 |
| AGGCCCCACA | AGTCCTCCCT | GGAGGCTCAC | CCCACCCACC | TTGACCCACC | AGCACCCACT | 11133 |
| AGCAGGAGGT | AGGGCAGGGC | AGTGAGACAA | GACCAGCCTG | GGGGTCTGAG | AGGCAAAGGG | 11193 |
| GAGTTGTTCA | TGACCTGGCT | GTGCATGGGG | ACTTGTGGGT | GTCTCAGATA | TCTCTGCTGT | 11253 |
| CCAGGAGGAA | GCTGTCTTAA | GTGCCAACCT | GCCTAGAGCC | CCTGCTGGGT | GCAGGAAATG | 11313 |
| CACAAGGGAG | AGTGCCCATC | CATGGAATAG | GCCCATGGAG | CTAGACCAGT | GACAGTGACA | 11373 |
| GTGAAGTCAG | CCCCCACCTG | TGTCTTCCGA | GCCAGCTGGA | GGGTTTTAT | CTCAGATTCT | 11433 |
| GCGAAACCAT | AGAATCTAGT | CAGGAGCCTA | GACTGCAAAG | CAGGCTTCGT | TGATGCTTTA | 11493 |
| ACTTGCAGGC | TTCCTGGGTA | TGAGGGATAC | TTAGAAAGGT | CCCGCAGGTA | GGGAGGGCAT | 11553 |
| CAGGAAGTAG | AAGAGGGCCA | GGCACTTCTA | TCTCCTGCAT | TGCCCCCTTC | TCCCATCTCC | 11613 |
| AAGGATGGTA | AAAAGAACCC | TTCCAGTACA | CTGACAGAGA | GGAAAACCCT | TCATCTCACC | 11673 |
| CCATTTGGAT | CTGTCGTATC | AGCATGTGCT | GGCCCTGCTT | CCATACCAGA | GGTGGCTAGA | 11733 |
| GATGTTCCCT | GGGAATTCAC | TGGTTGGGA | CTTGAGTGTA | TCAGAGGGGC | ACAAAGTAAC | 11793 |
| ATTAACTCTG | GTATCCTCTG | CAGCAAATCG | GAGATCCCCT | CTCCTAGGCG | AGTTCTCAGT | 11853 |
| GGATATGGAG | GTCAGGTTTG | GGCTTGTAGG | GCCCCAGCAA | GAGTCGTTGA | TGTCACTCCA | 11913 |
| GCTTCTCCCG | AGGAAGATGA | GGGTGCTGTG | TTGGGATCAC | ATCTCTCCCT | GAATGGCATG | 11973 |
| TTGGGGAGGG | ATGGAGCCCT | TGCTTCTGAC | CCCTAAGCTT | GGTCTTTAGG | TGGCCACAGT | 12033 |
| CTCTGGGTTC | TGTCCTACCT | CCCTGCCCTT | GTGTGCTTCA | AAGGCATGCT | AAAGGGACTC | 12093 |
| TCGGCCATTC | CGAATGGCAC | AGTGTTCCTT | CTGTTCTCCC | ACCCCCAGAA | GGAGGCAGGC | 12153 |
| CTGGATTGTA | GATTCCTAGA | AGTAAGTGGC | CCTGAGCATG | CTGTTGATGA | ACCTGGAACC | 12213 |
| AGGCAGGCTG | GGCATCCTAG | GACCTGTCTT | TCCATAGAAG | TCTGAATCAG | TCTACCTTTG | 12273 |
| GGACTGAGTA | AGGGCTCCT | CACATATCAG | CTGGCTAGTC | CATCTTGGCT | GATCTAAACC | 12333 |
| ACATTAGGCT | GAAGAGAAGC | ATGGTGTACA | GTCTGGTCCA | CCCGAACCAC | ATACTGGCTT | 12393 |

| | | | | | | |
|---|---|---|---|---|---|---|
| TATCAGTTCT | CGTATAATTT | TGCAGGTAAC | TTTTTAGCTC | TAAGCCTGTC | TCCTCATCTG | 12453 |
| TGAAATCGGG | TCCCTCATAT | CCTGCCTAGA | AGGGCTTTTG | AAAAGATTAA | TGAAGTAGTA | 12513 |
| TGCCGAGTGG | TTGGGGTTCT | CTCCTTGACT | GGAGCAAGTC | TCTAGGAGTA | CTAAGGATAG | 12573 |
| CCTGCTGTGT | GCAGCACCCC | CAGGGACTGT | GCCTGAGTAG | GAGGGTACAG | AGTCTTCATG | 12633 |
| TGAATGGCCC | TTCTGGTCTT | GCCCCGAAGT | TAGTGTTGAT | GTCATAGAGT | CTACAAACAT | 12693 |
| GCCTTTTGTC | CTTCCTCAGA | AGTCCAAGCC | TTTCCTGGCA | GACCAGACAT | TCATCTCCAC | 12753 |
| TGAGCCTCTA | TGTGAGACTG | GCTCCTGGCC | TGAGCTGTGT | GGGCTGAGCT | GGCGAATGGG | 12813 |
| AAAACTAGAC | ACCTGGGCAC | CTGGGTGGGG | GCTCGGGACA | GCAGTGTTTC | AGTTGTAGGC | 12873 |
| ACTGTGCCCC | TGCCTGGAGC | TTCTGACTGA | AGGTTACCCT | GAGAGGAAGC | AGGTTCCTA | 12933 |
| TAGACACTAA | CATAGCTGGG | TCAGAGTGCA | AGGTGGGTGT | GCCCCTGCCC | TGACCCATTC | 12993 |
| AGTGCAAAGG | CTGCTCTTCT | GGGAGTGAGA | GCTCTGACAG | GACTGTGATG | GCCGAGGGGT | 13053 |
| CTCAGAGCAA | ACCTGCCTGG | CCTCTCCCCA | CTCTGATGGA | TATGTGCTCT | TAAACAAGTG | 13113 |
| ACTGTCCACT | TTGCCTCAAT | TTCAACATCT | GTAAGATAGA | TAGGGCGTTA | TGGTCTGAAA | 13173 |
| ATGGTTTTAA | AGATTAGTTA | GCTAATACAG | GGAAAGTGCT | CTGACAGGTA | CCTGGCACCT | 13233 |
| TACTCAACAA | GTGGCTGGAG | TGCCTGATTT | CCTAAGGTCT | CGACCTGTCC | CTATGCTTCA | 13293 |
| AGTGCCCCTA | CAGCCTTGGT | CAGGCCCTTA | GGTTCTCCCA | CCCACCGCTG | GCCCCAGGAC | 13353 |
| CTAGACTGCT | GGACCCTGAC | CCCATTTTTC | CTTTAAGCCA | CCTCTGCGTC | AACTCTAAAA | 13413 |
| GGCGGTGGAG | TTGTTTATCT | AGGCTGTGAG | GTGTCAGAGA | AAGGACCTGG | GCCGCTTTGT | 13473 |
| TCCTGTGTGG | GCTGGGGCCA | CTCCAGGAAC | TGAGAAACCC | ACCCACCTTT | TCAAAAACAG | 13533 |
| CCTCTTCTCA | GAGTCTGGCA | CCTCAGCTAG | CCACCATGCT | GTGGGACCAC | TCCCAGCATG | 13593 |
| CTCTGCCTTT | GGTTTGTTTC | CCAGGGGCCT | CAGTGCCTTT | TAAAGATGCA | CAGGCATCTT | 13653 |
| TAGTTCAAGG | GGAAAGAGGA | AATGAAGTGT | ATTTGCTGGT | GGTGGTATTC | CTGTCACTTG | 13713 |
| CATTCTCACA | GAGGCTAAAG | AAATTTGCTC | TTTGTATCTT | CTAGTCTCTT | CTTTATGATC | 13773 |
| TTTTCCCATC | TGTTGTATCC | CAACTGCAGG | GCCCCAGTTC | TAGAATTAGC | CCCTCCCCCA | 13833 |
| TAGGAAGCCG | ACTTATGCTA | TAATGTGAAT | GACAAGTATC | CTTTAGCCCT | TCCCACAGGC | 13893 |
| ATTTTAATTT | TCAAAAGGGC | ATTGCACAAC | CGCAGAGACA | CTAAGAAGAG | AGGTTTGGTG | 13953 |
| ATCAGAGTTA | CAGCCCCAGC | CTCCCAGCTG | GTGGCCCGGC | TGGTGCAGGT | GTGTCGAAAG | 14013 |
| CAGTAGTTTC | TGCTTCAGTG | AAACTTGAGG | ATCCTTTATT | TAGCCAGTTC | AGGGGCGGAA | 14073 |
| TGGCCATGCG | AAGTCTATGT | GTCACAGGTG | TCAGGCCCCC | ATATCCTGCT | GAGTCTAGAA | 14133 |
| TCAGCTACGT | AGCAGTTTTG | GGGGTATTGC | CAGACTGGGA | GTTTACATCC | CAGAAGCGAG | 14193 |
| AATGGTGGGG | TTCCTATACT | GCTCCAGACA | GGATCTTTCC | CCCAAGTTTG | TCAGCCACCT | 14253 |
| CTCTTCAAGT | CCCTTGGCTC | TGACCAGCAA | GACGTATCCA | AAAGAAACTG | AGGAGGCCCT | 14313 |
| TCACTTCTTT | TTAGGATAGT | GTGGGGCCAG | CATGGTGGGG | GTTGGGAATG | GCTTTCTGTC | 14373 |
| TCTTCCATCA | TCACAGGCTA | CTTCCAGAG | ACACTTTGAT | TCTGGGCATC | TCCAGCAGTC | 14433 |
| ACCTGGCCCA | CAATGCTTTG | CTGCCCTTTG | CTTCAGCCAC | TGTATCTGGT | TGTCCCTTGA | 14493 |
| AGGTGAGCCA | GAGCTCCTAG | GCAGAGAGCA | TGTGCTATAC | AAAGCCGTAG | GCTGGGCCCT | 14553 |
| GGGAACCTTC | TTGCTGTCAT | CCTCCTGTCA | AACCCCTATG | GTATGGTAGC | CCACATAAGG | 14613 |
| CTTGTGCAAA | AAACAGGCCA | AAACATAAGT | TATCTTTTCA | CTCTATCGGG | TCTTCTCATT | 14673 |
| TTCCCATGGT | ACGTTCGGCT | GGCCAGGCCC | AAAAGATTTG | AAGAGAGGTG | GCTGGCAAGT | 14733 |
| CTAGGGGAAT | AGGTCTATCT | GGTTCCCTCC | AGGAGCAGTG | CCTAGTGAGA | GGCTGGGCTG | 14793 |

| | | | | | | |
|---|---|---|---|---|---|---|
| GGCAGGGCAG | GGCCCCTTGC | TCCACATTGC | CTGAAGTCCC | GCCCTGCCCG | TCCTGGCTGG | 14853 |
| GATCTGGCAG | GTCTTCCAGC | TCCACACCCG | GCTCTCAGCT | GAGCCTGCTC | AGAGACTAGT | 14913 |
| CCTGGCATGT | GGGTTGCAGG | GCTGGTTCCA | GCTCCACCAG | GAGGTATGGG | CGTCTGGGTA | 14973 |
| CTCATGGGAC | ATTGACCTGT | AGTGGGTATG | GAGAGTGGAG | GAATGGTACA | GGCAGGTGTG | 15033 |
| CTGGTGCTGA | CGGACTTGAC | TCCGGCATTG | ACCTTGGCTT | GCAGTCTGGT | GTTAAACTAA | 15093 |
| CAGGGAATGC | TGACAAAAAA | GACAGTTATT | AAAACCAAGA | CAGGATACTG | CTTTCCCACT | 15153 |
| CAGCCCATTC | CCAAGAATCC | CCAAGACGTA | CAGGAAATGT | GCAACAGCAG | TGGGAATTGC | 15213 |
| TGAGTTGGGG | GATGTGGGTG | AGCTGTGTGC | TCCAGGGAA | TTTTGGGAAA | TTCCCCTCCG | 15273 |
| TTGAAATGCT | GTCAGGGTCT | GAGCCTTGGA | GGTGTTTTTG | GGGTGCTGTG | CTCCCCAGCT | 15333 |
| AAGCAGCTAA | CAGTCCTCTT | TACCTGCCTT | GTCCTCACCT | TGCCCCACCC | TGGGTTGGGC | 15393 |
| CTCTCGTTCA | CTCCCTGCTG | GGTCACCAGT | ACTTCAGTGC | AGGTCTCAGC | TTGATTCTTG | 15453 |
| GTGGAGAGAG | AGAAAGTTGA | TAAATCAGGG | TGCCTGTCAG | CCGGAAATTT | GGGTGTGTCC | 15513 |
| TGAAGGCACC | AATGGGGGCC | CTCCCTTCTG | GAGGTGGCTT | TAGGAAGGGG | TTTCTGGGTC | 15573 |
| TTGAGGCCTC | CTTACAGTTT | CTTAGCTCCA | TGGGAGAGAA | GTGAGGAGTT | GGGTATCGTC | 15633 |
| ACCCCAGCAT | GAATCTCTGG | TCACCTCTCA | GCATGCACTG | TCCAGCCTGA | TCTTTGAGTG | 15693 |
| CCATAAAAGA | ACAGAATTAT | CCTCTCAGAG | CACTTCATTT | CCCGCCAGCA | CAGTGGGTAC | 15753 |
| AGAGACAAGC | TGCCCAGACT | CCCAGCGAGG | GACTAGTTGA | GCCCAGCAT | GGGACTAGTT | 15813 |
| GAGCTAGACC | TGATACAGTC | CCAGAGAGCC | TCGTTGAGGA | AGCTTTGGGA | AAATTCACCC | 15873 |
| AGCATTTCAG | CCAGGACTGG | AGGAAAAGGT | GATTATGGGA | AAGAGAGCAG | TCAAGACCCC | 15933 |
| AGGCTGTAGG | ACACAGGATA | CAAACTGAGA | GCTACCGGAT | AGGAGTAGGT | TTTAGTCACA | 15993 |
| ATCTCTCCTG | TCCGCCCTAC | CCTCCAGGAG | ACATTGCACC | TTGTAGAACA | GCTGCCCCGG | 16053 |
| AGTCCACCTT | TGGGCCCCCC | TGGGTAGCTC | AGTAGTGTCA | GCATCCTCTC | ATTGACATCA | 16113 |
| GTCAGGTTAC | ACAGTGGGGC | AGCTAATGTG | AAGGCGCTAG | GCTGGGAAGC | CAGCTACTTG | 16173 |
| GGAAAACTAG | GTTGTTCCTG | GTAGGCCCTA | GCAGGAAGGC | AGTTCCTCCT | TTTCTTGGTG | 16233 |
| GCTTTAGGGG | TCTTTGGAAG | CTTTGAATGT | TCCCTCAGCT | CGTTGGTGAA | GCAGGCCCTC | 16293 |
| CTGGTACTGT | GGTGTTTGTC | TTCGAAGAGT | GAAGGCATTG | GAAGTAAAGA | CTGATGGGGC | 16353 |
| GCCTTCCCAG | GATGCTTTGC | TTCTTGCGCT | GGCTTACAGA | GCTCTCTTGC | TACCTAGTGC | 16413 |
| CTTGACTTTG | AACACCAGAT | TCAGTCAGGG | AACAGGAGTA | GAGGTCTTGC | CTTGCTGAGC | 16473 |
| CCCTGCGCAC | TGCAGGAAAA | GACTCCTCTG | AGTGGAGCCT | TTCCTCCTCA | GGTGACTGCT | 16533 |
| TTCAAAGTAC | AGCAGCCTCT | GAGGGGGAAG | TGTCATTTGA | CATTGTGGTA | GTTCTTGGGG | 16593 |
| TCCCTGGATA | CAGATGTCAT | GCCCAGATCA | TAGGTCTGTT | TGTACAGAGG | GAGGCGAGTT | 16653 |
| CTGTAGCTCA | GAGTCCTCAG | TACCCCAGAG | TTGTGGCTCT | AGGGGTGAGA | GGAGAAGACT | 16713 |
| ACAGCCCTTC | AATCACAGGT | CTGACCTGTG | GGTAGGGGTA | GATCTCTTGC | ATACTATGAA | 16773 |
| CCTGTTTGAA | ACCCCTGGGT | ATTTGCTGTG | GAATAGAGTC | TTGGTTGGGT | AAGAATGGTG | 16833 |
| GATGTTTATC | TTGGTGTGAC | TCTCGGGTGG | GGGTGGGGGA | TATGTCCCTG | TCTTTCCCAA | 16893 |
| TGTAGTATGC | TGAGTGGACA | GAGACCGTGT | GACTGAAGCC | TGGGCTCCTG | GAACAGGTGT | 16953 |
| GTGTTGGTGG | GGGGTGGGGC | GCAACTATCT | GGGATCCAGA | CTGCTTGGGA | ATGGCTGTGA | 17013 |
| CCCAGCTCCT | TTGATAACAG | CAGCTCTTTG | TCACTGGATG | TTGTGACTAA | TGGGACTTGT | 17073 |
| TGATTCAGTT | ACTCGGCTCC | CACCCACAGA | CGCCGGGGCT | TCTGTTGTGG | CACCAGGCAG | 17133 |
| CTGCAGACGG | CCCACAAGTT | TGCCTCGCTT | TCCCACTCCA | CGAAGGTAAG | TTCCCAGCAC | 17193 |

| | | | | | | |
|---|---|---|---|---|---|---|
| TGCCCAAATT | AGAGACTTGT | GAGTGGTCCC | CTCATACCCC | ACTCCCTGAG | GCTTCTCCTG | 17253 |
| GAAGGCCTGG | AATGGGGCAC | TGGGTGTGTA | CGTGCTGTGG | TTTCTGTTAG | GGTCAAGACC | 17313 |
| AGGCTGTTTC | TTACCTGGCT | CGTACCTCCA | AGTTCCAGG | TGATGAGTCC | TGATTTTTGA | 17373 |
| AGTGAAGGAA | TCCATTTAAT | ATCAAAATTC | TGTGACCTTA | AATTTTTTC | TTTTATTATG | 17433 |
| TGTCATTTCA | TATGTACGCA | TATTTTTTG | TCTGTGTGTG | GACATGCTTG | TGGCGATCAG | 17493 |
| AGGACACTTC | AGAAAGTCAG | TTCTCTCCTG | CCGTGTGGGT | CCTGGGGAAT | CAAATCCAAG | 17553 |
| TTGTCAGGCT | TTATCCTGAA | AATAAAAAGT | AGACAGCCCT | TGGGATCCAA | AGCTTCTTAG | 17613 |
| GGCTGTGTGT | CTTAGACACC | ACCAGTGTTG | CACAGCTGGT | AACATGACAG | TGTCCTGGAG | 17673 |
| TGCTGATTGG | AAGCCACAGG | CCTCTGTGCA | GGGCGGTAGA | CTTCCAGGGT | ACGGGGCAGG | 17733 |
| TGGGCGTTCT | CTACAAAAAC | CTTGTAATCG | CGGACGTCTT | GGAGATGCCC | CCTAGGTATC | 17793 |
| ATGATTTTGG | TGTGTGACAC | AGCTGAACTG | TCTTCATACT | CAGGATATCA | TGAAGTGCTG | 17853 |
| GGGTGCAGAC | CACTCTCAGC | CTCAGGCAGC | CAGGACCCGG | GGCTCCATCA | GATTGCGGTG | 17913 |
| ACTACCACAG | AGGGTGGCCT | TCCTTCCGGT | CAGTGTGGGT | GTGGGAGCTG | GCAGGAAGTG | 17973 |
| GCTCCAGGCT | TCCTTTAAGC | ATCCTCTGCC | CACAGCCCCA | AACATGTTCT | TTGGCAATGG | 18033 |
| CTTGCAACTA | GAGGTGAACT | CTCTCCTGTA | CTATGTCCTG | ACCCACGCTG | CTGCATCTAT | 18093 |
| TATACCTTTC | ACACGCGTGA | TGGGTACCCA | GCGGGCTGC | TAGGCAGGGT | TAAGCACTCA | 18153 |
| TCTTGTTTCC | TGGTGCTGAA | GCTGTGGTAA | AGAAACTGAG | GCCATTTTCC | CTTGAGAGAG | 18213 |
| ATGGTCTCAG | CCAGGTCTTT | CTCGGCCTGG | GGAGCCCGGA | AGAAAGGATG | TACTACAGTG | 18273 |
| AGTGGACACT | TGTTGGCTGA | TGGCCTTGGT | AGGTCCTTCA | CCCTGGGAAG | TGCTGTTTCT | 18333 |
| TATCTGTTAG | AGATGCTGAC | CTCAGCAGGA | CTGGAGGAAC | TGCATGGGAG | GTGTAGGAAT | 18393 |
| GAAAGTGAGT | GGGGAAAATT | ATCTCCAGCC | CTAGGGAAGT | CTGAGGCCTG | TGTCCCCTTT | 18453 |
| GTCCTGGACT | GGGCCCCTGC | CTTGGGTGTC | TGTCCAGGGT | CTTTGCTCTA | CAGCCCCAGC | 18513 |
| GGATGCCCAA | AGTAGACGAG | TCAACTGGTC | CTTTCTTTCA | CCCTGTGTCC | ACTTCTCATG | 18573 |
| TATCTACCTT | CATAATCCTT | CTAGGTAAAA | CAAGCCTCTA | ACTTTGGGTT | TTCAAATCAG | 18633 |
| CCAGCTTCCA | GGCTCGATAG | TACGAACCAT | GAAAATCTTT | CTTACCATGA | GGTTGTTTTC | 18693 |
| TAGTGTGTGT | GTGTGTGTGT | GTGTGTGTGT | GTGTGTGTGT | GTGTGTGTAC | GTACACATAT | 18753 |
| GTACCTCTAT | CAGTGTGCTG | TGCGTGTACC | ACAGCAGACT | CGTGAGGAGG | TCAGGCAAAC | 18813 |
| TTTATAAAAA | TCTTTTTTTT | TTGCTTCACT | TGAGTCCCAG | GGTCACACAG | TGGCAAGTGC | 18873 |
| TGAGCTCTGT | TCTCTGTTCT | TGATTTGTTT | TGTGAGCAGC | TGATGTTCTT | AAGGCTTGCG | 18933 |
| GAGGGGAAAG | GTAGGGCTGG | CTTGCTTCTT | CCCCGAGTGG | CGGTCAATCC | CTAGACATCT | 18993 |
| CTAAGCCGTG | GCCACACGTC | CTGGAAGGAC | CCAGGTCAGA | AGTGATACTG | AGATGGCCCT | 19053 |
| GTGAGCCCTC | TCGAACACAC | AGGGTTGTAA | ATAGTACCTG | ATTGTTACAT | GGAGACTCG | 19113 |
| TCAGCTGGGT | GGAGTCCTGG | TTCAGAGGGA | GTTATTCCTC | CCCCCACATT | TCTTCTCTTC | 19173 |
| TGGGGCTGAA | GTCTCTTCCT | TCCTTACCTG | TGATGCTGTC | ATGATAGGTC | CCAGCTGAGA | 19233 |
| GTGGAGGCGG | GGCAGTCAGG | GAGCTGCTTC | TCTTTGCTTA | GCAGGGGTTG | GAGACTTGGG | 19293 |
| GTGTAGGGGT | TGGCTCCCCC | TTTCCCTGCC | CTGGACCTGG | TTTCTGGTTT | CAGCAGAGAT | 19353 |
| TCGTTCTAGA | AACTTGTTGC | GTAAACAAGA | TCACAAAGCG | ATAAGCTTGA | GCAAAACCCA | 19413 |
| GGGGAACAAA | TTGCTTCCCT | GTGAAGACCC | AATCTTAGCT | CTTAGAGAAG | CCCTCCCTTT | 19473 |
| TGGAAATTGC | TGACTTTCAG | GGCTTCTCTG | TGGAGGAAAG | AGGCTAGCCG | CCGTATGTTT | 19533 |
| GCCTGGATTC | CAATAAATCT | TTGCGGCCTT | GGCTACCCCT | TGTTGAACAA | GGTCTGCACT | 19593 |

| | | | | | | |
|---|---|---|---|---|---|---|
| CCTAATGCGT | GCCTCAGGTG | GTCTGAGACC | TCTACCCCAT | CTCCAGCTTT | TCCTTCCTAT | 19653 |
| GGAGGGAGTC | AGTGGGTTAG | GAGAGAATGG | AGTTGAGTCC | TGGAATGAGG | AGGAAGCTAT | 19713 |
| GAACTCGGGG | CCTGTTCCTG | TCTGGTGGGT | GCTCTTCTCC | GCCGCTGAAG | GAGGCAGCCG | 19773 |
| CAGGGAAGAC | TACCACAGGA | ATCCGAGTAC | CACCTGGAGC | AGTGTATACA | GGATGTGGGC | 19833 |
| TGATGTGTGG | TAAGGGCATG | ATGGGCTGAT | GTGTGGTAAG | GGCATGGGAT | CTGATTGCTC | 19893 |
| TGTGGATGGG | CCACAGGGAA | ATTTTTGAGT | GTCTACTGCA | GTAGTTCTCA | ACCTGTGGGT | 19953 |
| TGTGCGCCCC | TTGGTGGGAG | TTACATATTA | GATATTTACA | TTATGATTCA | TAACTGTAGC | 20013 |
| AAAATTACAA | TTGTGAAAGA | ACCAAGAAAT | CACCGCAGCA | TGAGAACCTG | TATTAAAGGG | 20073 |
| TCACGGTGTT | AGGAGGGTTG | AGAGCCACTC | ATCCTCTGGG | TCTAGGCCAT | GGCGGGCTGT | 20133 |
| AACTGCTCTC | TGGAGTTAAG | CCACAGTGAA | CCAGCTGTCC | TTGCAGATGG | ACTTGTGGAG | 20193 |
| GCTCCAAACC | TTTGTCCAG | GGGAGAAGAG | CTTGCTTTTG | CTTTGTACTT | TTAAAGGAAG | 20253 |
| TTCAGTGGTC | TTCGGGCCTT | GTGGCTGCTG | TGTGTGGAAG | TGCCCCTGTA | CAATAAGCTG | 20313 |
| TATAGATCGT | GTACAACTGC | AGTTTTCCTC | CGTGGGTCCA | CCAACCACTC | CTGACTCCAC | 20373 |
| GGATGAGTGA | GGCCAGTAGG | GCTGTGTGTG | GGTCCCTAGG | CCAAGCATCC | TGGACCACGA | 20433 |
| TGAGCCTCAG | CTAGACCACT | CTGGATCTTT | AGCAGAGGCT | CCTAGAGAGC | TGGCTGGCTT | 20493 |
| CCTCCTGCCT | TCTTTTCTCT | TAAAACTTCG | TCTCAATCGG | AAGCTCCTCT | GTGCACGTGA | 20553 |
| CCTCCAGGCC | TGGGGGTCGC | CACAAATCCC | CTCATCACAA | GACGAGCAGC | TCGCATGAGG | 20613 |
| GACACGACAC | TTGTTACCTA | CCAGGCTGTG | GGGTTTTGT | TGGTTGGTTG | TTTTGTTTTG | 20673 |
| TTTTGTTTTT | TTACTTGTAC | AGAAGTGTTG | TGACATCAGA | TGTCAGCTGT | TAGTGCTGGC | 20733 |
| ACCATTTTAC | AGGTAGGGAA | CTGAGGCTGT | AAGATGTGTA | GTGACATCGC | TAAGGCCACT | 20793 |
| CAGTTGGTGA | GGCCTTACCA | AGGTCAGGTC | TTTGGAGCCT | TTTGCTGAAC | CATGTACTTC | 20853 |
| TATCTCTGTT | TTGTTGAAAC | AAAGTCTATA | TGGCTCTGGC | TAGCCTATAA | CCCCATATGT | 20913 |
| AGACGAGGCT | GACCTCGAAT | ACACTGCAGT | CTTTTATGTC | TGCCTTCTGG | GTGGCAGGAT | 20973 |
| TGAAGGCATG | TGATTCCTCC | TAACTGTACA | CTTTAAAAAA | AAAATCATTC | TTTGTTCTGG | 21033 |
| TCTGTGCCAG | GGCCTTGTAA | GATGTTCTGT | GCTGAGCTGG | GCTATTTGGG | TTAGTCTCAT | 21093 |
| TGCTGAGCAG | GGCCCCTGTA | TCTTCCTTCT | CTGTCACTTG | CTTACCTGGG | TCTTCCTCCT | 21153 |
| GCACTAGCTA | TCCTAGAACC | AGTACTGAGA | GCAACTATGG | GCCCAACTCT | GCCCCTTGCC | 21213 |
| CAGCCTGCTT | AGCTGGGGGC | GGTGTTCCAC | TTCCCTGCCC | AAGTCCTGTG | GGACTGTGTT | 21273 |
| TGTACTCCAC | CACCTTCAGT | TCCTTGGAGC | TGGAGCAGGC | CAGGCGGCTG | CATTCCTGCA | 21333 |
| GCTGCTGTTG | CCAGGGAGAG | CCCATCCCAT | TCACTTCAGT | CTCCTTAATG | TAGAAGCTT | 21393 |
| GTCGAATTAG | CTTCCACTGT | CCCCAACCCA | AGAGTACCCT | GTCCTTTCTT | CACTAAGAAG | 21453 |
| GCCAGGATAC | AGTCCTTCCT | GTGGCTGATA | AGACAGGCCT | TGGGACAAGG | CCTGGGACCA | 21513 |
| CACTGTGTGG | GCAAAGCTGC | TTCAGCACCG | ATGGCTCCTC | CATGCCAAGC | TTGGCTCTGC | 21573 |
| TTCTCACAGT | TGAGACTTCT | GTGCGCACAC | CCACTGTCTA | GCTCAGCTGG | ACACTGATTT | 21633 |
| TCTTTAAATG | TATAGATTTT | GGGGTGGGGT | GTGCTGAAAG | CTCCCACTGA | TGCCCCAAGC | 21693 |
| CTGAGTCTCA | GAGTATGATC | AATTGATGGC | TTTCATGGGT | ATCACAGCTT | CTGTTCCAG | 21753 |
| GTCAGACTCC | CTGACCAGTC | AGAGCATCCT | GGGGTTAGAC | AATGTCCCCG | TCACTTGTGC | 21813 |
| CTCCACCTGG | CACCAGGCTA | TGATGTTATG | GCATTGAGGG | TATGAGAAGG | ACCAGGGGTT | 21873 |
| TCCCAGAGTT | ACGCCCAGGC | GCACAGGCAA | TTGTTTCCTA | CATGTGTGGC | TGGAATGGTT | 21933 |
| GGGTGAGCCT | TTTCAGCTGC | CTACAATAGG | AACCCAGGGA | TACTGGGCAT | TGACCAAGGC | 21993 |

-continued

| | | | | | | | | | | | | | | |
|---|---|---|---|---|---|---|---|---|---|---|---|---|---|---|
| ATATCTCATA | CCCTTTTCTT | ATCTTTCTGC | AG CAA | ATT | GTG | GCT | GTA | AAT | GTT | | | | | 22046 |
| | | | Gln 1 | Ile | Val | Ala | Val 5 | Asn | Val | | | | | |

```
CCT  CCT  GAA  GAT  CAG  GAT  GGC  TCT  GGG  GAT  GAC  TCT  GAC  AAC  TTC  TCT          22094
Pro  Pro  Glu  Asp  Gln  Asp  Gly  Ser  Gly  Asp  Asp  Ser  Asp  Asn  Phe  Ser
          10                       15                       20

GGC  TCT  GGC  ACA  G  GTAAGACTG  ACCCAGAACA  CTGAGATGGC  ATAGATCATG              22146
Gly  Ser  Gly  Thr  G
          25
```

| GCTGGAGTGG | TGAGCAGGCA | GTCACCCAGC | TTTTAGTGAA | CCCCCTTCTT | CTCCCATCCC | 22206 |
|---|---|---|---|---|---|---|
| ATCCTTAGCC | ATTGGAGTCA | GGACAGTGCC | AAAAGGAAGA | ATGGTATCCA | GCTGCAAGCC | 22266 |
| ACTCAGCTAA | GAGAAACTCT | CAGAGAAATG | AAGGGGTTCC | ACCAGGCCAT | GGGCAGCCAC | 22326 |
| TAGAGCCAAC | CCTTGGAGGA | GTTTGACTCC | ACTGAGCCTT | GGTGTGGTGT | TTCCATCTGT | 22386 |
| GAGATGGGAA | TACTTTGCCC | AAGAGCCTGT | TAGAAGCTGT | AGGAAGCACA | GAGTCGGCTA | 22446 |
| GGTATAGATT | TGCTCTCACC | TCCATCTCTC | GATACCAGTT | CTCTGCAGAG | CTTGGGTTTG | 22506 |
| TGGGAGGGT | GGGGGGGTGA | GGGGAGAAGG | CTGTGAGCTG | CAGCTAGCCA | GAGGGGTCTC | 22566 |
| CCAGAAGAAT | GGGGAGAGCT | AAGAAGGAAA | GTTGAGGTCA | CAGTGGGAAG | GAGACCAGAG | 22626 |
| CAAAGGGTTG | GAAGGTAGGT | AAAATGCAGC | CGTGTATTCT | TGGGAGCCTT | AGGCCTTGGG | 22686 |
| CAAGAGGGTA | GAAGAGGTGT | TTGTCCTGGG | CTGCAGTCCT | GTATCAGCTC | TGGTGTCTTG | 22746 |
| GCCCACGCTC | ACAGCAGGAT | CCCTTCCCAG | ATTCCCGAGA | ATTTCTCACA | GTTCAGAGAG | 22806 |
| CACGCTACTT | GTAGGCAGGT | GAGGCTGCAA | AGGACAGCTT | TTCTGGCCTA | ATTTTCAAAG | 22866 |
| TGAGTTCAGC | CTTTGCTAGG | TCACCTTTGG | GGTCTCAGAA | GGCTTCAGCT | CCTGGTAGAG | 22926 |
| CATGAATCAC | GTCAGGCGTG | ATGCTGGAGA | CCTCTCCTAC | CCTGACACCC | CAAACCCCCA | 22986 |

```
CCTCTGACCC  TGCAG  GT  GCT  TTG  CCA  GAT  ACT  TTG  TCA  CGG  CAG  ACA  CCT       23036
                   ly  Ala  Leu  Pro  Asp  Thr  Leu  Ser  Arg  Gln  Thr  Pro
                   1                 5                            10

TCC  ACT  TGG  AAG  GAC  GTG  TGG  CTG  TTG  ACA  GCC  ACG  CCC  ACA  GCT  CCA     23084
Ser  Thr  Trp  Lys  Asp  Val  Trp  Leu  Leu  Thr  Ala  Thr  Pro  Thr  Ala  Pro
               15                 20                       25

GAG  CCC  ACC  AGC  AGC  AAC  ACC  GAG  ACT  GCT  TTT  ACC  TCT  GTC  CTG  CCA     23132
Glu  Pro  Thr  Ser  Ser  Asn  Thr  Glu  Thr  Ala  Phe  Thr  Ser  Val  Leu  Pro
               30                 35                       40

GCC  GGA  GAG  AAG  CCC  GAG  GAG  GGA  GAG  CCT  GTG  CTC  CAT  GTA  GAA  GCA     23180
Ala  Gly  Glu  Lys  Pro  Glu  Glu  Gly  Glu  Pro  Val  Leu  His  Val  Glu  Ala
          45                  50                       55

GAG  CCT  GGC  TTC  ACT  GCT  CGG  GAC  AAG  GAA  AAG  GAG  GTC  ACC  ACC  AGG     23228
Glu  Pro  Gly  Phe  Thr  Ala  Arg  Asp  Lys  Glu  Lys  Glu  Val  Thr  Thr  Arg
60                  65                       70                       75

CCC  AGG  GAG  ACC  GTG  CAG  CTC  CCC  ATC  ACC  CAA  CGG  GCC  TCA  ACA  GTC     23276
Pro  Arg  Glu  Thr  Val  Gln  Leu  Pro  Ile  Thr  Gln  Arg  Ala  Ser  Thr  Val
                    80                  85                       90

AGA  GTC  ACC  ACA  GCC  CAG  GCA  GCT  GTC  ACA  TCT  CAT  CCG  CAC  GGG  GGC     23324
Arg  Val  Thr  Thr  Ala  Gln  Ala  Ala  Val  Thr  Ser  His  Pro  His  Gly  Gly
               95                      100                      105

ATG  CAA  CCT  GGC  CTC  CAT  GAG  ACC  TCG  GCT  CCC  ACA  GCA  CCT  GGT  CAA     23372
Met  Gln  Pro  Gly  Leu  His  Glu  Thr  Ser  Ala  Pro  Thr  Ala  Pro  Gly  Gln
          110                      115                      120

CCT  GAC  CAT  CAG  CCT  CCA  CGT  GTG  GAG  GGT  GGC  GGC  ACT  TCT  GTC  ATC     23420
Pro  Asp  His  Gln  Pro  Pro  Arg  Val  Glu  Gly  Gly  Gly  Thr  Ser  Val  Ile
          125                      130                      135

AAA  GAG  GTT  GTC  GAG  GAT  GGA  ACT  GCC  AAT  CAG  CTT  CCC  GCA  GGA  GAG     23468
Lys  Glu  Val  Val  Glu  Asp  Gly  Thr  Ala  Asn  Gln  Leu  Pro  Ala  Gly  Glu
140                 145                      150                      155
```

```
GGC TCT GGA GAA CAA GTGAGTGGCT TTGCATTTCC TGGGTGGCCA CTAGTGCCTG    23523
Gly Ser Gly Glu Gln
            160

CACCTGGCCG CCTAATGTCC TCATTACAGT GACAGGTGAC AGGGTCCAC CTTCCTCCTG    23583

CCCGAAACAG ACTGATTGCA AGATCAGGAG GTGGGCGACT CCTTAGATGT CATTCAGGAG   23643

CTTACAGCAG GGTGAATTTT CCGTCTTAGA CCTTCATGGG AATTTTCACA CAACAATGTG   23703

TACGTTGTGT CACTGGAGGC GGTATCTGTG TCTTGGCCTG CCAGGGTCCC AGGTGTGACT   23763

GACTGCATTC CTTGACAGAT GCTGGTATAG GTTGGCTACG TCTGATGGGG GTGGCAGGGG   23823

ATCCCATCAG GTATGGCACT GCTCAGGTTG CTGTTGTGTC AGTGGCTCCA GCTGACCTGA   23883

TCCCAACCTA CCCTTCTGTA G GAC TTC ACC TTT GAA ACA TCT GGG GAG AAC    23934
                        Asp Phe Thr Phe Glu Thr Ser Gly Glu Asn
                         1           5                        10

ACA GCT GTG GCT GCC GTA GAG CCC GGC CTG CGG AAT CAG CCC CCG GTG    23982
Thr Ala Val Ala Ala Val Glu Pro Gly Leu Arg Asn Gln Pro Pro Val
             15              20                     25

GAC GAA GGA GCC ACA GGT GCT TCT CAG AGC CTT TTG GAC AGG AAG GAA    24030
Asp Glu Gly Ala Thr Gly Ala Ser Gln Ser Leu Leu Asp Arg Lys Glu
         30              35                  40

GTG CTG GGA G GTGAGTCTT CTTTCAGGTG GAGAGGAGGA GGCAGGTGGT           24079
Val Leu Gly G
         45

GGCTCTGAGG TAGCCTGGGT TGCTGGGGTG AAGCATCTTT AGCAGCAGGG TGGGGAAGGA   24139

GGAGGGTCAA TTCTACTCCA GGCCACCTCC TAGGCTGTCC GTCTAGTCTG GGAGAGACTA   24199

CCACTGACCC CGTGGAGCTA CTGATCTGAG CCTGCCTCTG TTCACTCCCT AG GT GTC   24256
                                                         ly Val
                                                          1

ATT GCC GGA GGC CTA GTG GGC CTC ATC TTT GCT GTG TGC CTG GTG GCT    24304
Ile Ala Gly Gly Leu Val Gly Leu Ile Phe Ala Val Cys Leu Val Ala
             5                10                     15

TTC ATG CTG TAC CGG ATG AAG AAG AAG GAC GAA GGC AGC TAC TCC TTG    24352
Phe Met Leu Tyr Arg Met Lys Lys Lys Asp Glu Gly Ser Tyr Ser Leu
         20                 25                  30

GAG GAG CCC AAA CAA GCC AAT GGC GGT GCC TAC CAG AAA CCC ACC AAG    24400
Glu Glu Pro Lys Gln Ala Asn Gly Gly Ala Tyr Gln Lys Pro Thr Lys
     35                 40                   45

CAG GAG GAG TTC TAC GCC TGATGGGGAA ATAGTTCTTT CTCCCCCCAC           24448
Gln Glu Glu Phe Tyr Ala
 50                 55

AGCCCCTGCC ACTCACTAGG CTCCCACTTG CCTCTTCTGT GAAAAACTTC AAGCCCTGGC   24508

CTCCCCACCA CTGGGTCATG TCCTCTGCAC CCAGGCCCTT CCAGCTGTTC CTGCCCGAGC   24568

GGTCCCAGGG TGTGCTGGGA ACTGATTCCC CTCCTTTGAC TTCTGCCTAG AAGCTTGGGT   24628

GCAAAGGGTT TCTTGCATCT GATCTTTCTA CCACAACCAC ACCTGTTGTC CACTCTTCTG   24688

ACTTGGTTTC TCCAAATGGG AGGAGACCCA GCTCTGGACA GAAAGGGGAC CCGACTCTTT   24748

GGACCTAGAT GGCCTATTGC GGCTGGAGGA TCCTGAGGAC AGGAGAGGGG CTTCGGCTGA   24808

CCAGCCATAG CACTTACCCA TAGAGACCGC TAGGTTGGCC GTGCTGTGGT GGGGGATGGA   24868

GGCCTGAGCT CCTTGGAATC CACTTTTCAT TGTGGGGAGG TCTACTTTAG ACAACTTGGT   24928

TTTGCACATA TTTTCTCTAA TTTCTCTGTT CAGAGCCCCA GCAGACCTTA TTACTGGGGT   24988

AAGGCAAGTC TGTTGACTGG TGTCCCTCAC CTCGCTTCCC TAATCTACAT TCAGGAGACC   25048

GAATCGGGGG TTAATAAGAC TTTTTTTGTT TTTTGTTTTT GTTTTAACC TAGAAGAACC    25108

AAATCTGGAC GGCAAAACGT AGGCTTAGTT TGTGTGTTGT CTCTGAGTTT GTCGCTCATG   25168
```

| | | | | | |
|---|---|---|---|---|---|
| CGTACAACAG | GGTATGGACT | ATCTGTATGG | TGCCCCATTT | TTGGCGGCCC | GTAAGTAGGC | 25228
| TGGCTAGTCC | AGGATACTGT | GGAATAGCCA | CCTCTTGACC | AGTCATGCCT | GTGTGCATGG | 25288
| ACTCAGGGCC | ACGGCCTTGG | CCTGGGCCAC | CGTGACATTG | GAAGAGCCTG | TGTGAGAACT | 25348
| TACTCGAAGT | TCACAGTCTA | GGAGTGGAGG | GGAGGAGACT | GTAGAGTTTT | GGGGGAGGGG | 25408
| TGGCAAGGGT | GCCCAAGCGT | CTCCCACCTT | TGGTACCATC | TCTAGTCATC | CTTCCTCCCG | 25468
| GAAGTTGACA | AGACACATCT | TGAGTATGGC | TGGCACTGGT | TCCTCCATCA | AGAACCAAGT | 25528
| TCACCTTCAG | CTCCTGTGGC | CCCGCCCCCA | GGCTGGAGTC | AGAAATGTTT | CCCAAAGAGT | 25588
| GAGTCTTTTG | CTTTTGGCAA | AACGCTACTT | AATCCAATGG | GTTCTGTACA | GTAGATTTTG | 25648
| CAGATGTAAT | AAACTTTAAT | ATAAGGAGT | CCTATGAACT | CTACTGCTTC | TGCTTCTTCT | 25708
| TCTCTGGACT | GGTGGTATAG | ATATAGCCAC | CCTTTGCCCA | AACCCTGGTA | GCTCGGGAA | 25768
| GCTTGGCTTA | AGGCTGCACG | CCTCCAATCC | CCCAAAGGTA | GGATCCTGGC | TGGGTCCAGG | 25828
| GTTCCTCTGA | TTTATTTGGT | TTTGTTGTGT | TGTGTTGTGT | TTTTCTTTTG | GCTAAACTTC | 25888
| TTTTGGAAGT | TGGTAAGTTC | AGCCAAGGTT | TTACAGGCCC | TGATGTCTGT | TCTTCTAAAT | 25948
| GGTTTAAGTA | ATTGGGACTC | TAGCACATCT | TGACCTAGGG | TCACTAGAGC | TAAGCTTGCT | 26008
| TTGCAGGGCA | GACACCTGGG | ACAGCCTTCC | TCCCTCATGT | TTGCTGGGAC | ACTGCTGAGC | 26068
| ACCCCTTGCT | TACTTAGCTC | AGTGATGTTC | CAGCTCCTGG | CTAGGCTGCT | CAGCCACTCA | 26128
| GCTAGACAAA | AGATCTGTGC | CCTGTGTTTC | ATCCCAGAGC | TTGTTGCCAG | ATCACATGGC | 26188
| TGGATGTGAT | GTGGGGTGGG | GGTGGGGTCA | TATCTGAGAC | AGCCCTCAGC | TGAGGGCTTG | 26248
| TGGGACAGTG | TCAAGCCTCA | GGCTGGCGCT | CATTCATATA | ATTGCAATAA | ATGGTACGTG | 26308
| TCCATTTGGA | CAGCAGACAC | TTTGGTGTAC | TTGTGCAGTC | TCTTTTTGGT | CTGGACCATG | 26368
| TCCAACTCTA | TCTGGTTTTT | GGAATGGGAG | CCTAACTGGC | CTGTGTTCTG | GCTTGGTACC | 26428
| AAATAGCAAC | AGTCAGTGGC | ATCCTTGCCC | AGGCCCCAGG | GCAGGACTAT | GCTCTTGCCA | 26488
| TATCCAGGAC | TCCCGACTTT | GCACCTGTTT | TCCCTCTGTG | TGTAGCATCA | TGAACTCCAG | 26548
| CTAGGTTGTT | CCTTCCCTG | GGGTCAGGAG | GATTCTGCTG | ACTCTGAATG | TCAGGATTTG | 26608
| CTTTTGTTCT | GTTTGCTTAT | TGGGCAATTC | TCAACCTTCA | CTAGCAACAG | TCTCATGTGT | 26668
| CAGGATTACA | AGTATTGCTT | GCACATTGAG | GG | | | 26700

( 2 ) INFORMATION FOR SEQ ID NO:6:

( i ) SEQUENCE CHARACTERISTICS:
        ( A ) LENGTH: 311 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Arg  Arg  Ala  Ala  Leu  Trp  Leu  Trp  Leu  Cys  Ala  Leu  Ala  Leu  Arg
 1                  5                  10                  15

Leu  Gln  Pro  Ala  Leu  Pro  Gln  Ile  Val  Ala  Val  Asn  Val  Pro  Pro  Glu
                20                  25                  30

Asp  Gln  Asp  Gly  Ser  Gly  Asp  Asp  Ser  Asp  Asn  Phe  Ser  Gly  Ser  Gly
                35                  40                  45

Thr  Gly  Ala  Leu  Pro  Asp  Thr  Leu  Ser  Arg  Gln  Thr  Pro  Ser  Thr  Trp
        50                  55                  60

Lys  Asp  Val  Trp  Leu  Leu  Thr  Ala  Thr  Pro  Ala  Pro  Glu  Pro  Thr
65                  70                  75                  80

Ser  Ser  Asn  Thr  Glu  Thr  Ala  Phe  Thr  Ser  Val  Leu  Pro  Ala  Gly  Glu
```

-continued

|     |     |     |     | 85  |     |     |     |     | 90  |     |     |     |     | 95  |
|-----|-----|-----|-----|-----|-----|-----|-----|-----|-----|-----|-----|-----|-----|-----|
| Lys | Pro | Glu | Glu | Gly | Glu | Pro | Val | Leu | His | Val | Glu | Ala | Glu | Pro | Gly |
|     |     |     | 100 |     |     |     |     | 105 |     |     |     | 110 |     |     |
| Phe | Thr | Ala | Arg | Asp | Lys | Glu | Lys | Glu | Val | Thr | Thr | Arg | Pro | Arg | Glu |
|     |     | 115 |     |     |     | 120 |     |     |     |     | 125 |     |     |     |
| Thr | Val | Gln | Leu | Pro | Ile | Thr | Gln | Arg | Ala | Ser | Thr | Val | Arg | Val | Thr |
|     | 130 |     |     |     |     | 135 |     |     |     |     | 140 |     |     |     |
| Thr | Ala | Gln | Ala | Ala | Val | Thr | Ser | His | Pro | His | Gly | Gly | Met | Gln | Pro |
| 145 |     |     |     |     | 150 |     |     |     |     | 155 |     |     |     |     | 160 |
| Gly | Leu | His | Glu | Thr | Ser | Ala | Pro | Thr | Ala | Pro | Gly | Gln | Pro | Asp | His |
|     |     |     |     | 165 |     |     |     |     | 170 |     |     |     |     | 175 |     |
| Gln | Pro | Pro | Arg | Val | Glu | Gly | Gly | Thr | Ser | Val | Ile | Lys | Glu | Val |
|     |     |     | 180 |     |     |     |     | 185 |     |     |     |     | 190 |     |
| Val | Glu | Asp | Gly | Thr | Ala | Asn | Gln | Leu | Pro | Ala | Gly | Glu | Gly | Ser | Gly |
|     |     | 195 |     |     |     |     | 200 |     |     |     |     | 205 |     |     |     |
| Glu | Gln | Asp | Phe | Thr | Phe | Glu | Thr | Ser | Gly | Glu | Asn | Thr | Ala | Val | Ala |
|     | 210 |     |     |     |     | 215 |     |     |     |     | 220 |     |     |     |
| Ala | Val | Glu | Pro | Gly | Leu | Arg | Asn | Gln | Pro | Pro | Val | Asp | Glu | Gly | Ala |
| 225 |     |     |     |     | 230 |     |     |     |     | 235 |     |     |     |     | 240 |
| Thr | Gly | Ala | Ser | Gln | Ser | Leu | Leu | Asp | Arg | Lys | Glu | Val | Leu | Gly | Gly |
|     |     |     |     | 245 |     |     |     |     | 250 |     |     |     |     | 255 |     |
| Val | Ile | Ala | Gly | Gly | Leu | Val | Gly | Leu | Ile | Phe | Ala | Val | Cys | Leu | Val |
|     |     |     | 260 |     |     |     |     | 265 |     |     |     |     | 270 |     |     |
| Ala | Phe | Met | Leu | Tyr | Arg | Met | Lys | Lys | Lys | Asp | Glu | Gly | Ser | Tyr | Ser |
|     |     | 275 |     |     |     |     | 280 |     |     |     |     | 285 |     |     |     |
| Leu | Glu | Glu | Pro | Lys | Gln | Ala | Asn | Gly | Gly | Ala | Tyr | Gln | Lys | Pro | Thr |
|     | 290 |     |     |     |     | 295 |     |     |     |     | 300 |     |     |     |     |
| Lys | Gln | Glu | Glu | Phe | Tyr | Ala |
| 305 |     |     |     |     | 310 |     |

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

Ser  Gly  Xaa  Gly
  1

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: protein ( i x ) FEATURE:
        ( A ) NAME/KEY: Peptide
        ( B ) LOCATION: 1
        ( D ) OTHER INFORMATION: /label=Peptide
            / note= "The amino acid at position 1 may also be aspartic
            acid."

( i x ) FEATURE:
        ( A ) NAME/KEY: Peptide
        ( B ) LOCATION: 5
        ( D ) OTHER INFORMATION: /label=Peptide / note= "The amino acid at position 5 may also be aspartic acid."

( x i ) SEQUENCE DESCRIPTION: SEQ ID NO:8:

Glu Gly Ser Gly Glu
1               5